(12) United States Patent
Simmen et al.

(10) Patent No.: US 8,227,407 B2
(45) Date of Patent: Jul. 24, 2012

(54) MACROCYCLIC INHIBITORS OF HEPATITIS C VIRUS

(75) Inventors: Kenneth Alan Simmen, Tervuren (BE); Herman Augustinus De Kock, Arendonk (BE); Pierre Jean-Marie Bernard Raboisson, Sterrebeek (BE); Lili Hu, Mechelen (BE); Dominique Louis Nestor Ghislain Surleraux, Braine-le-château (BE); Karl Magnus Nilsson, Huddinge (SE); Bengt Bertil Samuelsson, Huddinge (SE); Åsa Annica Kristina Rosenquist, Huddinge (SE); Lourdes Salvador Odén, Huddinge (SE)

(73) Assignees: Medivir AB, Huddinge (SE); Tibotec BVBA, Eastgate, Little Island, Co Cork (IE)

( * ) Notice: Subject to any disclaimer, the term of this patent is extended or adjusted under 35 U.S.C. 154(b) by 603 days.

(21) Appl. No.: 11/995,835

(22) Filed: Jan. 16, 2008

(65) Prior Publication Data
US 2009/0062311 A1 Mar. 5, 2009

(51) Int. Cl.
A61K 38/55 (2006.01)
A61K 38/00 (2006.01)
(52) U.S. Cl. ................. 514/4.1; 530/333
(58) Field of Classification Search .......... None
See application file for complete search history.

(56) References Cited

U.S. PATENT DOCUMENTS

| 5,484,801 A | 1/1996 | A-Razzak et al. |
| 5,807,876 A | 9/1998 | Armistead et al. |
| 5,948,436 A | 9/1999 | Al-Razzak et al. |
| 6,037,157 A | 3/2000 | Norbeck et al. |
| 6,054,472 A | 4/2000 | Armistead et al. |
| 6,344,465 B1 | 2/2002 | Armistead et al. |
| 6,498,178 B2 | 12/2002 | Stamos et al. |
| 7,666,834 B2* | 2/2010 | Simmen et al. ............. 514/9 |
| 2005/0065073 A1 | 3/2005 | Wu et al. |
| 2005/0143316 A1 | 6/2005 | Tu et al. |

FOREIGN PATENT DOCUMENTS

| WO | WO 94/14436 A1 | 7/1994 |
| WO | WO 95/07696 A1 | 3/1995 |
| WO | WO 95/09614 A1 | 4/1995 |
| WO | WO 97/40028 A1 | 10/1997 |
| WO | WO 98/17679 A1 | 4/1998 |
| WO | WO 98/22496 A2 | 5/1998 |
| WO | WO 98/40381 A1 | 9/1998 |
| WO | WO 99/07734 A2 | 2/1999 |
| WO | WO 99/37666 A1 | 7/1999 |
| WO | WO 00/09543 A2 | 2/2000 |
| WO | WO 00/56331 A1 | 9/2000 |
| WO | WO 00/59929 A | 10/2000 |
| WO | WO 01/16300 A2 | 3/2001 |
| WO | WO 01/49262 A1 | 7/2001 |
| WO | WO 01/74768 A2 | 10/2001 |
| WO | WO 02/08198 A2 | 1/2002 |
| WO | WO 02/08244 A2 | 1/2002 |
| WO | WO 02/08256 A2 | 1/2002 |
| WO | WO 02/18369 A2 | 3/2002 |
| WO | WO 02/053557 A1 | 7/2002 |
| WO | WO 03/006490 A1 | 1/2003 |
| WO | WO 03/087092 A2 | 10/2003 |

(Continued)

OTHER PUBLICATIONS

Dewynter, G., et al. "Synthesis of Chiral Sulfahydantoins", Tetrahedron vol. 49, No. 1, pp. 65-76, (1993).

(Continued)

Primary Examiner — Cecilia Tsang
Assistant Examiner — Thomas Heard
(74) Attorney, Agent, or Firm — Andrea Jo Kamage

(57) ABSTRACT

Macrocylic compounds having inhibitory activity on the replication of the hepatitis C virus (HCV) of the general formula (I)

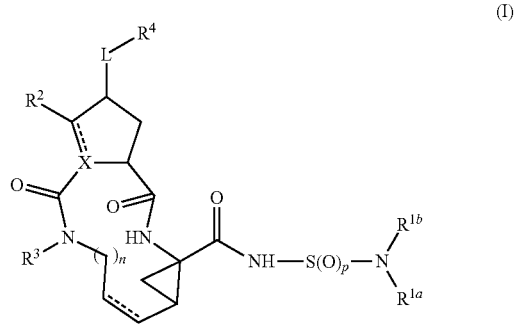

X is N, CH and where X bears a double bond it is C;
$R^{1a}$ and $R^{1b}$ are hydrogen, $C_{3-7}$cycloalkyl, aryl, Het, $C_{1-6}$alkoxy, $C_{1-6}$alkyl optionally substituted with halo, $C_{1-6}$alkoxy, cyano, polyhalo$C_{1-6}$alkoxy, $C_{3-7}$cycloalkyl, aryl, or with Het; or $R^{1a}$ and $R^{1b}$ together with the nitrogen to which they are attached form a 4 to 6 membered heterocyclic ring which may be optionally substituted; Het being a heterocyclic ring;
L is a direct bond, —O—, —O—$C_{1-4}$alkanediyl-, —O—CO—, —O—C(=O)—NR$^{5a}$— or —O—C (=O)—NR$^{5a}$—$C_{1-4}$alkanediyl-; n is 3, 4, 5, or 6; p is 1, or 2;
$R^2$ is hydrogen, and where X is C or CH, $R^2$ may also be $C_{1-6}$alkyl;
$R^3$ is hydrogen, $C_{1-6}$alkyl, $C_{1-6}$alkoxy$C_{1-6}$alkyl, $C_{3-7}$cycloalkyl, amino, mono- or di$C_{1-6}$alkylamino;
$R^4$ is aryl or a saturated, a partially unsaturated or completely unsaturated 5 or 6 membered monocyclic or 9 to 12 membered bicyclic heterocyclic ring system wherein said ring system contains one nitrogen, and optionally one to three additional heteroatoms selected from O, S and N, and wherein the remaining ring members are carbon atoms; wherein said ring system may be optionally substituted; and pharmaceutical compositions containing compounds (I) and processes for preparing compounds (I).

16 Claims, No Drawings

FOREIGN PATENT DOCUMENTS

| | | |
|---|---|---|
| WO | WO 2004/072243 A2 | 8/2004 |
| WO | WO 2005/010029 A1 | 2/2005 |
| WO | WO 2005/073195 A2 | 8/2005 |
| WO | WO 2005/073216 A2 | 8/2005 |
| WO | WO 2007/014921 A1 | 2/2007 |
| WO | WO 2007/014922 A1 | 2/2007 |
| WO | WO 2007/014923 A1 | 2/2007 |
| WO | WO 2007/014924 A1 | 2/2007 |
| WO | WO 2007/014925 | 2/2007 |
| WO | WO 2007/014926 A1 | 2/2007 |
| WO | WO 2007/014927 A1 | 2/2007 |

OTHER PUBLICATIONS

Graf, R., "On Sulfamic Acid Chloride", Chemische Berichte, vol. 92, pp. 509-513 (1959).
Weiss, G., et al. "Production and Reactions of N-Monoalkyl Amidosulfonyl Chlorides", Liebigs, Ann. Chem. 729, p. 40-51 (1969).
Bodanszky, M., "Peptide Chemistry", $2^{nd}$ Red. Ed., Springer-Verlag, Berlin, Germany (1993). Title Page and Table of Contents.
Bredikhina, Z. et al., "Synthesis and Some Reactions of 4-Carboxy-2-Thiiazolyhydrazones", Chem. Hyterocycl. Compd. (English translation) (1991), 427-433.
Briet, N. et al., "Synthesis of Novel Substituted Isoquinolones", Tetrahedron, 2002, 5761.
Cohen, E., et al. "Sulfamoyl Chloride, Sulfamides and Sulfimide", Organic Chemical Research Section, vol. 84, 1962, pp. 1994-2002.
Dickinson, R., et al. "Thromboxane Modulating Agenats. 3. IH-Imadozol-1-ylalkyl-and 3-pyridinylalkyl-substituted 3[2-[arylsulfonyl)amino]ethyl]benzenepropanoc Receptor Antagonists", J. Med. Chem. 1997, 40, pp. 3442-3452.
Dolby, L., et al., "Studies of the Synthesis of the B, C, and D Rings of Gibberellie Acid", in J. Org. Chem. 36 (1971) 1277-1285.
Elangovan, et al., "Sonogashira Coupling Reaction with Diminished Homocoupling", Organic Letters 2003 vol. 5 No. 11 p. 1841-1844.
Goodman and Gillman's "The Pharmacological Basis of Therapeutics" Eighth Edition, McGraw-Hill, Inc., Health Professions Division, p. 1-20 Title Page and Table of Conents, (1990).
Greene, "Protective Groups in Organic Chemistry", Wiley & Sons, NY (1999) "The Peptides: Analysis, Synthesis, Biology", vol. 9, Academic Press, NY (1987) Title Page and Table of Contents.
Han, W., et al. "α-Ketoamides, α-Ketoesters and α-Diketones as HCV NS3 Protease Inhibitors", Bioorganic & Medicinal Chemistry Letters, vol. 10, No. 8, 2000, pp. 711-713.
Huang, et al., "Olefin Metathesis-Active Ruthenium Complexes Bearing a Nucleophilic Carbene Ligand" J.Am. Chem. Soc. 1999 121, p. 2674-2678.
Kingsbury, J., "A Recyclable Ru-Based Metathesis Catalyst", et al., J.Am. Chem. Soc. 1999, 121, p. 791-799.
Kloeck, J., et al. "An Improved Synthesis of Sulfamoyl Chlorides", J. Org. Chem. vol. 41, No. 25, 1976, pp. 4028-4029.
Krchnak, V. et al., "Polymer-Supported Mitsunobu Ether Formation and its Use in Combinatorial Chemistry", Tetrahedron Letters, vol. 36, No. 35, p. 6193-6195, 1995.
Krieger, N., et al., "Enhancement of Hepatitis C Virus RNA Replication by Cell Culture-Adaptive Mutations", Journal of Virology, May 2001, pp. 4614-4624.
Liu, Y., et al. "Use of a Fluorescence Plate Reader for Measuring Kinetic Parameters with Inner Filter Effect Correction", Analytical Biochemistry 267, pp. 331-335 (1999).
Lohmann, V., et al., "Replication of Subgenomic Hepatitis C Virus RNAs in a Hepatoma Cell Line", Science 285, 1999, pp. 110-113.
Miller, S., et al., "Application of Ring-Closing Metathesis to the Synthesis of Rigidified Amino Acids and Peptides", J.Am. Chem. Soc. 1996, 118, p. 9606-9614.
Mitsunobu, O., et al. "The Use of Diethyl Azodicarboxylate and Triphenylphospine in Synthesis and Transformation of Natural Products", Synthesis, Jan. 1-28, 1981.
Olson, R., et al. "Orally Active Isoxazoline Glycoprotein IIB/IIIa Antagnoists with Extended Duratioan of Action", J. Med. Chem. 1999, 42, pp. 1178-1192.
Poliakov, "Expression and Purification of Recombinant Full-Length NS3 Protease-Helicase from a New Variant of Hepatitis C Virus", Prot Expression & Purification, 25, pp. 363-371, 2002.
Richter, L. et al, "A Surprising Observation about Mitsunobu Reactions in Solid Phase Synthesis", Tetrahedron Letters, vol. 35, No. 27, p. 4705-4706, 1994.
Rosenquist, et al., "Synthesis of Enantiomerically Pure trans-3,4-Substituted Cyclopentanois by Enzymatic Resolution", Acta Chem. Scand. 46 (1992) 1127-1129.
Smith, E.M., et al., "Synthesis and Pharmacological Activity of Anagiotensin converting Enzyme Inhibitors: N-(Mercaptoacy)-4-substituted-(S)-Prolines", J. Med. Chem. (1988), 31, 875-885.
Tozer, M., et al. "4-Chlorobenzyl Sulfonamide and Sulfamide Derivatives of Histamine Homologues: The Design of Potent Histamine H, Receptor Antagonists", Bioorganic & Medicinal Chemistry Letters 9 (1999) 3103-3108.
Hirao et al., "Preparation of Optically Active 8,8'-Disubstituted 1,1' Bisoquinoline", Heterocycle, vol. 42(1), pp. 415-422 (1996).
Landro et al., "Mechanistic Role of an NS4A Peptide Cofactor with the Truncated NS3 Protease of Hepatitis C Virus Elucidation of the NS4A Stimulatory Effect via Kinetic Analysis and Inhibitor Mapping", Biochemistry, vol. 36, pp. 9340-9348 (1997).
Rano et al., "Graphical Abstracts", Tetrahedron Letters, vol. 36 (22), pp. 3779-3792 (1995).
Vippagunta, et al., "Crystalline Solids", Advanced Drug Delivery Reviews, vol. 48, pp. 3-26, (2001).

* cited by examiner

MACROCYCLIC INHIBITORS OF HEPATITIS C VIRUS

CROSS REFERENCE TO RELATED APPLICATIONS

This application claims priority of the benefits of patent Application Nos. EP05107073.8 filed Jul. 29, 2005; EP 05107416.9 filed Aug. 11, 2005; and PCT Application No PCT/EP2006/064819 filed Jul. 28, 2006. The complete disclosures of the aforementioned related patent applications are hereby incorporated herein by reference for all purposes.

The present invention is concerned with macrocylic compounds having inhibitory activity on the replication of the hepatitis C virus (HCV). It further concerns compositions comprising these compounds as active ingredients as well as processes for preparing these compounds and compositions.

Hepatitis C virus is the leading cause of chronic liver disease worldwide and has become a focus of considerable medical research. HCV is a member of the Flaviviridae family of viruses in the hepacivirus genus, and is closely related to the flavivirus genus, which includes a number of viruses implicated in human disease, such as dengue virus and yellow fever virus, and to the animal pestivirus family, which includes bovine viral diarrhea virus (BVDV). HCV is a positive-sense, single-stranded RNA virus, with a genome of around 9,600 bases. The genome comprises both 5' and 3' untranslated regions which adopt RNA secondary structures, and a central open reading frame that encodes a single polyprotein of around 3,010-3,030 amino acids. The polyprotein encodes ten gene products which are generated from the precursor polyprotein by an orchestrated series of co- and posttranslational endoproteolytic cleavages mediated by both host and viral proteases. The viral structural proteins include the core nucleocapsid protein, and two envelope glycoproteins E1 and E2. The non-structural (NS) proteins encode some essential viral enzymatic functions (helicase, polymerase, protease), as well as proteins of unknown function. Replication of the viral genome is mediated by an RNA-dependent RNA polymerase, encoded by non-structural protein 5 b (NS5B). In addition to the polymerase, the viral helicase and protease functions, both encoded in the bifunctional NS3 protein, have been shown to be essential for replication of HCV RNA. In addition to the NS3 serine protease, HCV also encodes a metalloproteinase in the NS2 region.

Following the initial acute infection, a majority of infected individuals develop chronic hepatitis because HCV replicates preferentially in hepatocytes but is not directly cytopathic. In particular, the lack of a vigorous T-lymphocyte response and the high propensity of the virus to mutate appear to promote a high rate of chronic infection. Chronic hepatitis can progress to liver fibrosis leading to cirrhosis, end-stage liver disease, and HCC (hepatocellular carcinoma), making it the leading cause of liver transplantations.

There are 6 major HCV genotypes and more than 50 subtypes, which are differently distributed geographically. HCV type 1 is the predominant genotype in Europe and the US. The extensive genetic heterogeneity of HCV has important diagnostic and clinical implications, perhaps explaining difficulties in vaccine development and the lack of response to therapy.

Transmission of HCV can occur through contact with contaminated blood or blood products, for example following blood transfusion or intravenous drug use. The introduction of diagnostic tests used in blood screening has led to a downward trend in post-transfusion HCV incidence. However, given the slow progression to the end-stage liver disease, the existing infections will continue to present a serious medical and economic burden for decades.

Current HCV therapies are based on (pegylated) interferon-alpha (IFN-α) in combination with ribavirin. This combination therapy yields a sustained virologic response in more than 40% of patients infected by genotype 1 viruses and about 80% of those infected by genotypes 2 and 3. Beside the limited efficacy on HCV type 1, this combination therapy has significant side effects and is poorly tolerated in many patients. Major side effects include influenza-like symptoms, hematologic abnormalities, and neuropsychiatric symptoms. Hence there is a need for more effective, convenient and better tolerated treatments.

Recently, two peptidomimetic HCV protease inhibitors have gained attention as clinical candidates, namely BILN-2061 disclosed in WO00/59929 and VX-950 disclosed in WO03/87092. A number of similar HCV protease inhibitors have also been disclosed in the academic and patent literature. It has already become apparent that the sustained administration of BILN-2061 or VX-950 selects HCV mutants which are resistant to the respective drug, so called drug escape mutants. These drug escape mutants have characteristic mutations in the HCV protease genome, notably D168V, D168A and/or A156S. Accordingly, additional drugs with different resistance patterns are required to provide failing patients with treatment options, and combination therapy with multiple drugs is likely to be the norm in the future, even for first line treatment.

Experience with HIV drugs, and HIV protease inhibitors in particular, has further emphasized that sub-optimal pharmacokinetics and complex dosage regimes quickly result in inadvertent compliance failures. This in turn means that the 24 hour trough concentration (minimum plasma concentration) for the respective drugs in an HIV regime frequently falls below the $IC_{90}$ or $ED_{90}$ threshold for large parts of the day. It is considered that a 24 hour trough level of at least the $IC_{50}$, and more realistically, the $IC_{90}$ or $ED_{90}$, is essential to slow down the development of drug escape mutants. Achieving the necessary pharmacokinetics and drug metabolism to allow such trough levels provides a stringent challenge to drug design. The strong peptidomimetic nature of prior art HCV protease inhibitors, with multiple peptide bonds poses pharmacokinetic hurdles to effective dosage regimes.

There is a need for HCV inhibitors which may overcome the disadvantages of current HCV therapy such as side effects, limited efficacy, the emerging of resistance, and compliance failures.

WO05/010029 discloses aza-peptide macrocyclic Hepatitis C serine protease inhibitors, pharmaceutical compositions comprising the aforementioned compounds for administration to a subject suffering from HCV infection, and methods of treating an HCV infection in a subject by administering a pharmaceutical composition comprising the said compounds.

The present invention concerns inhibitors of HCV replication which are pharmacological acceptable alternatives to the current HCV inhibitors. The compounds of the present invention have relatively low molecular weight and are easy to synthesize, starting from starting materials that are commercially available or readily available through art-known synthesis procedures.

The present invention concerns inhibitors of HCV replication, which can be represented by formula (I):

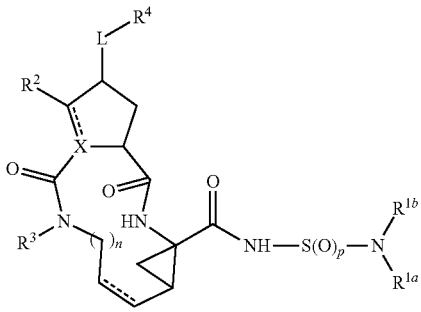

and the N-oxides, salts, and stereoisomers thereof, wherein
each dashed line (represented by - - -) represents an optional double bond;
X is N, CH and where X bears a double bond it is C;
$R^{1a}$ and $R^{1b}$ are, independently, hydrogen, $C_{3-7}$cycloalkyl, aryl, Het, $C_{1-6}$alkoxy, $C_{1-6}$alkyl optionally substituted with halo, $C_{1-6}$alkoxy, cyano, polyhalo$C_{1-6}$alkoxy, $C_{3-7}$cycloalkyl, aryl, or with Het; or $R^{1a}$ and $R^{1b}$ together with the nitrogen to which they are attached form a 4 to 6 membered saturated, partially unsaturated or completely unsaturated heterocyclic ring optionally containing additional 1 to 3 heteroatoms each independently selected from nitrogen, oxygen and sulfur, and wherein said heterocyclic ring may be optionally substituted with one or two substituents each independently selected from the group consisting of halo, $C_{1-6}$alkyl, polyhalo$C_{1-6}$alkyl, hydroxy, $C_{1-6}$alkoxy, polyhalo$C_{1-6}$alkoxy, $C_{1-6}$alkoxy$C_{1-6}$alkyl, carboxyl, $C_{1-6}$alkylcarbonyl, cyano, mono- and di$C_{1-6}$alkylamino, aryl and aryl$C_{1-6}$alkyl;
L is a direct bond, —O—, —O—$C_{1-4}$alkanediyl-, —O—CO—, —O—C(=O)—NR$^{5a}$— or —O—C(=O)—NR$^{5a}$—$C_{1-4}$alkanediyl-;
$R^2$ is hydrogen, and where X is C or CH, $R^2$ may also be $C_{1-6}$alkyl;
$R^3$ is hydrogen, $C_{1-6}$alkyl, $C_{1-6}$alkoxy$C_{1-6}$alkyl, $C_{3-7}$cycloalkyl, amino, mono- or di$C_{1-6}$alkylamino;
$R^4$ is aryl or a saturated, a partially unsaturated or completely unsaturated 5 or 6 membered monocyclic or 9 to 12 membered bicyclic heterocyclic ring system wherein said ring system contains one nitrogen, and optionally one to three additional heteroatoms selected from the group consisting of oxygen, sulfur and nitrogen, and wherein the remaining ring members are carbon atoms; wherein said ring system may be optionally substituted on any carbon or nitrogen ring atom with one, two, three, or four substituents each independently selected from $C_{3-7}$cycloalkyl, aryl, Het, —C(=O)NR$^{5a}$R$^{5b}$, —C(=O)R$^7$, —C(=O)OR$^{6a}$, and $C_{1-6}$alkyl optionally substituted with $C_{3-7}$cycloalkyl, aryl, Het, —C(=O)NR$^{5a}$R$^{5b}$, —NR$^{5a}$R$^{5b}$, —C(=O)R$^7$, —NR$^{5a}$C(=O)R$^7$, —NR$^{5a}$SO$_p$R$^8$, —SO$_p$R$^8$, —SO$_p$NR$^{5a}$R$^{5b}$, —C(=O)OR$^6$, or —NR$^{5a}$C(=O)OR$^{6a}$;
and wherein the substituents on any carbon atom of the heterocyclic ring may also be selected from $C_{1-6}$alkoxy, hydroxy, halo, polyhalo-$C_{1-6}$alkyl, $C_{1-6}$alkylthio, oxo, cyano, nitro, azido, —NR$^{5a}$R$^{5b}$, —NR$^{5a}$C(=O)R$^7$, —NR$^{5a}$SO$_p$R$^8$, —SO$_p$R$^8$, —SO$_p$NR$^{5a}$R$^{5b}$, —C(=O)OH, and —NR$^{5a}$C(=O)OR$^{6a}$;
n is 3, 4, 5, or 6;
p is 1 or 2;

each $R^{5a}$ and $R^{5b}$ are, independently, hydrogen, $C_{3-7}$cycloalkyl, aryl, Het, $C_{1-6}$alkyl optionally substituted with halo, $C_{1-6}$alkoxy, cyano, polyhalo$C_{1-6}$alkoxy, $C_{3-7}$cycloalkyl, aryl, or with Het;
$R^6$ is hydrogen, $C_{2-6}$alkenyl, $C_{3-7}$cycloalkyl, Het, or $C_{1-6}$alkyl optionally substituted with $C_{3-7}$cycloalkyl, aryl or Het;
$R^{6a}$ is $C_{2-6}$alkenyl, $C_{3-7}$cycloalkyl, Het, or $C_{1-6}$alkyl optionally substituted with $C_{3-7}$cycloalkyl, aryl or Het;
$R^7$ is hydrogen, $C_{1-6}$alkyl, $C_{3-7}$cycloalkyl, or aryl;
$R^8$ is hydrogen, polyhalo$C_{1-6}$alkyl, $C_{3-7}$cycloalkyl, aryl, Het, or $C_{1-6}$alkyl optionally substituted with $C_{3-7}$cycloalkyl, aryl or Het;
aryl as a group or part of a group is phenyl, naphthyl, indanyl, or 1,2,3,4-tetra-hydronaphthyl, each of which may be optionally substituted with one, two or three substituents selected from halo, $C_{1-6}$alkyl, polyhalo$C_{1-6}$alkyl, hydroxy, $C_{1-6}$alkoxy, polyhalo$C_{1-6}$alkoxy, $C_{1-6}$alkoxy$C_{1-6}$alkyl, carboxyl, $C_{1-6}$alkylcarbonyl, $C_{1-6}$alkoxy-carbonyl, cyano, nitro, amino, mono- or di$C_{1-6}$alkylamino, aminocarbonyl, mono- or di$C_{1-6}$alkylaminocarbonyl, azido, mercapto, $C_{3-7}$cycloalkyl, phenyl, pyridyl, thiazolyl, pyrazolyl, pyrrolidinyl, piperidinyl, piperazinyl, 4-$C_{1-6}$alkylpiperazinyl, 4-$C_{1-6}$alkylcarbonyl-piperazinyl, and morpholinyl; wherein the morpholinyl and piperidinyl groups may be optionally substituted with one or with two $C_{1-6}$alkyl radicals; and the phenyl, pyridyl, thiazolyl, pyrazolyl groups may be optionally substituted with 1, 2 or 3 substituents each independently selected from $C_{1-6}$alkyl, $C_{1-6}$alkoxy, halo, amino, mono- or di$C_{1-6}$alkylamino;
Het as a group or part of a group is a 5 or 6 membered saturated, partially unsaturated or completely unsaturated heterocyclic ring containing 1 to 4 heteroatoms each independently selected from nitrogen, oxygen and sulfur, being optionally condensed with a benzene ring, and wherein the group Het as a whole may be optionally substituted with one, two or three substituents each independently selected from the group consisting of halo, $C_{1-6}$alkyl, polyhalo$C_{1-6}$alkyl, hydroxy, $C_{1-6}$alkoxy, polyhalo$C_{1-6}$alkoxy, $C_{1-6}$alkoxy$C_{1-6}$alkyl, carboxyl, $C_{1-6}$alkylcarbonyl, $C_{1-6}$alkoxycarbonyl, cyano, nitro, amino, mono- or di$C_{1-6}$alkylamino, amino-carbonyl, mono- or di$C_{1-6}$alkylaminocarbonyl, $C_{3-7}$cycloalkyl, phenyl, pyridyl, thiazolyl, pyrazolyl, pyrrolidinyl, piperidinyl, piperazinyl, 4-$C_{1-6}$alkylpiperazinyl, 4-$C_{1-6}$alkylcarbonyl-piperazinyl, and morpholinyl; wherein the morpholinyl and piperidinyl groups may be optionally substituted with one or with two $C_{1-6}$alkyl radicals; and the phenyl, pyridyl, thiazolyl, pyrazolyl groups may be optionally substituted with 1, 2 or 3 substituents each independently selected from $C_{1-6}$alkyl, $C_{1-6}$alkoxy, halo, amino, mono- or di$C_{1-6}$alkylamino.

The invention further relates to methods for the preparation of the compounds of formula (I), the N-oxides, addition salts, quaternary amines, metal complexes, and stereochemically isomeric forms thereof, their intermediates, and the use of the intermediates in the preparation of the compounds of formula (I).

The invention relates to the compounds of formula (I) per se, the N-oxides, addition salts, quaternary amines, metal complexes, and stereochemically isomeric forms thereof, for use as a medicament. The invention further relates to pharmaceutical compositions comprising the aforementioned compounds for administration to a subject suffering from HCV infection. The pharmaceutical compositions may comprise combinations of the aforementioned compounds with other anti-HCV agents.

The invention also relates to the use of a compound of formula (I), or a N-oxide, addition salt, quaternary amine, metal complex, or stereochemically isomeric forms thereof, for the manufacture of a medicament for inhibiting HCV replication. Or the invention relates to a method of inhibiting HCV replication in a warm-blooded animal said method comprising the administration of an effective amount of a compound of formula (I), or a N-oxide, addition salt, quaternary amine, metal complex, or stereochemically isomeric forms thereof.

As used in the foregoing and hereinafter, the following definitions apply unless otherwise noted.

The term halo is generic to fluoro, chloro, bromo and iodo.

The term "polyhalo$C_{1-6}$alkyl" as a group or part of a group, e.g. in polyhalo$C_{1-6}$alkoxy, is defined as mono- or polyhalo substituted $C_{1-6}$alkyl, in particular $C_{1-6}$alkyl substituted with up to one, two, three, four, five, six, or more halo atoms, such as methyl or ethyl with one or more fluoro atoms, for example, difluoromethyl, trifluoromethyl, trifluoro-ethyl. Preferred is trifluoromethyl. Also included are perfluoro$C_{1-6}$alkyl groups, which are $C_{1-6}$alkyl groups wherein all hydrogen atoms are replaced by fluoro atoms, e.g. pentafluoroethyl. In case more than one halogen atom is attached to an alkyl group within the definition of polyhalo$C_{1-6}$alkyl, the halogen atoms may be the same or different.

As used herein "$C_{1-4}$alkyl" as a group or part of a group defines straight or branched chain saturated hydrocarbon radicals having from 1 to 4 carbon atoms such as for example methyl, ethyl, 1-propyl, 2-propyl, 1-butyl, 2-butyl, 2-methyl-1-propyl; "$C_{1-6}$alkyl" encompasses $C_{1-4}$alkyl radicals and the higher homologues thereof having 5 or 6 carbon atoms such as, for example, 1-pentyl, 2-pentyl, 3-pentyl, 1-hexyl, 2hexyl, 2-methyl-1-butyl, 2-methyl-1-pentyl, 2-ethyl-1-butyl, 3-methyl-2-pentyl, and the like. Of interest amongst $C_{1-6}$alkyl is $C_{1-4}$alkyl.

The term "$C_{2-6}$alkenyl" as a group or part of a group defines straight and branched chained hydrocarbon radicals having saturated carbon-carbon bonds and at least one double bond, and having from 2 to 6 carbon atoms, such as, for example, ethenyl (or vinyl), 1-propenyl, 2-propenyl (or allyl), 1-butenyl, 2-butenyl, 3-butenyl, 2-methyl-2-propenyl, 2-pentenyl, 3-pentenyl, 2-hexenyl, 3-hexenyl, 4-hexenyl, 2-methyl-2-butenyl, 2-methyl-2-pentenyl and the like. Of interest amongst $C_{2-6}$alkenyl is $C_{2-4}$alkenyl.

The term "$C_{2-6}$alkynyl" as a group or part of a group defines straight and branched chained hydrocarbon radicals having saturated carbon-carbon bonds and at least one triple bond, and having from 2 to 6 carbon atoms, such as, for example, ethynyl, 1-propynyl, 2-propynyl, 1-butynyl, 2-butynyl, 3-butynyl, 2-pentynyl, 3-pentynyl, 2-hexynyl, 3-hexynyl and the like. Of interest amongst $C_{2-6}$alkynyl is $C_{2-4}$alkynyl.

$C_{3-7}$cycloalkyl is generic to cyclopropyl, cyclobutyl, cyclopentyl, cyclohexyl and cycloheptyl.

$C_{1-6}$ alkanediyl defines bivalent straight and branched chain saturated hydrocarbon radicals having from 1 to 6 carbon atoms such as, for example, methylene, ethylene, 1,3-propanediyl, 1,4-butanediyl, 1,2-propanediyl, 2,3-butanediyl, 1,5-pentanediyl, 1,6-hexanediyl and the like. Of interest amongst $C_{1-6}$ alkanediyl is $C_{1-4}$alkanediyl.

$C_{1-6}$alkoxy means $C_{1-6}$alkoxy wherein $C_{1-6}$alkyl is as defined above.

As used herein before, the term (=O) or oxo forms a carbonyl moiety when attached to a carbon atom, a sulfoxide moiety when attached to a sulfur atom and a sulfonyl moiety when two of said terms are attached to a sulfur atom. Whenever a ring or ring system is substituted with an oxo group, the carbon atom to which the oxo is linked is a staturated carbon.

The radical Het is a heterocycle as specified in this specification and claims. Examples of Het comprise, for example, pyrrolidinyl, piperidinyl, morpholinyl, piperazinyl, pyrrolyl, imidazolyl, oxazolyl, isoxazolyl, thiazinolyl, isothiazinolyl, thiazolyl, isothiazolyl, oxadiazolyl, thiadiazolyl, triazolyl (including 1,2,3-triazolyl, 1,2,4-triazolyl), tetrazolyl, furanyl, thienyl, pyridyl, pyrimidyl, pyridazinyl, pyrazolyl, triazinyl, and the like. Of interest amongst the Het radicals are those which are non-saturated, in particular those having an aromatic character. Of further interest are those Het radicals having one or two nitrogens.

Each of the Het radicals mentioned in this and the following paragraph may be optionally substituted with the number and kind of substituents mentioned in the definitions of the compounds of formula (I) or any of the subgroups of compounds of formula (I). Some of the Het radicals mentioned in this and the following paragraph may be substituted with one, two or three hydroxy substituents. Such hydroxy substituted rings may occur as their tautomeric forms bearing keto groups. For example a 3-hydroxypyridazine moiety can occur in its tautomeric form 2H-pyridazin-3-one. Where Het is piperazinyl, it preferably is substituted in its 4-position by a substituent linked to the 4-nitrogen with a carbon atom, e.g. 4-$C_{1-6}$alkyl, 4-polyhalo-$C_{1-6}$alkyl, $C_{1-6}$alkoxy$C_{1-6}$alkyl, $C_{1-6}$alkylcarbonyl, $C_{3-7}$cycloalkyl.

Interesting Het radicals comprise, for example pyrrolidinyl, piperidinyl, morpholinyl, piperazinyl, pyrrolyl, pyrazolyl, imidazolyl, oxazolyl, isoxazolyl, thiazolyl, isothiazolyl, oxadiazolyl, thiadiazolyl, triazolyl (including 1,2,3-triazolyl, 1,2,4-triazolyl), tetrazolyl, furanyl, thienyl, pyridyl, pyrimidyl, pyridazinyl, pyrazolyl, triazinyl, or any of such heterocycles condensed with a benzene ring, such as indolyl, indazolyl (in particular 1H-indazolyl), indolinyl, quinolinyl, tetrahydroquinolinyl (in particular 1,2,3,4-tetrahydroquinolinyl), isoquinolinyl, tetrahydroisoquinolinyl (in particular 1,2,3,4-tetrahydroisoquinolinyl), quinazolinyl, phthalazinyl, benzimidazolyl, benzoxazolyl, benzisoxazolyl, benzothiazolyl, benzoxadiazolyl, benzothiadiazolyl, benzofuranyl, benzothienyl.

The Het radicals pyrrolidinyl, piperidinyl, morpholinyl, piperazinyl, 4-substituted piperazinyl preferably are linked via their nitrogen atom (i.e. 1-pyrrolidinyl, 1-piperidinyl, 4-morpholinyl, 1-piperazinyl, 4-substituted 1-piperazinyl).

$R^{1a}$ and $R^{1b}$ together with the nitrogen to which they are attached form a 4 to 6 membered saturated, partially unsaturated or completely unsaturated heterocyclic ring as specified above. Examples of such rings are any of the heterocycles mentioned in the previous paragraphs that have a nitrogen atom through which the ring can be linked to the remainder of the molecule. Particular examples of such rings are pyrrolidinyl, piperidinyl, morpholinyl, piperazinyl, 4-substituted piperazinyl.

Each "aryl" is as specified above and preferably is phenyl substituted with the substituents specified above. This applies equally to aryl$C_{1-6}$alkyl, which in particular can be arylmethyl, e.g. benzyl.

It should be noted that the radical positions on any molecular moiety used in the definitions may be anywhere on such moiety as long as it is chemically stable.

Radicals used in the definitions of the variables include all possible isomers unless otherwise indicated. For instance pyridyl includes 2-pyridyl, 3-pyridyl and 4-pyridyl; pentyl includes 1-pentyl, 2-pentyl and 3-pentyl.

When any variable occurs more than one time in any constituent, each definition is independent.

Whenever used hereinafter, the term "compounds of formula (I)", or "the present compounds" or similar terms, it is meant to include the compounds of formula (I), each and any of the subgroups thereof, their N-oxides, addition salts, quaternary amines, metal complexes, and stereochemically isomeric forms. One embodiment comprises the compounds of formula (I) or any subgroup of compounds of formula (I) specified herein, as well as the N-oxides, salts, as the possible stereoisomeric forms thereof. Another embodiment comprises the compounds of formula (I) or any subgroup of compounds of formula (I) specified herein, as well as the salts as the possible stereoisomeric forms thereof.

The compounds of formula (I) have several centers of chirality and exist as stereochemically isomeric forms. The term "stereochemically isomeric forms" as used herein defines all the possible compounds made up of the same atoms bonded by the same sequence of bonds but having different three-dimensional structures which are not interchangeable, which the compounds of formula (I) may possess.

With reference to the instances where (R) or (S) is used to designate the absolute configuration of a chiral atom within a substituent, the designation is done taking into consideration the whole compound and not the substituent in isolation.

Unless otherwise mentioned or indicated, the chemical designation of a compound encompasses the mixture of all possible stereochemically isomeric forms, which said compound may possess. Said mixture may contain all diastereomers and/or enantiomers of the basic molecular structure of said compound. All stereochemically isomeric forms of the compounds of the present invention both in pure form or mixed with each other are intended to be embraced within the scope of the present invention.

Pure stereoisomeric forms of the compounds and intermediates as mentioned herein are defined as isomers substantially free of other enantiomeric or diastereomeric forms of the same basic molecular structure of said compounds or intermediates. In particular, the term "stereoisomerically pure" concerns compounds or intermediates having a stereoisomeric excess of at least 80% (i.e. minimum 90% of one isomer and maximum 10% of the other possible isomers) up to a stereoisomeric excess of 100% (i.e. 100% of one isomer and none of the other), more in particular, compounds or intermediates having a stereoisomeric excess of 90% up to 100%, even more in particular having a stereoisomeric excess of 94% up to 100% and most in particular having a stereoisomeric excess of 97% up to 100%. The terms "enantiomerically pure" and "diastereomerically pure" should be understood in a similar way, but then having regard to the enantiomeric excess, and the diastereomeric excess, respectively, of the mixture in question.

Pure stereoisomeric forms of the compounds and intermediates of this invention may be obtained by the application of art-known procedures. For instance, enantiomers may be separated from each other by the selective crystallization of their diastereomeric salts with optically active acids or bases. Examples thereof are tartaric acid, dibenzoyltartaric acid, ditoluoyltartaric acid and camphosulfonic acid. Alternatively, enantiomers may be separated by chromatographic techniques using chiral stationary phases. Said pure stereochemically isomeric forms may also be derived from the corresponding pure stereochemically isomeric forms of the appropriate starting materials, provided that the reaction occurs stereospecifically. Preferably, if a specific stereoisomer is desired, said compound is synthesized by stereospecific methods of preparation. These methods will advantageously employ enantiomerically pure starting materials.

The diastereomeric racemates of the compounds of formula (I) can be obtained separately by conventional methods. Appropriate physical separation methods that may advantageously be employed are, for example, selective crystallization and chromatography, e.g. column chromatography.

For some of the compounds of formula (I), their prodrugs, N-oxides, salts, solvates, quaternary amines, or metal complexes, and the intermediates used in the preparation thereof, the absolute stereochemical configuration was not experimentally determined. A person skilled in the art is able to determine the absolute configuration of such compounds using art-known methods such as, for example, X-ray diffraction.

The present invention is also intended to include all isotopes of atoms occurring on the present compounds. Isotopes include those atoms having the same atomic number but different mass numbers. By way of general example and without limitation, isotopes of hydrogen include tritium and deuterium. Isotopes of carbon include C-13 and C-14.

The term "prodrug" as used throughout this text means the pharmacologically acceptable derivatives such as esters, amides and phosphates, such that the resulting in vivo biotransformation product of the derivative is the active drug as defined in the compounds of formula (I). The reference by Goodman and Gilman (The Pharmacological Basis of Therapeutics, $8^{th}$ ed, McGraw-Hill, Int. Ed. 1992, "Biotransformation of Drugs", p 13-15) describing prodrugs generally is hereby incorporated. Prodrugs preferably have excellent aqueous solubility, increased bioavailability and are readily metabolized into the active inhibitors in vivo. Prodrugs of a compound of the present invention may be prepared by modifying functional groups present in the compound in such a way that the modifications are cleaved, either by routine manipulation or in vivo, to the parent compound.

Preferred are pharmaceutically acceptable ester prodrugs that are hydrolysable in vivo and are derived from those compounds of formula (I) having a hydroxy or a carboxyl group. An in vivo hydrolysable ester is an ester, which is hydrolysed in the human or animal body to produce the parent acid or alcohol. Suitable pharmaceutically acceptable esters for carboxy include $C_{1-6}$alkoxymethyl esters for example methoxy-methyl, $C_{1-6}$alkanoyloxymethyl esters for example pivaloyloxymethyl, phthalidyl esters, $C_{3-8}$cycloalkoxycarbonyloxy$C_{1-6}$alkyl esters for example 1-cyclohexylcarbonyloxyethyl; 1,3-dioxolen-2-onylmethyl esters for example 5-methyl-1,3-dioxolen-2-onylmethyl; and $C_{1-6}$alkoxycarbonyloxyethyl esters for example 1-methoxycarbonyl-oxyethyl which may be formed at any carboxy group in the compounds of this invention.

An in vivo hydrolysable ester of a compound of the formula (I) containing a hydroxy group includes inorganic esters such as phosphate esters and α-acyloxyalkyl ethers and related compounds which as a result of the in vivo hydrolysis of the ester breakdown to give the parent hydroxy group. Examples of α-acyloxyalkyl ethers include acetoxy-methoxy and 2,2-dimethylpropionyloxy-methoxy. A selection of in vivo hydrolysable ester forming groups for hydroxy include alkanoyl, benzoyl, phenylacetyl and substituted benzoyl and phenylacetyl, alkoxycarbonyl (to give alkyl carbonate esters), dialkylcarbamoyl and N-(dialkylaminoethyl)-N-alkylcarbamoyl (to give carbamates), dialkylaminoacetyl and carboxyacetyl. Examples of substituents on benzoyl include morpholino and piperazino linked from a ring nitrogen atom via a methylene group to the 3- or 4-position of the benzoyl ring.

For therapeutic use, salts of the compounds of formula (I) are those wherein the counter-ion is pharmaceutically acceptable. However, salts of acids and bases which are non-pharmaceutically acceptable may also find use, for example, in the preparation or purification of a pharmaceutically acceptable compound. All salts, whether pharmaceutically acceptable or not are included within the ambit of the present invention.

The pharmaceutically acceptable acid and base addition salts as mentioned hereinabove are meant to comprise the therapeutically active non-toxic acid and base addition salt forms which the compounds of formula (I) are able to form. The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic (i.e. hydroxybutanedioic acid), tartaric, citric, methanesulfonic, ethanesulfonic, benzenesulfonic, p-toluenesulfonic, cyclamic, salicylic, p-aminosalicylic, pamoic and the like acids.

Conversely said salt forms can be converted by treatment with an appropriate base into the free base form.

The compounds of formula (I) containing an acidic proton may also be converted into their non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like.

The term addition salt as used hereinabove also comprises the solvates which the compounds of formula (I) as well as the salts thereof, are able to form. Such solvates are for example hydrates, alcoholates and the like.

The term "quaternary amine" as used hereinbefore defines the quaternary ammonium salts which the compounds of formula (I) are able to form by reaction between a basic nitrogen of a compound of formula (I) and an appropriate quaternizing agent, such as, for example, an optionally substituted alkylhalide, arylhalide or arylalkylhalide, e.g. methyliodide or benzyliodide. Other reactants with good leaving groups may also be used, such as alkyl trifluoromethanesulfonates, alkyl methanesulfonates, and alkyl p-toluenesulfonates. A quaternary amine has a positive charged nitrogen. Pharmaceutically acceptable counterions include chloro, bromo, iodo, trifluoroacetate and acetate. The counterion of choice can be introduced using ion exchange resins.

The N-oxide forms of the present compounds are meant to comprise the compounds of formula (I) wherein one or several nitrogen atoms are oxidized to the so-called N-oxide.

It will be appreciated that the compounds of formula (I) may have metal binding, chelating, complex forming properties and therefore may exist as metal complexes or metal chelates. Such metalated derivatives of the compounds of formula (I) are intended to be included within the scope of the present invention.

Some of the compounds of formula (I) may also exist in their tautomeric form. Such forms although not explicitly indicated in the above formula are intended to be included within the scope of the present invention.

As mentioned above, the compounds of formula (I) have several asymmetric centers. In order to more efficiently refer to each of these asymmetric centers, the numbering system as indicated in the following structural formula will be used.

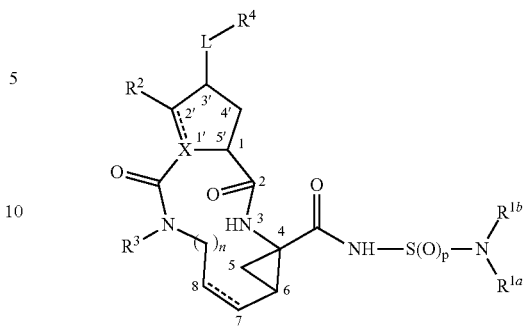

Asymmetric centers are present at positions 1, 4 and 6 of the macrocycle as well as at the carbon atom 3' in the 5-membered ring, carbon atom 2' when the $R^2$ substituent is $C_{1-6}$alkyl, and at carbon atom 1' when X is CH. Each of these asymmetric centers can occur in their R or S configuration.

The stereochemistry at position 1 preferably corresponds to that of an L-amino acid configuration, i.e. that of L-proline.

When X is CH, the 2 carbonyl groups substituted at positions 1' and 5' of the cyclopentane ring preferably are in a trans configuration. The carbonyl substituent at position 5' preferably is in that configuration that corresponds to an L-proline configuration. The carbonyl groups substituted at positions 1' and 5' preferably are as depicted below in the structure of the following formula

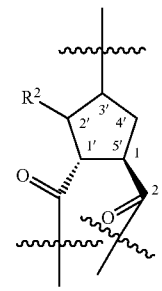

The compounds of formula (I) include a cyclopropyl group as represented in the structural fragment below:

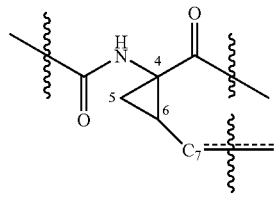

wherein $C_7$ represents the carbon at position 7 and carbons at position 4 and 6 are asymmetric carbon atoms of the cyclopropane ring.

Notwithstanding other possible asymmetric centers at other segments of the compounds of formula (I), the presence of these two asymmetric centers means that the compounds can exist as mixtures of diastereomers, such as the diastereomers of compounds of formula (I) wherein the carbon at position 7 is configured either syn to the carbonyl or syn to the amide as shown below.

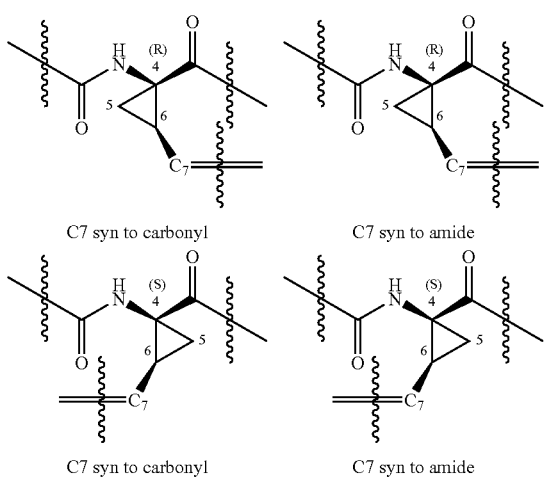

One embodiment concerns compounds of formula (I) wherein the carbon at position 7 is configured syn to the carbonyl. Another embodiment concerns compounds of formula (I) wherein the configuration at the carbon at position 4 is R. A specific subgroup of compounds of formula (I) are those wherein the carbon at position 7 is configured syn to the carbonyl and wherein the configuration at the carbon at position 4 is R.

The compounds of formula (I) may include a proline residue (when X is N) or a cyclopentyl or cyclopentenyl residue (when X is CH or C). Preferred are the compounds of formula (I) wherein the substituent at the 1 (or 5') position and the substituent -L-$R^4$ (at position 3') are in a trans configuration. Of particular interest are the compounds of formula (I) wherein position 1 has the configuration corresponding to L-proline and the -L-$R^4$ substituent is in a trans configuration in respect of position 1. Preferably the compounds of formula (I) have the stereochemistry as indicated in the structures of formulae (I-a) and (I-b) below:

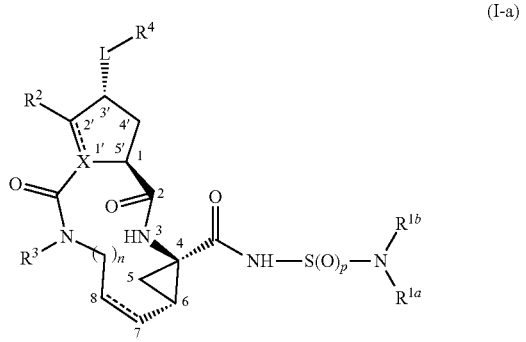

(I-a)

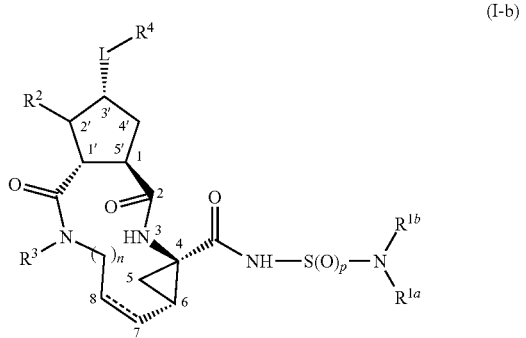

(I-b)

One embodiment of the present invention concerns compounds of formula (I) or of formula (I-a) or of any subgroup of compounds of formula (I), wherein one or more of the following conditions apply:

(a) $R^2$ is hydrogen;

(b) X is nitrogen;

(c) a double bond is present between carbon atoms 7 and 8.

One embodiment of the present invention concerns compounds of formula (I) or of formulae (I-a), (I-b), or of any subgroup of compounds of formula (I), wherein one or more of the following conditions apply:

(a) $R^2$ is hydrogen;

(b) X is CH;

(c) a double bond is present between carbon atoms 7 and 8.

Particular subgroups of compounds of formula (I) are those represented by the following structural formulae:

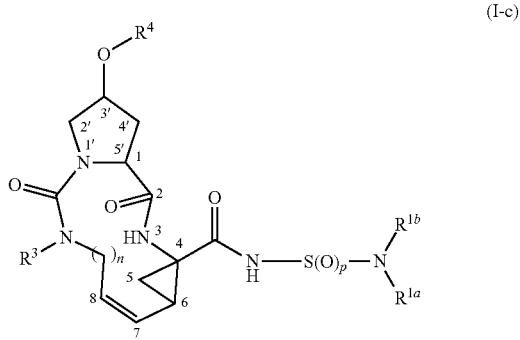

(I-c)

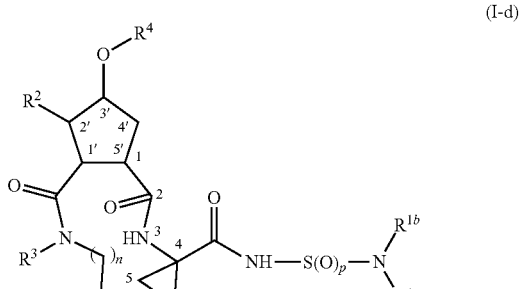

(I-d)

Amongst the compounds of formula (I-c) and (I-d), those having the stereochemical configuration of the compounds of formulae (I-a), and (I-b), respectively, are of particular interest.

The double bond between carbon atoms 7 and 8 in the compounds of formula (I), or in any subgroup of compounds of formula (I), may be in a cis or in a trans configuration. Preferably the double bond between carbon atoms 7 and 8 is in a cis configuration, as depicted in formulae (I-c) and (I-d).

A double bond between carbon atoms 1' and 2' may be present in the compounds of formula (I), or in any subgroup of compounds of formula (I), as depicted in formula (I-e) below

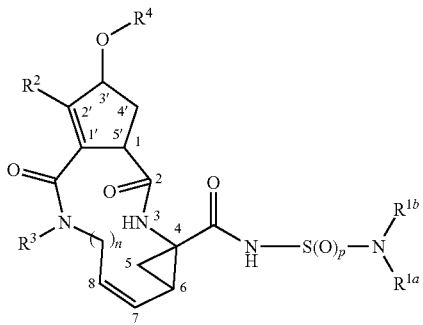

(I-e)

Yet another particular subgroup of compounds of formula (I) are those represented by the following structural formulae:

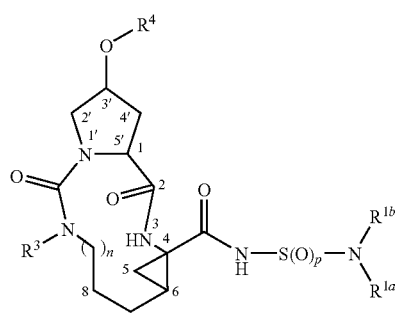

(I-f)

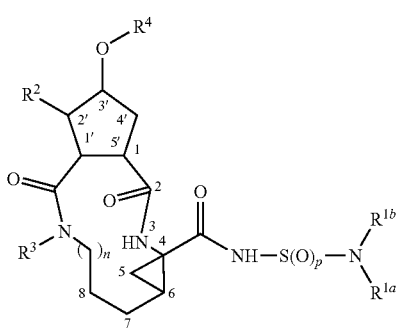

(I-g)

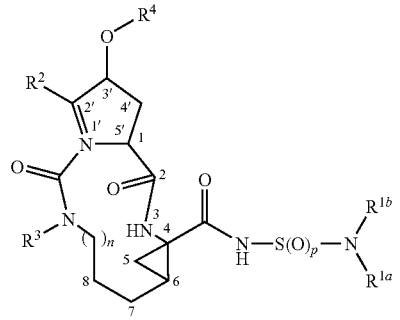

(I-h)

Amongst the compounds of formulae (I-f), (I-g) or (I-h), those having the stereo-chemical configuration of the compounds of formulae (I-a) and (I-b) are of particular interest.

In (I-a), (I-b), (I-c), (I-d), (I-e), (I-f), (I-g) and (I-h), where applicable, X, n, p, $R^{1a}$, $R^{1b}$, $R^2$, $R^3$, and $R^4$ are as specified in the definitions of the compounds of formula (I) or in any of the subgroups of compounds of formula (I) specified herein.

It is to be understood that the above defined subgroups of compounds of formulae (I-a), (I-b), (I-c), (I-d), (I-e), (I-f), (I-g) or (I-h), as well as any other subgroup defined herein, are meant to also comprise any N-oxides, addition salts, quaternary amines, metal complexes and stereochemically isomeric forms of such compounds.

When n is 2, the moiety —CH$_2$— bracketed by "n" corresponds to ethanediyl in the compounds of formula (I) or in any subgroup of compounds of formula (I). When n is 3, the moiety —CH$_2$— bracketed by "n" corresponds to propanediyl in the compounds of formula (I) or in any subgroup of compounds of formula (I). When n is 4, the moiety —CH$_2$— bracketed by "n" corresponds to butanediyl in the compounds of formula (I) or in any subgroup of compounds of formula (I). When n is 5, the moiety —CH$_2$-bracketed by "n" corresponds to pentanediyl in the compounds of formula (I) or in any subgroup of compounds of formula (I). When n is 6, the moiety —CH$_2$— bracketed by "n" corresponds to hexanediyl in the compounds of formula (I) or in any subgroup of compounds of formula (I). Particular subgroups of the compounds of formula (I) are those compounds wherein n is 4 or 5.

Embodiments of the invention are compounds of formula (I) or any of the subgroups of compounds of formula (I) wherein (a) each $R^{1a}$ and $R^{1b}$ are, independently, hydrogen, or $C_{1-6}$alkyl, such as methyl, ethyl, or tert-butyl, preferably at least one of $R^{1a}$ and $R^{1b}$ is $C_{1-6}$alkyl;

(b) one of $R^{1a}$ and $R^{1b}$ is $C_3$-$C_7$cycloalkyl, or aryl, e.g. wherein one of $R^{1a}$ and $R^{1b}$ is cyclopropyl, or phenyl;

(c) $R^{1a}$ and $R^{1b}$ together with the nitrogen to which they are attached form pyrrolidinyl, piperidinyl, piperazinyl, 4-$C_{1-6}$alkylpiperazinyl, 4-$C_{1-6}$alkylcarbonylpiperazinyl-piperazinyl, or morpholinyl.

Further embodiments of the invention are compounds of formula (I) or any of the subgroups of compounds of formula (I) wherein one of $R^{1a}$ and $R^{1b}$ is a Het group selected from

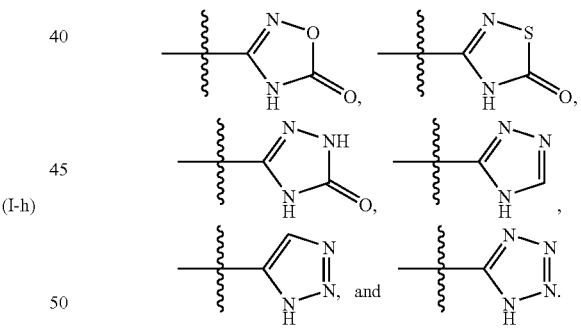

Further embodiments of the invention are compounds of formula (I) or any of the subgroups of compounds of formula (I) wherein (a) $R^2$ is hydrogen;

(b) $R^2$ is $C_{1-6}$alkyl, preferably methyl.

Embodiments of the invention are compounds of formula (I) or any of the subgroups of compounds of formula (I) wherein (a) X is N, C (X being linked via a double bond) or CH (X being linked via a single bond) and $R^2$ is hydrogen;

(b) X is C (X being linked via a double bond) and $R^2$ is $C_{1-6}$alkyl, preferably methyl.

(b) Further embodiments of the invention are compounds of formula (I) or any of the subgroups of compounds of formula (I) wherein (c) $R^3$ is hydrogen;
(d) $R^3$ is $C_{1-6}$alkyl;
(e) $R^3$ is amino, or mono- or di$C_{1-6}$alkylamino; or
(f) $R^3$ is $C_{1-6}$alkoxy$C_{1-6}$alkyl or $C_{3-7}$cycloalkyl.

Preferred embodiments of the invention are compounds of formula (I) or any of the subgroups of compounds of formula (I) wherein $R^3$ is hydrogen, $C_{1-6}$alkyl, amino, or mono- or di$C_{1-6}$alkylamino, more preferably $R^3$ is hydrogen, methyl, amino, or methylamino.

Further subgroups of the compounds of formula (I) are those compounds of formula (I), or any subgroup of compounds of formula (I) specified herein, wherein $R^4$ is phenyl, naphthyl, pyridyl, pyridazinyl, triazolyl, tetrazolyl, quinolinyl, isoquinolinyl, quinazolinyl, pyrimidinyl, [1,8]naphthyridinyl, indolinyl, 1,2,3,4-tetrahydroquinoline, 1,2,3,4-tetrahydroisoquinoline; all optionally substituted with one, two or three substituents selected from those mentioned in relation to $R^4$ in the definitions of the compounds of formula (I) or of any of the subgroups thereof.

Other subgroups of the compounds of formula (I) are those compounds of formula (I), or any subgroup of compounds of formula (I) specified herein, wherein (a) $R^4$ is phenyl, naphthyl (in particular naphth-1-yl, or naphth-2-yl), quinolinyl (in particular quinolin-4-yl), isoquinolinyl (in particular isoquinolin-1-yl), quinazolinyl (in particular quinazolin-4-yl), pyridyl (in particular 3-pyridyl), pyrimidinyl (in particular pyrimidin-4-yl), pyridazinyl (in particular pyridazin-3-yl and pyridazin-2-yl), [1,8]naphtyridinyl (in particular [1,8]naphthyridin-4-yl);
(b) $R^4$ is triazolyl (in particular triazol-1-yl, triazol-2-yl), tetrazolyl (in particular tetrazol-1-yl, tetrazol-2-yl), 6-oxopyridazin-1-yl, pyrazolyl (in particular pyrazol-1-yl), or imidazolyl (in particular imidazol-1-yl, imidazol-2-yl);
(c) $R^4$ is a heterocycle selected from

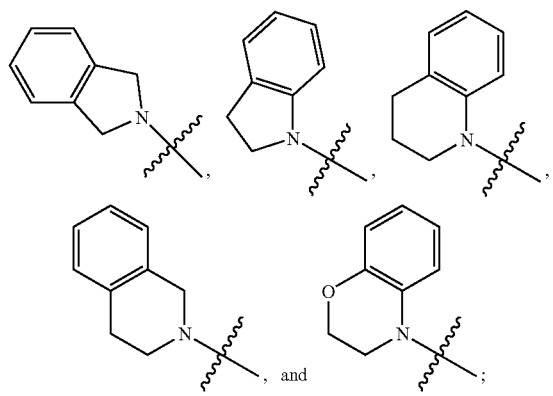

and wherein each of the above mentioned $R^4$ radicals may be optionally substituted with one, two or three substituents selected from those mentioned in relation to $R^4$ in the definitions of the compounds of formula (I) or any of the subgroups of compounds of formula (I).

Embodiments of the invention are compounds of formula (I) or any of the subgroups of compounds of formula (I) wherein L is a direct bond, —O—, —OC(=O)—, or —OC(=O)NR$^{5a}$—, or in particular wherein L is —OC(=O)NH— or —O—, or more in particular wherein L is —O—.

Preferably L is —O—, and $R^4$ is as specified above in (a). Preferably L is a direct bond, and $R^4$ is as specified above in (b). Preferably L is a bivalent radical —OC(=O)—, and $R^4$ is as specified above in (c).

Embodiments of the invention are compounds of formula (I) or any of the subgroups of compounds of formula (I) wherein L is —O— and $R^4$ is quinolinyl (in particular quinolin-4-yl), isoquinolinyl (in particular isoquinolin-1-yl), quinazolinyl (in particular quinazolin-4-yl), or pyrimidinyl (in particular pyrimidin-4-yl), either of which is, independently, optionally mono, di, or tri substituted with $C_{1-6}$alkyl, $C_{1-6}$alkoxy, nitro, hydroxy, halo, trifluoromethyl, —NR$^{5a}$R$^{5b}$, —C(=O)NR$^{5a}$R$^{5b}$, $C_{3-7}$cycloalkyl, aryl, Het, —C(=O)OH, or —C(=O)OR$^{6a}$; wherein aryl or Het are each, independently, optionally substituted with halo, $C_{1-6}$alkyl, $C_{1-6}$alkoxy, amino, mono- or di$C_{1-6}$alkylamino, pyrrolidinyl, piperidinyl, piperazinyl, 4-$C_{1-6}$alkylpiperazinyl (e.g. 4-methylpiperazinyl), or morpholinyl; and wherein the morpholinyl and piperidinyl groups may optionally substituted with one or two $C_{1-6}$alkyl radicals.

Embodiments of the invention are compounds of formula (I) or any of the subgroups of compounds of formula (I) wherein L is —O— and $R^4$ is quinolinyl (in particular quinolin-4-yl), isoquinolinyl (in particular isoquinolin-1-yl), quinazolinyl (in particular quinazolin-4-yl), or pyrimidinyl (in particular pyrimidin-4-yl), either of which is, independently, optionally mono, di, or tri substituted with methyl, ethyl, isopropyl, tert-butyl, methoxy, trifluoromethyl, trifluoromethoxy, fluoro, chloro, bromo, —NR$^{5a}$R$^{5b}$, —C(=O)NR$^{5a}$R$^{5b}$, phenyl, methoxyphenyl, cyanophenyl, halophenyl, pyridyl, $C_{1-4}$alkylpyridyl, pyrimidinyl, piperidinyl, morpholinyl, piperazinyl, $C_{1-4}$alkyl-piperazinyl, pyrrolidinyl, pyrazolyl, $C_{1-4}$alkyl-pyrazolyl, thiazolyl, $C_{1-4}$alkylthiazolyl, cyclopropylthiazolyl, or mono- or di$C_{1-4}$alkyl-aminothiazolyl; and wherein the morpholinyl, and piperidinyl groups may optionally substituted with one or two $C_{1-6}$alkyl (in particular one or two methyl) radicals.

Embodiments of the invention are compounds of formula (I) or any of the subgroups of compounds of formula (I) wherein $R^4$ is quinolinyl, optionally substituted with 1, 2, 3 or 4 (or with 1, 2 or 3) substituents selected from those mentioned as possible substituents on the monocyclic or bicyclic ring systems of $R^4$, as specified in the definitions of the compounds of formula (I) or of any of the subgroups of compounds of formula (I).

Specific embodiments of the invention are those compounds of formula (I) or any of the subgroups of compounds of formula (I) wherein $R^4$ is
(d-1) a radical of formula

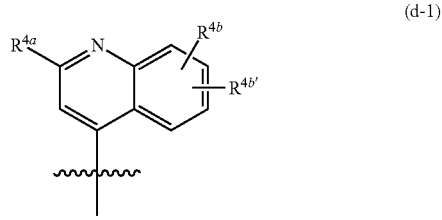

(d-1)

(d-2) a radical of formula

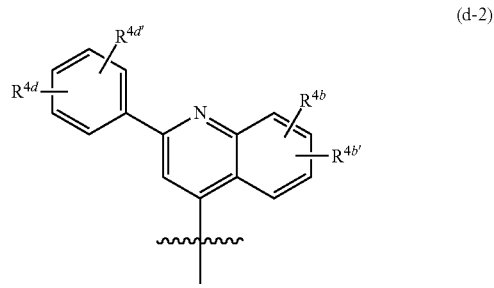

(d-2)

(d-3) a radical of formula (d-3)
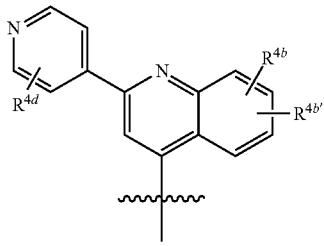

(d-4) a radical of formula (d-4)
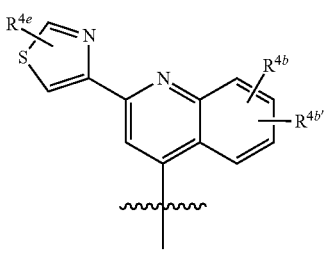

or in particular, (d-4-a) a radical of formula (d-4-a)
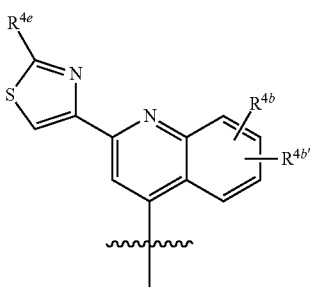

(d-5) a radical of formula (d-5)
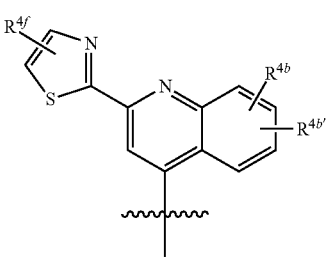

or in particular, (d-5-a) a radical of formula (d-5-a)
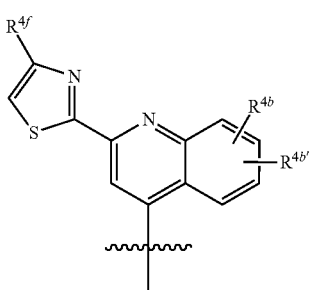

wherein in radicals (d-1)-(d-5), as well as in (d-4-a) and (d-5-a):

each $R^{4a}$, $R^{4b}$, $R^{4b'}$, $R^{4d}$, $R^{4d'}$, $R^{4e}$, $R^{4f}$ are independently any of the substituents selected from those mentioned as possible substituents on the monocyclic or bicyclic ring systems of $R^4$, as specified in the definitions of the compounds of formula (I) or of any of the subgroups of compounds of formula (I);

or, in particular, wherein in radicals (d-1)-(d-5), as well as in (d-4-a) and (d-5-a):

$R^{4b}$ and $R^{4b'}$ may, independently, be hydrogen, $C_{1-6}$alkyl, $C_{1-6}$alkoxy, —$NR^{5a}R^{5b}$ (in particular amino or mono- or di$C_{1-6}$alkylamino), —C(=O)$NR^{5a}R^{5b}$, (in particular aminocarbonyl or mono- or di$C_{1-6}$alkylaminocarbonyl), nitro, hydroxy, halo, trifluoromethyl, —C(=O)OH, or —C(=O)O$R^{6a}$ (in particular wherein $R^{6a}$ is $C_{1-6}$alkyl);

wherein each $R^{5a}$, $R^{5b}$, $R^{6a}$ mentioned above or hereinafter independently is as defined in the definitions of the compounds of formula (I) or of any of the subgroups of compounds of formula (I);

or, in particular, wherein in radicals (d-1)-(d-5), as well as in (d-4-a) and (d-5-a): $R^{4a}$ is hydrogen, $C_{1-6}$alkyl, $C_{1-6}$alkoxy, $C_{1-6}$alkylthio, mono$C_{1-6}$alkylamino, amino, $C_{3-7}$cycloalkyl, aryl, or Het;

more specifically $R^{4a}$ is aryl or Het; of interest are embodiments wherein $R^{4a}$ is phenyl, pyridyl, thiazolyl, pyrazolyl, each substituted as specified in the definitions of the compounds of formula (I) or of any of the subgroups of the compounds of formula (I);

in specific embodiments said aryl or Het may each, independently, optionally substituted with $C_{1-6}$alkyl, $C_{1-6}$alkoxy, amino, mono- or di$C_{1-6}$alkylamino, pyrrolidinyl, piperidinyl, morpholinyl, piperazinyl, 4-$C_{1-6}$alkylpiperazinyl; and wherein the morpholinyl, and piperidinyl groups may optionally substituted with one or two $C_{1-6}$alkyl radicals; and in particular $R^{4a}$ can be a radical Het; wherein Het may include pyrrolidinyl, piperidinyl, morpholinyl, piperazinyl, 4-$C_{1-6}$alkylpiperazinyl; and wherein the morpholinyl and piperidinyl groups may optionally substituted with one or two $C_{1-6}$alkyl radicals;

Embodiments of the invention are compounds of formula (I) or any of the subgroups of compounds of formula (I) wherein $R^{4a}$ is a radical (q)
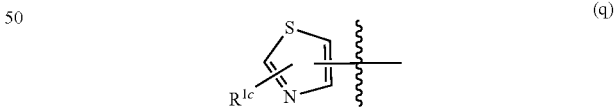

(q')

(q'-1)
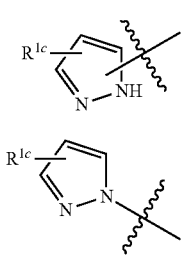

or, in particular, wherein $R^{4a}$ is selected from the group consisting of:

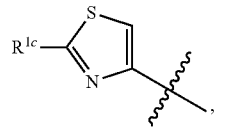
(q-1)

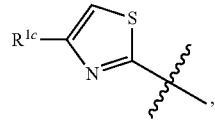
(q-2)

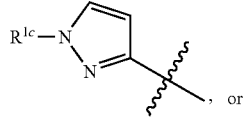
(q-3)

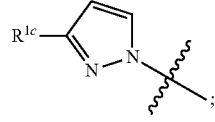
(q-4)

wherein, where possible a nitrogen may bear an $R^{4c}$ substituent or a link to the remainder of the molecule; each $R^{4c}$ is any of the $R^4$ substituents may be selected from those mentioned as possible substituents on the monocyclic or bicyclic ring systems of $R^4$ as specified in the definitions of the compounds of formula (I) or of any of the subgroups of compounds of formula (I);

specifically each $R^{4c}$ may be hydrogen, halo, $C_{1-6}$alkyl, $C_{1-6}$alkoxy, polyhalo$C_{1-6}$alkyl (in particular trifluoromethyl), —$NR^{5a}R^{5b}$ (in particular amino or mono- or di$C_{1-6}$alkyl-amino), —C(=O)$NR^{5a}R^{5b}$, (in particular aminocarbonyl or mono- or di$C_{1-6}$alkylamino-carbonyl), nitro, hydroxy, —C(=O)OH, or —C(=O)$OR^{6a}$ (in particular wherein $R^{6a}$ is $C_{1-6}$alkyl), phenyl, pyridyl, thiazolyl, pyrazolyl, pyrrolidinyl, piperidinyl, morpholinyl, piperazinyl, 4-$C_{1-6}$alkylpiperazinyl (in particular 4-methylpiperazinyl); and wherein the morpholinyl and piperidinyl groups may optionally substituted with one or two $C_{1-6}$alkyl radicals; and the phenyl, pyridyl, thiazolyl, pyrazolyl groups may be optionally substituted with 1, 2 or 3 (in particular with 1 or 2) substituents each independently selected from $C_{1-6}$alkyl, $C_{1-6}$alkoxy, halo, amino, mono- or di$C_{1-6}$alkylamino;

more specifically each $R^{4c}$ may be hydrogen, halo, $C_{1-6}$alkyl, amino, or mono- or di-$C_{1-6}$alkylamino, pyrrolidinyl, piperidinyl, morpholinyl, piperazinyl, 4-$C_{1-6}$alkyl-piperazinyl; and wherein the morpholinyl and piperidinyl groups may optionally substituted with one or two $C_{1-6}$alkyl radicals;

and where $R^{4c}$ is substituted on a nitrogen atom, it preferably is a carbon containing substituent that is connected to the nitrogen via a carbon atom or one of its carbon atoms;

specifically each $R^{4d}$ and $R^{4d'}$ independently may be hydrogen, $C_{1-6}$alkyl, $C_{1-6}$alkoxy, or halo;

or more specifically each $R^{4d}$ in (d-3) may be hydrogen, $C_{1-6}$alkyl, $C_{1-6}$alkoxy or halo;

specifically $R^{4e}$ may be hydrogen, $C_{1-6}$alkyl, amino, mono- or di$C_{1-6}$alkylamino, pyrrolidinyl, piperidinyl, morpholinyl, piperazinyl, 4-$C_{1-6}$alkylpiperazinyl (in particular 4-methylpiperazinyl); and wherein the morpholinyl and piperidinyl groups may optionally substituted with one or two $C_{1-6}$alkyl radicals;

preferably each $R^{4b}$ is $C_{1-6}$alkoxy, more preferably methoxy; specifically $R^{4f}$ may be hydrogen, $C_{1-6}$alkyl, amino, mono- or di$C_{1-6}$alkylamino, pyrrolidinyl, piperidinyl, piperazinyl, 4-$C_{1-6}$alkylpiperazinyl (in particular, 4-methyl-piperazinyl), or morpholinyl.

Specific embodiments of the invention are compounds of formula (I) or any of the subgroups of compounds of formula (I) wherein $R^4$ is 7-methoxy-2-phenyl-quinolin-4-yl and L is —O—.

Embodiments of the invention are compounds of formula (I) or any of the subgroups of compounds of formula (I) wherein $R^4$ is (e) isoquinolinyl (in particular 1-isoquinolinyl), optionally substituted with 1, 2, 3 or 4 (or with 1, 2 or 3) substituents selected from those mentioned as possible substituents on the monocyclic or bicyclic ring systems of $R^4$, as specified in the definitions of the compounds of formula (I) or of any of the subgroups of compounds of formula (I).

Specific such embodiments are those wherein $R^4$ is
(e-1) a radical of formula:

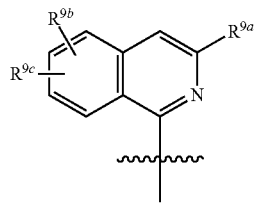
(e-1)

or in particular (e-1-a) a radical of formula:

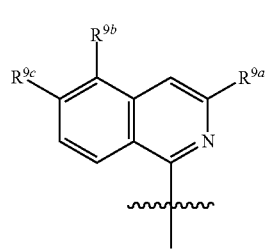
(e-1-a)

wherein $R^{9a}$, $R^{9b}$, $R^{9c}$ independently form one another are any of the substituents selected from those mentioned as possible substituents on the monocyclic or bicyclic ring systems of $R^4$, as specified in the definitions of the compounds of formula (I) or of any of the subgroups of compounds of formula (I); in particular $R^{9a}$ may have the same meanings as $R^{4a}$ as specified above; in particular it may be aryl or Het, either of which is optionally substituted with any of the radicals mentioned as substituents of aryl or of Het as specified definitions of the compounds of formula (I) or of any of the subgroups of compounds of formula (I) (including the number of substituents); specifically said aryl or Het may be substituted with 1, 2 or 3 (in particular with one) radical or radicals $R^{10}$; wherein said $R^{10}$ is any of the radicals mentioned as substituents of aryl or Het as specified definitions of the compounds of formula (I) or of any of the subgroups of compounds of formula (I) as defined above; or in particular $R^{10}$ is hydrogen, $C_{1-6}$alkyl, $C_{3-7}$cycloalkyl, ohenyl, pyridyl, thiazolyl, pyrazolyl, amino optionally mono or disubstituted with $C_{1-6}$alkyl, or aminocarbonyl or mono- or diC$_{1-6}$alkyl-aminocarbonyl; wherein Het also includes pyrrolidinyl, piperidinyl, piperazinyl, 4-C$_{1-6}$alkylpiperazinyl (e.g. 4-methylpiperazinyl), or morpholinyl; and wherein the morpholinyl or piperidinyl groups may optionally substituted with one or two C$_{1-6}$alkyl radicals; and the phenyl, pyridyl, thiazolyl, pyrazolyl groups may be optionally substituted with 1, 2 or 3 (in particular with 1 or 2) substituents each independently selected from C$_{1-6}$alkyl, C$_{1-6}$alkoxy, halo, amino, mono- or diC$_{1-6}$alkylamino;

R$^{9b}$ may have the same meanings as R$^{4b}$ as specified above; in particular it may be is hydrogen, C$_{1-6}$alkyl, C$_{3-7}$cycloalkyl, aryl, Het, halo (e.g. bromo, chloro or fluoro);

R$^{9c}$ may have the same meanings as R$^{4c}$ as specified above; in particular it may be is hydrogen or C$_{1-6}$alkoxy.

In particular R$^{9a}$ in the isoquinolinyl radical specified under (e-1) or (1-e-a) includes phenyl, pyridyl, thiazolyl, oxazolyl or pyrazolyl either of which is optionally substituted with R$^{10}$ as defined above, in particular optionally substituted with an R$^{10}$ which may be hydrogen, C$_{1-6}$alkyl (e.g. methyl, ethyl, isopropyl, tert-butyl), amino, pyrrolidinyl, piperidinyl, piperazinyl, 4-C$_{1-6}$alkylpiperazinyl (e.g. 4-methylpiperazinyl), or morpholinyl, C$_{1-6}$alkylamino, (C$_{1-6}$alkyl)$_2$amino, aminocarbonyl, or mono- or diC$_{1-6}$alkylaminocarbonyl; and wherein the morpholinyl and piperidinyl groups may optionally substituted with one or two C$_{1-6}$alkyl radicals.

Preferably R$^{9a}$ in the isoquinolinyl radical specified under (e-1) or (e-1-a) includes any of radicals (q), (q'), (q'-1), (q-1), (q-2), (q-3), (q-4) specified above as well as:

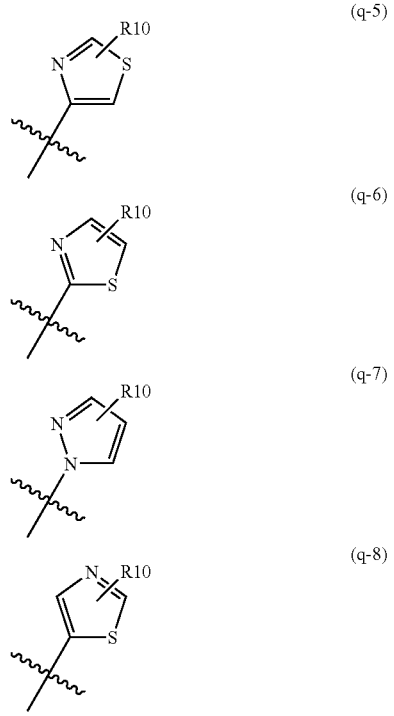

(q-5)

(q-6)

(q-7)

(q-8)

wherein each R$^{10}$ is any of the radicals mentioned as substituents of Het as specified in the definitions of the compounds of formula (I) or of any of the subgroups of compounds of formula (I); or in particular R$^{10}$ is as defined above; especially R$^{10}$ is hydrogen, C$_{1-6}$alkyl (e.g. methyl, ethyl, isopropyl, tert-butyl), amino, pyrrolidinyl, piperidinyl, piperazinyl, 4-C$_{1-6}$alkylpiperazinyl (e.g. 4-methylpiperazinyl), or morpholinyl; C$_{1-6}$alkylamino, (C$_{1-6}$alkyl)$_2$amino, aminocarbonyl, or mono- or di-C$_{1-6}$alkylaminocarbonyl; and wherein the morpholine, and piperidine may optionally substituted with one or two C$_{1-6}$alkyl radicals.

Also preferably R$^{9a}$ in the isoquinolinyl radical specified under (e-1) or (e-1-a) includes:

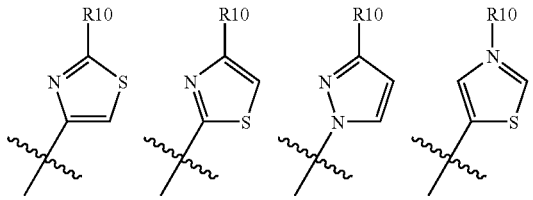

wherein each R$^{10}$ is as defined above, and especially is hydrogen, halo, C$_{1-6}$alkyl (e.g. methyl, ethyl, isopropyl, tert-butyl), amino, pyrrolidinyl, piperidinyl, piperazinyl, 4-C$_{1-6}$alkylpiperazinyl (e.g. 4-methylpiperazinyl), or morpholinyl; C$_{1-6}$alkylamino, (C$_{1-6}$alkyl)$_2$amino, aminocarbonyl, or mono- or diC$_{1-6}$alkylaminocarbonyl; and wherein the morpholinyl, and piperidinyl groups may optionally substituted with one or two C$_{1-6}$alkyl radicals.

R$^{9b}$ in the isoquinolinyl radical specified under (e-2) may be hydrogen, C$_{1-6}$alkyl, halo (e.g. bromo, chloro or fluoro), especially hydrogen or bromo.

R$^{9b}$ in the isoquinolinyl radical specified under (e-2) may be hydrogen or C$_{1-6}$alkoxy (e.g. methoxy).

Embodiments of the invention are compounds of formula (I) or any of the subgroups of compounds of formula (I) wherein R$^4$ is

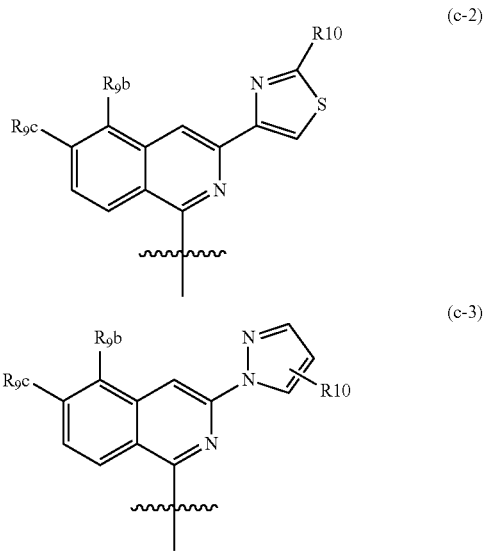

(c-2)

(c-3)

wherein R$^{9b}$ is hydrogen or halo (e.g. bromo) and R$^{9c}$ is hydrogen or C$_{1-6}$alkoxy (e.g. methoxy).

Embodiments of the invention are compounds of formula (I) or any of the subgroups of compounds of formula (I) wherein R$^4$ is (f) quinazolinyl (in particular quinazolin-4-yl), optionally substituted with 1, 2, 3 or 4 (or with 1, 2 or 3) substituents selected from those mentioned as possible substituents on the monocyclic or bicyclic ring systems of R$^4$, as specified in the definitions of the compounds of formula (I) or of any of the subgroups of compounds of formula (I). Quinazoline embodiments of $R^4$ include (f-1) a radical:

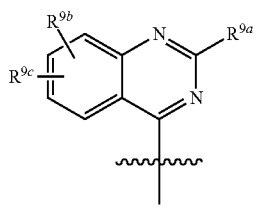

(f-1)

or in particular (f-1-a) a radical:

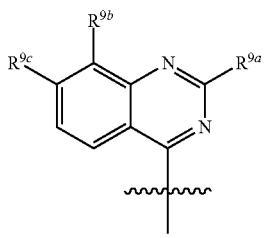

(f-1-a)

wherein $R^{9a}$, $R^{9b}$ and $R^{9c}$ have the meanings stated above in relation to $R^4$ being isoquinolinyl (such as in radicals (e-1), (e-1-a), etc).
wherein specifically $R^{9a}$ is $C_{3-7}$cycloalkyl, aryl or Het, any of which is optionally substituted with one, two or three (in particular with one) $R^{10}$; wherein
$R^{10}$ is hydrogen, $C_{1-6}$alkyl, $C_{3-7}$cycloalkyl, phenyl, pyridyl, thiazolyl, pyrazolyl, pyrrolidinyl, piperidinyl, piperazinyl, 4-methylpiperazinyl, or morpholinyl, aminocarbonyl, mono or di $C_{1-6}$alkylaminocarbonyl; wherein the piperidinyl or morpholinyl may be optionally substituted with one or two $C_{1-6}$alkyl radicals; and the phenyl, pyridyl, thiazolyl, pyrazolyl groups may be optionally substituted with 1, 2 or 3 (or with 1 or 2) substituents each independently selected from $C_{1-6}$alkyl, $C_{1-6}$alkoxy, halo, amino, mono- or di$C_{1-6}$alkylamino (in particular selected from $C_{1-6}$alkyl);
$R^{9b}$ is hydrogen, halogen, $C_{1-6}$alkyl (preferably methyl), $C_{3-7}$cycloalkyl, aryl, Het, halo (in particular bromo, chloro or fluoro);
$R^{9c}$ is hydrogen or $C_{1-6}$alkoxy;
Favoured embodiments of $R^{9a}$ for quinazolines include aryl or Het, especially wherein $R^{9a}$ is phenyl, pyridyl, thiazolyl, oxazolyl or pyrazolyl either of which is optionally substituted with one, two or three (in particular with one) $R^{10}$ as defined.
Embodiments of $R^{10}$ for quinazoline include is hydrogen, methyl, ethyl, isopropyl, tert-butyl, halo (including dihalo, such as difluoro), pyrrolidinyl, piperidinyl, piperazinyl, 4-$C_{1-6}$alkylpiperazinyl (e.g. 4-methylpiperazinyl) or morpholinyl, $C_{1-6}$alkylamino, $(C_{1-6}$alkyl$)_2$amino, amino carbonyl, mono or di$C_{1-6}$alkylaminocarbonyl, or $C_{3-7}$cycloalkyl (in particular cyclopropyl).
Preferably $R^{9a}$ in the quinazolyl radical specified under (f-1) or (f-1-a) includes any of radicals (q), (q'), (q'-1), (q-1), (q-2), (q-3), (q-4), (q-5), (q-6), (q-7), (q-8) specified above; wherein in these radicals $R^{10}$ is as defined above or in particular is hydrogen, $C_{1-6}$alkyl (such as methyl, ethyl, isopropyl, tert-butyl), pyrrolidinyl, piperidinyl, piperazinyl, 4-$C_{1-6}$alkylpiperazinyl, N-methylpiperazinyl or morpholinyl, $C_{1-6}$alkylamino, $(C_{1-6}$alkyl$)_2$amino or amino carbonyl, mono or di$C_{1-6}$alkylaminocarbonyl.

$R^{9a}$ for quinazolines may include

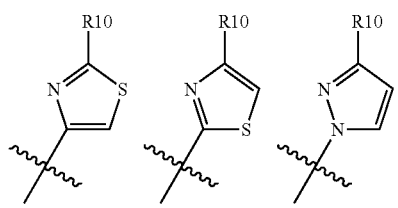

wherein $R^{10}$ is hydrogen, halogen, $C_{1-6}$alkyl (such as methyl, ethyl, isopropyl, tert-butyl), $C_{1-6}$alkylamino, $(C_{1-6}$alkyl$)_2$amino, $C_{1-6}$alkylamido, morpholinyl, or piperidin-1-yl, the morpholinyl and piperidinyl being optionally substituted with one or two $C_{1-6}$alkyl groups.
Additional $R^{9a}$ embodiments for quinazolines include phenyl substituted with one or two $R^{10}$ groups such as is hydrogen, methyl, ethyl, isopropyl, tert-butyl, methoxy, saturated monocyclic amino, $C_{1-6}$alkylamino, $(C_{1-6}$alkyl$)_2$amino or aminocarbonyl, mono- and $C_{1-6}$alkylaminocarbonyl or halo (in particular fluoro).
Embodiments of $R^{9b}$ for quinazolines include hydrogen, $C_{1-6}$alkyl (preferably methyl), halo (e.g. bromo, chloro or fluoro) especially wherein $R^{9b}$ is hydrogen or bromo.
Embodiments of $R^{9c}$ for quinazolines include hydrogen or $C_{1-6}$alkoxy (in particular methoxy).
Specific embodiments of the compounds of formula (I) or any of the subgroups of compounds of formula (I) are those wherein $R^4$ is:

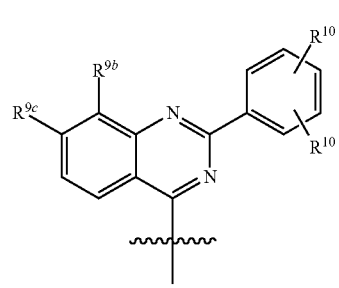

(f-2)

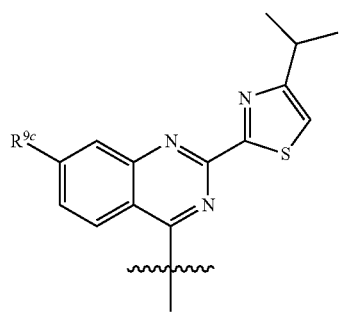

(f-3)

wherein each $R^{10}$ and $R^{9c}$ are as specified above and in particular and $R^{9c}$ is hydrogen or $C_{1-6}$alkoxy (e.g. methoxy).
Embodiments of the invention are compounds of formula (I) or any of the subgroups of compounds of formula (I) wherein $R^1$ is

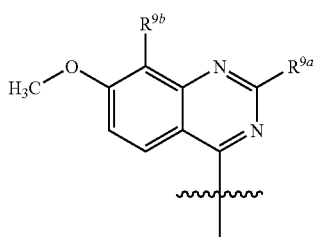
(g-1)

wherein R$^{9a}$ is as defined in any of the groups or subgroups of compounds of formula (I), preferably R$^{9a}$ is p-methoxyphenyl or p-fluoromethyl; and
R$^{9b}$ is hydrogen, halo, methyl, or trifluoromethyl.

Further preferred embodiments of the invention are compounds of formula (I) or any of the subgroups of compounds of formula (I) wherein R$^1$ is:

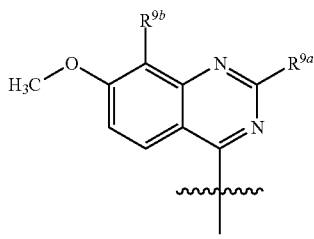
(g-1)

wherein R$^{9a}$ is methoxy, ethoxy or propoxy; and
R$^{9b}$ is hydrogen, fluoro, bromo, chloro, iodo, methyl, ethyl, propyl, or trifluoromethyl.

Further embodiments of the invention are compounds of formula (I) or any of the subgroups of compounds of formula (I) wherein R$^1$ is:

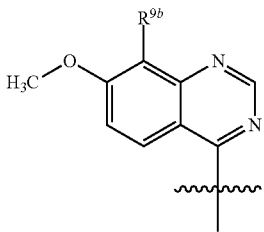
(g-2)

wherein R$^{9b}$ is hydrogen, halo, or trifluoromethyl.

Preferred amongst the subgroups of compounds of the embodiments wherein R$^4$ is a radical (d-1)-(d-5), (e-1)-(e-3), (f-1)-(f-3) as specified above, are those compounds within these subgroups wherein is L is —O—.

Embodiments of the invention are compounds of formula (I) or any of the subgroups of compounds of formula (I) wherein L is a direct bond and R$^4$ is selected from the group consisting of 1H-pyrrole, 1H-imidazole, 1H-pyrazole, furan, thiophene, oxazole, thiazole, isoxazole, isothiazole, pyridine, pyridazine, pyrimidine, pyrazine, phthalazine, quinoxaline, quinazoline, quinoline, cinnoline, 1H-pyrrolo[2,3-b]pyridine, 1H-indole, 1H-benzoimidazole, 1H-indazole, 7H-purine, benzothiazole, benzoxazole, 1H-imidazo-[4,5-c]pyridine, 1H-imidazo[4,5-b]pyridine, 1,3-dihydrobenzimidazol-2-one, 1,3-dihydrobenzimidazol-2-thione, 2,3-dihydro-1H-indole, 1,3-dihydro-indol-2-one, 1H-indole-2,3-dione, 1H-pyrrolo[2,3-c]pyridine, benzofuran, benzo[b]thiophene, benzo[d]isoxazole, benzo[d]isothiazole, 1H-quinolin-2-one, 1H-quinolin-4-one, 1H-quinazolin-4-one, 9H-carbazole, and 1H-quinazolin-2-one, each optionally substituted with the R$^4$ substituents specified in the definitions of the compounds of formula (I) or any of the subgroups of compounds of formula (I).

Further embodiments of the invention are compounds of formula (I) or any of the subgroups of compounds of formula (I) wherein L is a direct bond and R$^4$ is selected from the group consisting of pyrrolidine, 4,5-dihydro-1H-pyrazole, pyrazolidine, imidazolidin-2-one, pyrrolidin-2-one, pyrrolidine-2,5-dione, piperidine-2,6-dione, piperidin-2-one, piperazine-2,6-dione, piperazin-2-one, piperazine, morpholine, pyrazolidin-3-one, imidazolidine-2,4-dione, piperidine, tetrahydrofuran, tetrahydropyran, 1,4-dioxane, and 1,2,3,6-tetrahydropyridine, each optionally substituted with the R$^4$ substituents specified in the definitions of the compounds of formula (I) or any of the subgroups of compounds of formula (I).

Embodiments of the invention are compounds of formula (I) or any of the subgroups of compounds of formula (I) wherein L is a direct bond and R$^4$ is optionally substituted tetrazolyl as depicted below:

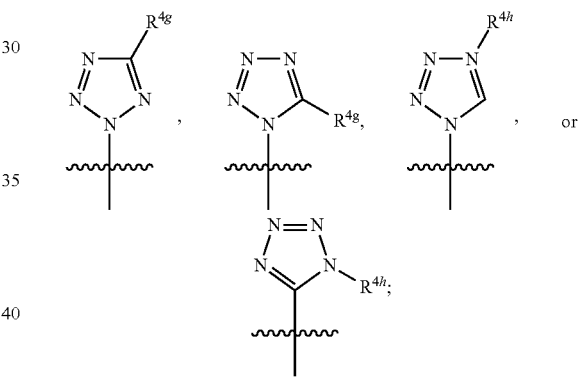

wherein R$^{4g}$ is hydrogen, C$_{1-6}$alkoxy, hydroxy, —NR$^{5a}$R$^{5b}$, —C(=O)R$^7$, —SO$_p$R$^8$, C$_{3-7}$cycloalkyl, aryl, Het, or C$_{1-6}$alkyl optionally substituted with C$_{3-7}$cycloalkyl, aryl, or Het;
R$^{4h}$ is hydrogen, —NR$^{5a}$R$^{5b}$, C$_{3-7}$cycloalkyl, aryl, Het, or C$_{1-6}$alkyl optionally substituted with C$_{3-7}$cycloalkyl, aryl, or Het; and
R$^{5a}$, R$^{5b}$, R$^7$, and R$^8$ are as defined above.

Embodiments of the invention are compounds of formula (I) or any of the subgroups of compounds of formula (I) wherein L is a direct bond and R$^4$ is optionally substituted triazolyl as depicted below:

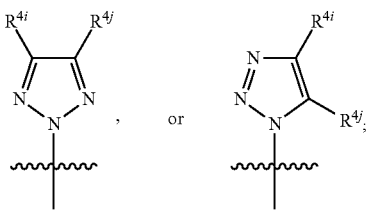

wherein R⁴ⁱ and R⁴ʲ are each, independently, selected from the group consisting of hydrogen, halo, —C(=O)NR⁵ᵃR⁵ᵇ, —C(=O)R⁷, C₃₋₇cycloalkyl, aryl, Het, and C₁₋₆alkyl optionally substituted with —NR⁵ᵃR⁵ᵇ, or aryl; or alternatively, R⁴ⁱ and R⁴ʲ taken together with the carbon atoms to which they are attached, may form a cyclic moiety selected from the group consisting of aryl and Het.

Further preferred substituents for R⁴ when L is a direct bond, include pyridazinone and derivatives thereof as shown below:

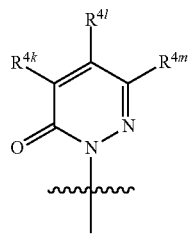

wherein R⁴ᵏ, R⁴ˡ and R⁴ᵐ are independently selected from the group consisting of hydrogen, azido, halo, C₁-C₆alkyl, —NR⁵ᵃR⁵ᵇ, C₃₋₇cycloalkyl, aryl, and Het; or alternatively, R⁴ᵏ and R⁴ˡ or R⁴ˡ and R⁴ᵐ taken together with the carbon atoms to which they are attached, may form a phenyl moiety, which in turn may be optionally substituted with azido, halo, C₁-C₆alkyl, —NR⁵ᵃR⁵ᵇ, C₃₋₇cycloalkyl, aryl or Het.

Embodiments of the invention are compounds of formula (I) or any of the subgroups of compounds of formula (I) wherein L is —O—(C=O)—NR⁵ᵃ— or in particular wherein L is —O—(C=O)—NH— and R⁴ is aryl as defined above; or R⁴ is phenyl optionally substituted with 1, 2 or three substituents selected from those mentioned as possible substituents of the radical aryl as in the definitions of the compounds of formula (I) or of any of the subgroups of compounds of formula (I); specifically R⁴ is a radical of formula:

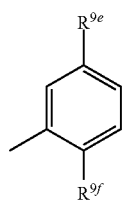

wherein
R⁹ᵉ is hydrogen, C₁₋₆alkyl, polyhaloC₁₋₆alkyl or halo;
R⁹ᶠ is —COOH, —C(=O)OR⁶ᵃ, halo, Het or aryl; wherein Het and aryl are as defined herein and
R⁶ᵃ is C₁₋₆alkyl, preferably R¹⁰ is methyl or ethyl;

In particular, R⁹ᵉ may be hydrogen, fluoro or trifluoromethyl.

In particular, R⁹ᶠ may be —COOC₁₋₆alkyl (e.g. —C(=O)OEt), phenyl, thiazolyl, 1-piperidinyl or 1-pyrazolyl, the phenyl, piperidinyl and pyrazolyl groups being optionally substituted with C₁₋₆alkyl, in particular with methyl.

Other embodiments of the invention are compounds of formula (I) or any of the subgroups of compounds of formula (I) wherein L is —O—(C=O)—NR⁵ᵃ— or, in particular, wherein L is —O—(C=O)—NH— and R⁴ is a radical of formula:

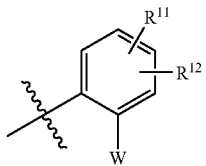

wherein R¹⁰ and R¹¹ independently from one another are hydrogen, halo, hydroxy, nitro, cyano, carboxyl, C₁₋₆alkyl, C₁₋₆alkoxy, C₁₋₆alkoxyC₁₋₆alkyl, C₁₋₆alkylcarbonyl, C₁₋₆alkoxy-carbonyl, amino, azido, mercapto, C₁₋₆alkylthio, polyhaloC₁₋₆alkyl, aryl or Het; especially R¹⁰ and R¹¹ independently from one another are hydrogen, halo, nitro, carboxyl, methyl, ethyl, isopropyl, t-butyl, methoxy, ethoxy, isopropoxy, t-butoxy, methylcarbonyl, ethylcarbonyl, isopropylcarbonyl, t-butyl-carbonyl, methoxycarbonyl, ethoxycarbonyl, isopropoxycarbonyl, t-butoxycarbonyl, methylthio, ethylthio, isopropylthio, t-butylthio, trifluoromethyl, or cyano;

W is aryl or Het, or W is —COOH, —COOR⁶ᵃ, wherein R⁶ᵃ is C₁₋₆alkyl, preferably methyl or ethyl.

Other subgroups of the compounds of formula (I) are those compounds of formula (I), or any subgroup of compounds of formula (I) specified herein, wherein W is phenyl, naphthyl (in particular naphth-1-yl, or naphth-2-yl), pyrrolyl (in particular pyrrol-1-yl), pyridyl (in particular 3-pyridyl), pyrimidinyl (in particular pyrimidin-4-yl), pyridazinyl (in particular pyridazin-3-yl and pyridazin-2-yl), 6-oxo-pyridazin-1-yl, triazolyl (in particular 1,2,3-triazolyl, 1,2,4-triazolyl, more in particular 1,2,3-triazol-2-yl, 1,2,4-triazol-3-yl), tetrazolyl (in particular tetrazol-1-yl, tetrazol-2-yl), pyrazolyl (in particular pyrazol-1-yl, pyrazol-3-yl), imidazolyl (in particular imidazol-1-yl, imidazol-2-yl), thiazolyl (in particular thiazol-2-yl), pyrrolidinyl (in particular pyrrolidin-1-yl), piperidinyl (in particular piperidin-1-yl), piperazinyl (in particular 1-piperazinyl), 4-C₁₋₆alkylpiperazinyl (in particular 4-C₁₋₆alkylpiperazin-1-yl, more in particular 4-methyl-piperazin-1-yl), furanyl (in particular furan-2-yl), thienyl (in particular thien-3-yl), morpholinyl (in particular morpholin-4-yl); all optionally substituted with one or two substituents selected from C₁₋₆alkyl, polyhaloC₁₋₆alkyl, or C₁₋₆alkoxycarbonyl.

In particular W may be phenyl, naphth-1-yl, naphth-2-yl, pyrrol-1-yl, 3-pyridyl, pyrimidin-4-yl, pyridazin-3-yl, pyridazin-2-yl, 6-oxo-pyridazin-1-yl, 1,2,3-triazol-2-yl, 1,2,4-triazol-3-yl, tetrazol-1-yl, tetrazol-2-yl, pyrazol-1-yl, pyrazol-3-yl, imidazol-1-yl, imidazol-2-yl, thiazol-2-yl, pyrrolidin-1-yl, piperidin-1-yl, furan-2-yl, thien-3-yl, morpholin-4-yl; all optionally substituted with one or two substituents selected from C₁₋₆alkyl, polyhaloC₁₋₆alkyl (such as trifluoromethyl) and C₁₋₆alkoxycarbonyl.

Further subgroups of the compounds of formula (I) are those compounds of formula (I), or any subgroup of compounds of formula (I) specified herein, wherein W is thiazol-2-yl substituted with one or two C₁₋₆alkyl, such as methyl, ethyl, isopropyl or tert-butyl. Preferred subgroups of the compounds of formula (I) are those compounds of formula (I), or any subgroup of compounds of formula (I) specified herein, wherein W is selected from the following structures:

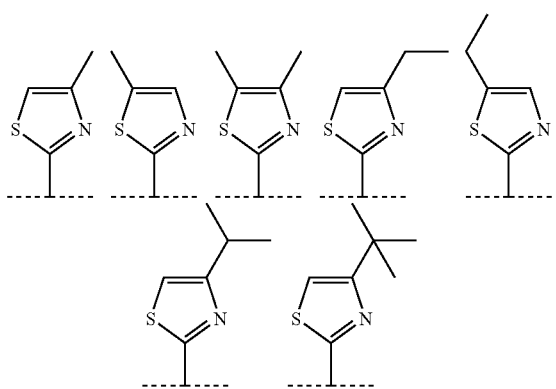

Embodiments of the invention are compounds of formula (I) or any of the subgroups of compounds of formula (I) wherein $R^{11}$ and $R^{12}$ independently from one another are hydrogen, halo, nitro, carboxyl, $C_{1-6}$alkyl, $C_{1-6}$alkoxy, $C_{1-6}$alkylcarbonyl, $C_{1-6}$alkoxy-carbonyl, $C_{1-6}$alkylthio, polyhalo$C_{1-6}$alkyl, cyano, aryl or Het.

Embodiments of the invention are compounds of formula (I) or any of the subgroups of compounds of formula (I) wherein $R^{11}$ and $R^{12}$ independently from one another are hydrogen, halo, nitro, carboxyl, methyl, ethyl, isopropyl, tert-butyl, methoxy, ethoxy, isopropoxy, tert-butoxy, methylcarbonyl, ethylcarbonyl, isopropylcarbonyl, tert-butyl-carbonyl, methoxycarbonyl, ethoxycarbonyl, isopropoxycarbonyl, tert-butoxycarbonyl, methylthio, ethylthio, isopropylthio, tert-butylthio, trifluoromethyl, or cyano.

Preferred embodiments of the invention are compounds of formula (I) or any of the subgroups of compounds of formula (I) wherein one of $R^{11}$ and $R^{12}$ is hydrogen.

Preferred embodiments of the invention are compounds of formula (I) or any of the subgroups of compounds of formula (I) wherein one of $R^{11}$ and $R^{12}$ is halo (in particular fluoro), trifluoromethyl or $C_{1-6}$alkyl (in particular methyl). Other preferred embodiments are those wherein one of $R^{11}$ and $R^{12}$ is halo (in particular fluoro), trifluoromethyl or methyl, and the other of $R^{11}$ and $R^{12}$ is hydrogen.

Preferred embodiments of the invention are compounds of formula (I) or any of the subgroups of compounds of formula (I) wherein one of $R^{11}$ and $R^{12}$ is in para position in respect of the W group. Further preferred embodiments are compounds of formula (I) or any of the subgroups of compounds of formula (I) wherein one of $R^{11}$ and $R^{12}$ is halo (in particular fluoro), trifluoromethyl or methyl, and is in para position in respect of the W group; the other of $R^{11}$ and $R^{12}$ may be as defined above or may be hydrogen.

The compounds of formula (I) consist of three building blocks P1, P2, P3. Building block P1 further contains a P1' tail. The carbonyl group marked with an asterisk in compound (I-c) below may be part of either building block P2 or of building block P3. For reasons of chemistry, building block P2 of the compounds of formula (I) wherein X is C incorporates the carbonyl group attached to the position 1'.

The linking of building blocks P1 with P2, P2 with P3, and P1 with P1' (the group —NH—S(O)$_p$—NR$^{1a}$R$^{2a}$) involves forming an amide bond. The linking of blocks P1 and P3 involves double bond formation. The linking of building blocks P1, P2 and P3 to prepare compounds (I-i) or (I-j) can be done in any given sequence. One of the steps involves a cyclization whereby the macrocycle is formed.

Represented herebelow are compounds (I-i) which are compounds of formula (I) wherein carbon atoms C7 and C8 are linked by a double bond, and compounds (I-j) which are compounds of formula (I) wherein carbon atoms C7 and C8 are linked by a single bond. The compounds of formula (I-j) can be prepared from the corresponding compounds of formula (I-i) by reducing the double bond in the macrocycle.

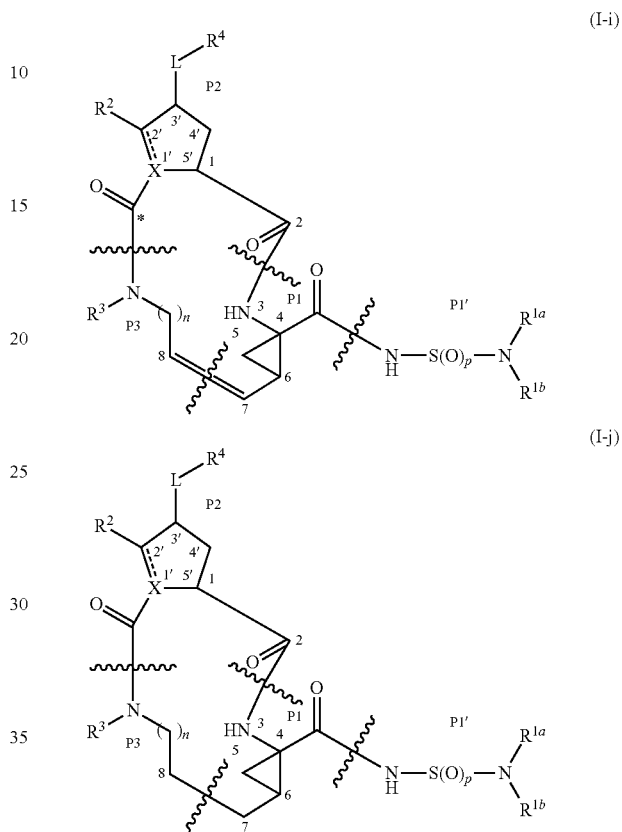

In order to simplify the structural representation of the intermediates and end products in the procedures described herein after, the group $$-NH-S(O)_p-N\begin{matrix}R^{1a}\\R^{1b}\end{matrix}$$

is represented by —$R^1$.

The synthesis procedures described hereinafter are meant to be applicable for as well the racemates, stereochemically pure intermediates or end products, or any stereoisomeric mixtures. The racemates or stereochemical mixtures may be separated into stereoisomeric forms at any stage of the synthesis procedures. In one embodiment, the intermediates and end products have the stereochemistry specified above in the compounds of formula (I-a) and (I-b).

In one embodiment, compounds (I-i) are prepared by first forming the amide bonds and subsequent forming the double bond linkage between P3 and P1 with concomitant cyclization to the macrocycle.

In a preferred embodiment, compounds (I) wherein the bond between $C_7$ and $C_8$ is a double bond, which are compounds of formula (I-i), as defined above, may be prepared as outlined in the following reaction scheme:

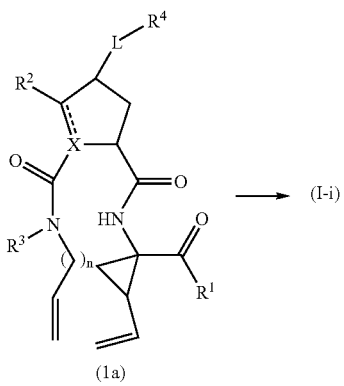

(Ia) → (I-i)

Formation of the macrocycle can be carried out via an olefin metathesis reaction in the presence of a suitable metal catalyst such as e.g. the Ru-based catalyst reported by Miller, S. J., Blackwell, H. E., Grubbs, R. H. J. Am. Chem. Soc. 118, (1996), 9606-9614; Kingsbury, J. S., Harrity, J. P. A., Bonitatebus, P. J., Hoveyda, A. H., J. Am. Chem. Soc. 121, (1999), 791-799; and Huang et al., J. Am. Chem. Soc. 121, (1999), 2674-2678; for example a Hoveyda-Grubbs catalyst.

Air-stable ruthenium catalysts such as bis(tricyclohexylphosphine)-3-phenyl-1H-inden-1-ylidene ruthenium chloride (Neolyst M1®) or bis(tricyclohexylphosphine)-[(phenylthio)methylene]ruthenium (IV) dichloride can be used. Other catalysts that can be used are Grubbs first and second generation catalysts, i.e. Benzylidene-bis(tricyclohexylphosphine)dichlororuthenium and (1,3-bis-(2,4,6-trimethylphenyl)-2-imidazolidinylidene)dichloro(phenylmethylene)-(tricyclohexylphosphine)ruthenium, respectively. Of particular interest are the Hoveyda-Grubbs first and second generation catalysts, which are dichloro(o-isopropoxyphenylmethylene)(tricyclohexylphosphine)-ruthenium(II) and 1,3-bis-(2,4,6-trimethylphenyl)-2-imidazolidinylidene)dichloro-(o-isopropoxyphenylmethylene)ruthenium respectively. Also other catalysts containing other transition metals such as Mo can be used for this reaction.

The metathesis reactions may be conducted in a suitable solvent such as for example ethers, e.g. THF, dioxane; halogenated hydrocarbons, e.g. dichoromethane, CHCl$_3$, 1,2-dichloroethane and the like, hydrocarbons, e.g. toluene. In a preferred embodiment, the metathesis reaction is conducted in toluene. These reactions are conducted at increased temperatures under nitrogen atmosphere.

Compounds of formula (I) wherein the link between C7 and C8 in the macrocycle is a single bond, i.e. compounds of formula (I-j), can be prepared from the compounds of formula (I-i) by a reduction of the C$_7$-C$_8$ double bond in the compounds of formula (I-i). This reduction may be conducted by catalytic hydrogenation with hydrogen in the presence of a noble metal catalyst such as, for example, Pt, Pd, Rh, Ru or Raney nickel. Of interest is Rh on alumina. The hydrogenation reaction preferably is conducted in a solvent such as, e.g. an alcohol such as methanol, ethanol, or an ether such as THF, or mixtures thereof. Water can also be added to these solvents or solvent mixtures.

The R$^1$ group can be connected to the P1 building block at any stage of the synthesis, i.e. before or after the cyclization, or before or after the cyclization and reduction as described herein above. The compounds of formula (I) can be prepared by linking the R$^1$ group to P1 by forming an amide bond between both moieties, as outlined in the following reaction scheme wherein G represents a group:

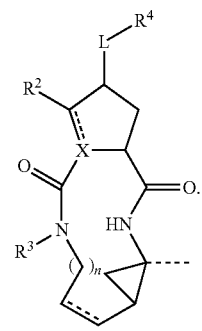

G-COOH + H$_2$N—S(O)$_p$—N(R$^{1a}$)(R$^{1b}$) →
(2a)      (2b)

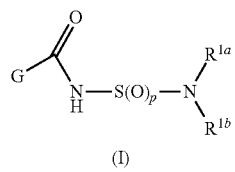

(I)

Intermediate (2a) can be coupled with the sulfonamide (2b) by an amide forming reaction such as any of the procedures for the formation of an amide bond described hereinafter. In particular, (2a) may be treated with a coupling agent, for example N,N'-carbonyldiimidazole (CDI), EEDQ, IIDQ, EDCI or benzotriazol-1-yl-oxy-tris-pyrrolidinophosphonium hexafluorophosphate (commercially available as PyBOP®), in a solvent such as an ether, e.g. THF, or a halogenated hydrocarbon, e.g. dichloromethane, chloroform, dichloroethane, and reacted with the desired sulfonamide (2b), preferably after reacting (2a) with the coupling agent. The reactions of (2a) with (2b) preferably are conducted in the presence of a base, for example a trialkylamine such as triethylamine or diisopropylethylamine, or 1,8-diazabicycle-[5.4.0]undec-7-ene (DBU). Intermediate (2a) can also be converted into an activated form, e.g. an activated form of general formula G-CO—Z, wherein Z represents halo, or the rest of an active ester, e.g. Z is an aryloxy group such as phenoxy, p.nitrophenoxy, pentafluorophenoxy, trichlorophenoxy, pentachlorophenoxy and the like; or Z can be the rest of a mixed anhydride. In one embodiment, G-CO—Z is an acid chloride (G-CO—Cl) or a mixed acid anhydride (G-CO—O—CO—R or G-CO—O—CO—OR, R in the latter being e.g. C$_{1-4}$alkyl, such as methyl, ethyl, propyl, i.propyl, butyl, t.butyl, i.butyl, or benzyl). The activated form G-CO—Z is reacted with the sulfonamide (2b).

The activation of the carboxylic acid in (2a) as described in the above reactions may lead to an internal cyclization reaction to an azalactone intermediate of formula

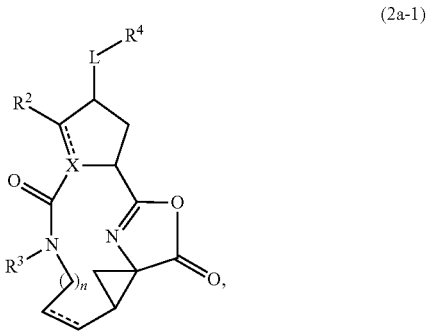

(2a-1)

wherein L, X, R², R³, R⁴, n are as specified above and wherein the stereogenic centers may have the stereochemical configuration as specified above, for example as in (I-a) or (I-b). The intermediates (2a-1) can be isolated from the reaction mixture, using conventional methodology, and the isolated intermediate (2a-1) is then reacted with (2b), or the reaction mixture containing (2a-1) can be reacted further with (2b) without isolation of (2a-1). In one embodiment, where the reaction with the coupling agent is conducted in a water-immiscible solvent, the reaction mixture containing (2a-1) may be washed with water or with slightly basic water in order to remove all water-soluble side products. The thus obtained washed solution may then be reacted with (2b) without additional purification steps. The isolation of intermediates (2a-1) on the other hand may provide certain advantages in that the isolated product, after optional further purification, may be reacted with (2b), giving rise to less side products and an easier work-up of the reaction.

The compounds of formula (I) wherein R³ is hydrogen, said compounds being represented by (I-L), can also be prepared by removal of a protecting group PG, from a corresponding nitrogen-protected intermediate (3a), as in the following reaction scheme. The protecting group PG in particular is any of the nitrogen protecting groups mentioned hereinafter and can be removed using procedures also mentioned hereinafter:

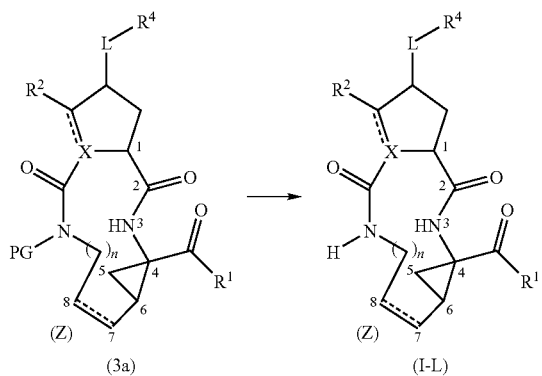

(3a)                    (I-L)

The starting materials (3a) in the above reaction can be prepared following the procedures for the preparation of compounds of formula (I), but using intermediates wherein the group R³ is PG.

The compounds of formula (I) can also be prepared by reacting an intermediate (4a) with intermediates (4b)-(4f) as outlined in the following reaction scheme wherein the various radicals have the meanings specified above and $C_{1-4}$Alk represents $C_{1-4}$alkanediyl:

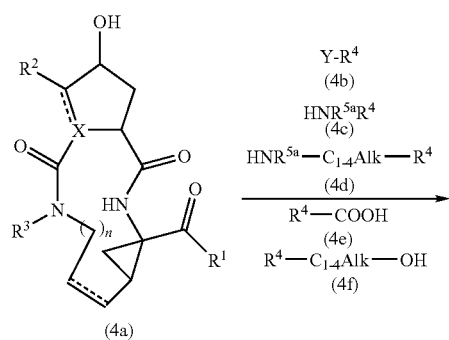

(4a)

Y-R⁴ (4b)
HNR⁵ᵃR⁴ (4c)
HNR⁵ᵃ—C₁₋₄Alk—R⁴ (4d)
R⁴—COOH (4e)
R⁴—C₁₋₄Alk—OH (4f)

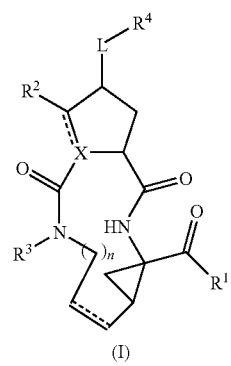

(I)

Y in (4b) represents hydroxy or a leaving group LG such as a halide, e.g. bromide or chloride, or an arylsulfonyl group, e.g. mesylate, triflate or tosylate and the like.

In one embodiment, the reaction of (4a) with (4b) is an O-arylation reaction and Y represents a leaving group. This reaction can be conducted following the procedures described by E. M. Smith et al. (J. Med. Chem. (1988), 31, 875-885). In particular, this reaction is conducted in the presence of a base, preferably a strong base, in a reaction-inert solvent, e.g. one of the solvents mentioned for the formation of an amide bond.

In a particular embodiment, starting material (4a) is reacted with (4b) in the presence of a base which is strong enough to detract a hydrogen from the hydroxy group, for example an alkali of alkaline metal hydride such as LiH or sodium hydride, or alkali metal alkoxide such as sodium or potassium methoxide or ethoxide, potassium tert-butoxide, in a reaction inert solvent like a dipolar aprotic solvent, e.g. DMA, DMF and the like. The resulting alcoholate is reacted with the arylating agent (4b), wherein Y is a suitable leaving group as mentioned above. The conversion of (4a) to (I) using this type of O-arylation reaction does not change the stereochemical configuration at the carbon bearing the hydroxy group.

Alternatively, the reaction of (4a) with (4b) can also be conducted via a Mitsunobu reaction (Mitsunobu, 1981, Synthesis, January, 1-28; Rano et al., Tetrahedron Lett., 1995, 36, 22, 3779-3792; Krchnak et al., Tetrahedron Lett., 1995, 36, 5, 6193-6196; Richter et al., Tetrahedron Lett., 1994, 35, 27, 4705-4706). This reaction comprises treatment of intermediate (4a) with (4b) wherein Y is hydroxyl, in the presence of triphenylphosphine and an activating agent such as a dialkyl azocarboxylate, e.g. diethyl azodicarboxylate (DEAD), diisopropyl azodicarboxylate (DIAD) or the like. The Mitsunobu reaction changes the stereochemical configuration at the carbon bearing the hydroxy group.

Compounds of formula (I) wherein L is a urethane group (L is —O—C(=O)—NR⁵ᵃ—) can be prepared by reacting (4a) with (4c) or (4d) in the presence of a carbonyl introducing agent. The latter comprise reagents such as phosgene or phosgene derivatives such as carbonyl diimidazole (CDI). In one embodiment, (4a) is reacted with phosgene thus providing the corresponding chloroformate which upon reaction with an amine, R⁴—NH₂, or H—NR⁴R⁵ᵃ, provides carbamates i.e. L is —OC(=O)NH— or —OC(=O)NR⁵ᵃ—. The reactions of the chloroformate with the amine preferably are conducted using the same solvents and bases as those mentioned for an amide bond formation, mentioned hereinafter, in particular those mentioned in relation to the reaction of (2a) with (2b). Particular bases are alkali metal carbonates or hydrogen carbonates, e.g. sodium or potassium hydrogen carbonate, or tertairy amines, such as a trialkylamine, e.g. triethylamine.

The reaction of alcohol (4a) with an acid (4e) yields ester derivatives of formula (4a), i.e. L is —O—C(=O)—. Standard procedures for ester formation can be used, in particular those described above in relation to the reaction of (2a) with (2c). These e.g. may involve converting the acid (4e) into an active form such as an acid anhydride or acid halide, for instance an acid chloride ($R^1$—C(=O)Cl), and reacting the active form with the alcohol (4a).

Compounds of formula (I) wherein L is —O—$C_{1-4}$alkanediyl-, can be prepared by an ether forming reaction with (4f). Ether formation can be by azeotropical water removal, or chemically, e.g. by a Williamson reaction.

Compounds of formula (I) wherein L is a direct bond can be prepared by a number of procedures, which are described hereinafter in more detail in the section describing the synthesis of P2 building blocks.

Alternatively, in order to prepare the compounds of formula (I), first an amide bond between building blocks P2 and P1 is formed, followed by coupling of the P3 building block to the P1 moiety in P1-P2, and a subsequent carbamate or ester bond formation between P3 and the P2 moiety in P2-P1-P3 with concomitant ring closure.

Yet another alternative synthetic methodology is the formation of an amide bond between building blocks P2 and P3, followed by the coupling of building block P1 to the P3 moiety in P3-P2, and a last amide bond formation between P1 and P2 in P1-P3-P2 with concomitant ring closure.

Building blocks P1 and P3 can be linked to a P1-P3 sequence. If desired, the double bond linking P1 and P3 may be reduced. The thus formed P1-P3 sequence, either reduced or not, can be coupled to building block P2 and the thus forming sequence P1-P3-P2 subsequently cyclized, by forming an amide bond.

Building blocks P1 and P3 in any of the previous approaches can be linked via double bond formation, e.g. by the olefin metathesis reaction described hereinafter, or a Wittig type reaction. If desired, the thus formed double bond can be reduced, similarly as described above for the conversion of (I-i) to (I-j). The double bond can also be reduced at a later stage, i.e. after addition of a third building block, or after formation of the macrocycle. Building blocks P2 and P1 are linked by amide bond formation and P3 and P2 are linked by carbamate or ester formation.

The tail P1' can be bonded to the P1 building block at any stage of the synthesis of the compounds of formula (I), for example before or after coupling the building blocks P2 and P1; before or after coupling the P3 building block to P1; or before or after ring closure.

The individual building blocks can first be prepared and subsequently coupled together or alternatively, precursors of the building blocks can be coupled together and modified at a later stage to the desired molecular composition.

The functionalities in each of the building blocks may be protected to avoid side reactions.

The formation of amide bonds can be carried out using standard procedures such as those used for coupling amino acids in peptide synthesis. The latter involves the dehydrative coupling of a carboxyl group of one reactant with an amino group of the other reactant to form a linking amide bond. The amide bond formation may be performed by reacting the starting materials in the presence of a coupling agent or by converting the carboxyl functionality into an active form such as an active ester, mixed anhydride or a carboxyl acid chloride or bromide. General descriptions of such coupling reactions and the reagents used therein can be found in general textbooks on peptide chemistry, for example, M. Bodanszky, "Peptide Chemistry", 2nd rev. ed., Springer-Verlag, Berlin, Germany, (1993).

Examples of coupling reactions with amide bond formation include the azide method, mixed carbonic-carboxylic acid anhydride (isobutyl chloroformate) method, the carbodiimide (dicyclohexylcarbodiimide, diisopropylcarbodiimide, or water-soluble carbodiimide such as N-ethyl-N'-[(3-dimethylamino)propyl]carbodiimide) method, the active ester method (e.g. p-nitrophenyl, p-chlorophenyl, trichlorophenyl, pentachloro-phenyl, pentafluorophenyl, N-hydroxysuccinic imido and the like esters), the Woodward reagent K-method, the 1,1-carbonyldiimidazole (CDI or N,N'-carbonyl-diimidazole) method, the phosphorus reagents or oxidation-reduction methods. Some of these methods can be enhanced by adding suitable catalysts, e.g. in the carbodiimide method by adding 1-hydroxybenzotriazole, DBU (1,8-diazabicyclo[5.4.0]undec-7-ene), or 4-DMAP. Further coupling agents are (benzotriazol-1-yloxy)tris-(dimethylamino) phosphonium hexafluorophosphate, either by itself or in the presence of 1-hydroxy-benzotriazole or 4-DMAP; or 2-(1H-benzotriazol-1-yl)-N,N,N',N'-tetra-methyluronium tetrafluoroborate, or O-(7-azabenzotriazol-1-yl)-N,N,N',N'-tetramethyluronium hexafluorophosphate. These coupling reactions can be performed in either solution (liquid phase) or solid phase.

A preferred amide bond formation is performed employing N-ethyloxycarbonyl-2-ethyloxy-1,2-dihydroquinoline (EEDQ) or N-isobutyloxy-carbonyl-2-isobutyloxy-1,2-dihydroquinoline (IIDQ). Unlike the classical anhydride procedure, EEDQ and IIDQ do not require base nor low reaction temperatures. Typically, the procedure involves reacting equimolar amounts of the carboxyl and amine components in an organic solvent (a wide variety of solvents can be used). Then EEDQ or IIDQ is added in excess and the mixture is allowed to stir at room temperature.

The coupling reactions preferably are conducted in an inert solvent, such as halogenated hydrocarbons, e.g. dichloromethane, chloroform, dipolar aprotic solvents such as acetonitrile, dimethylformamide, dimethylacetamide, DMSO, HMPT, ethers such as tetrahydrofuran (THF).

In many instances the coupling reactions are done in the presence of a suitable base such as a tertiary amine, e.g. triethylamine, diisopropylethylamine (DIPEA), N-methylmorpholine, N-methylpyrrolidine, 4-DMAP or 1,8-diazabicycle[5.4.0]undec-7-ene (DBU). The reaction temperature may range between 0° C. and 50° C. and the reaction time may range between 15 min and 24 h.

The functional groups in the building blocks that are linked together may be protected to avoid formation of undesired bonds. Appropriate protecting groups that can be used are listed for example in Greene, "Protective Groups in Organic Chemistry", John Wiley & Sons, New York (1999) and "The Peptides: Analysis, Synthesis, Biology", Vol. 3, Academic Press, New York (1987).

Carboxyl groups can be protected as an ester that can be cleaved off to give the carboxylic acid. Protecting groups that can be used include 1) alkyl esters such as methyl, trimethylsilyl and tert-butyl; 2) arylalkyl esters such as benzyl and substituted benzyl; or 3) esters that can be cleaved by a mild base or mild reductive means such as trichloroethyl and phenacyl esters.

Amino groups can be protected by a variety of N-protecting groups, such as:
1) acyl groups such as formyl, trifluoroacetyl, phthalyl, and p-toluenesulfonyl;
2) aromatic carbamate groups such as benzyloxycarbonyl (Cbz or Z) and substituted benzyloxycarbonyls, and 9-fluorenylmethyloxycarbonyl (Fmoc);
3) aliphatic carbamate groups such as tert-butyloxycarbonyl (Boc), ethoxycarbonyl, diisopropylmethoxy-carbonyl, and allyloxycarbonyl;
4) cyclic alkyl carbamate groups such as cyclopentyloxycarbonyl and adamantyloxycarbonyl;
5) alkyl groups such as triphenylmethyl, benzyl or substituted benzyl such as 4-methoxybenzyl;
6) trialkylsilyl such as trimethylsilyl or t.Bu dimethylsilyl; and
7) thiol containing groups such as phenylthiocarbonyl and dithiasuccinoyl. Interesting amino protecting groups are Boc and Fmoc.

Preferably the amino protecting group is cleaved off prior to the next coupling step. Removal of N-protecting groups can be done following art-known procedures. When the Boc group is used, the methods of choice are trifluoroacetic acid, neat or in dichloromethane, or HCl in dioxane or in ethyl acetate. The resulting ammonium salt is then neutralized either prior to the coupling or in situ with basic solutions such as aqueous buffers, or tertiary amines in dichloromethane or acetonitrile or dimethyl-formamide. When the Fmoc group is used, the reagents of choice are piperidine or substituted piperidine in dimethylformamide, but any secondary amine can be used. The deprotection is carried out at a temperature between 0° C. and room temperature, usually around 15-25° C., or 20-22° C.

Other functional groups that can interfere in the coupling reactions of the building blocks may also be protected. For example hydroxyl groups may be protected as benzyl or substituted benzyl ethers, e.g. 4-methoxybenzyl ether, benzoyl or substituted benzoyl esters, e.g. 4-nitrobenzoyl ester, or with trialkylsilyl groups (e.g. trimethylsilyl or tert-butyldimethylsilyl).

Further amino groups may be protected by protecting groups that can be cleaved off selectively. For example, when Boc is used as the α-amino protecting group, the following side chain protecting groups are suitable: p-toluenesulfonyl (tosyl) moieties can be used to protect further amino groups; benzyl (Bn) ethers can be used to protect hydroxy groups; and benzyl esters can be used to protect further carboxyl groups. Or when Fmoc is chosen for the α-amino protection, usually tert-butyl based protecting groups are acceptable. For instance, Boc can be used for further amino groups; tert-butyl ethers for hydroxyl groups; and tert-butyl esters for further carboxyl groups.

Any of the protecting groups may be removed at any stage of the synthesis procedure but preferably, the protecting groups of any of the functionalities not involved in the reaction steps are removed after completion of the build-up of the macrocycle. Removal of the protecting groups can be done in whatever manner is dictated by the choice of protecting groups, which manners are well known to those skilled in the art.

The intermediates of formula (1a) wherein X is N, said intermediates being represented by formula (1a-1), may be prepared starting from intermediates (5a) which are reacted with an alkenamine (5b) in the presence of a carbonyl introducing agent as outlined in the following reaction scheme.

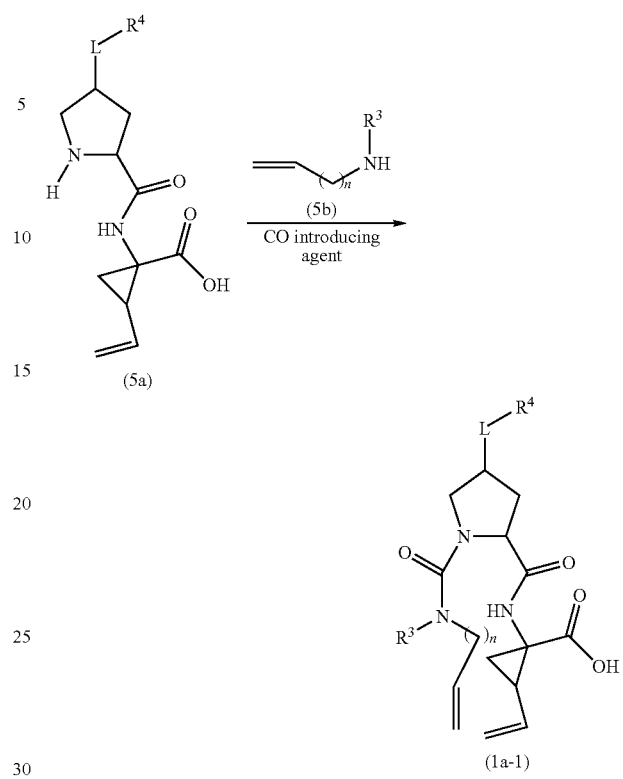

Carbonyl (CO) introducing agents include phosgene, or phosgene derivatives such as carbonyl diimidazole (CDI), and the like. In one embodiment (5a) is reacted with the CO introducing agent in the presence of a suitable base and a solvent, which can be the bases and solvents used in the amide forming reactions as described above. In a particular embodiment, the base is a hydrogencarbonate, e.g. NaHCO$_3$, or a tertiary amine such as triethylamine and the like, and the solvent is an ether or halogenated hydrocarbon, e.g. THF, CH$_2$Cl$_2$, CHCl$_3$, and the like. Thereafter, the amine (5b) is added thereby obtaining intermediates (1a-1) as in the above scheme. An alternative route using similar reaction conditions involves first reacting the CO introducing agent with the amine (5b) and then reacting the thus formed intermediate with (5a).

The intermediates (1a-1) can alternatively be prepared as follows:

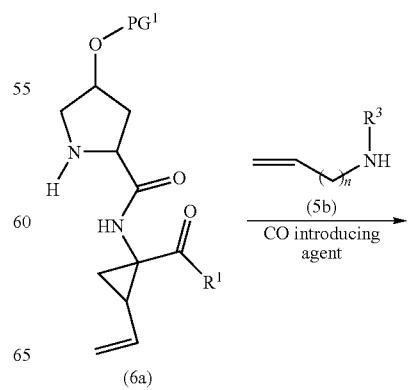

-continued

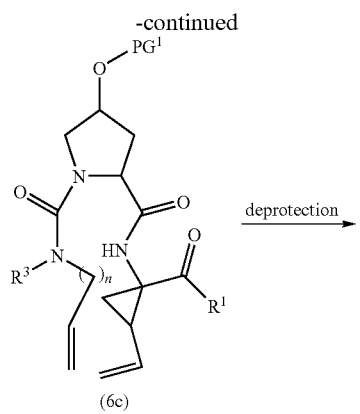

(6c)

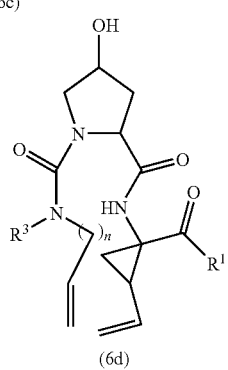

(6d)

PG[1] is an O-protecting group, which can be any of the groups mentioned herein and in particular is a benzoyl or substituted benzoyl group such as 4-nitrobenzoyl. In the latter instance this group can be removed by reaction with a an alkali metal hydroxide (LiOH, NaOH, KOH), in particular where PG[1] is 4-nitrobenzoyl, with LiOH, in an aqueous medium comprising water and a water-soluble organic solvent such as an alkanol (methanol, ethanol) and THF.

Intermediates (6a) are reacted with (5b) in the presence of a carbonyl introducing agent, similar as described above, and this reaction yields intermediates (6c). These are deprotected, in particular using the reaction conditions mentioned above. The resulting alcohol (6d) is reacted with intermediates (4b) as described above for the reaction of (4a) with (4b) and this reaction results in intermediates (1a).

The intermediates of formula (1a) wherein X is C, said intermediates being represented by formula (1a-2), may be prepared by an amide forming reaction starting from intermediates (7a) which are reacted with an amine (5b) as shown in the following reaction scheme, using reaction conditions for preparing amides such as those described above.

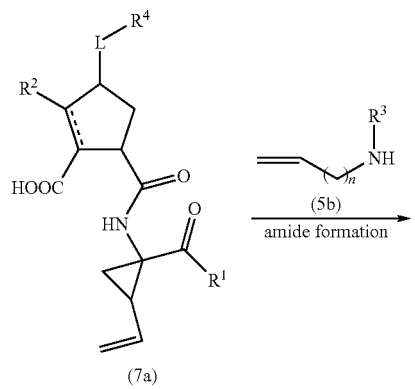

(7a)

-continued

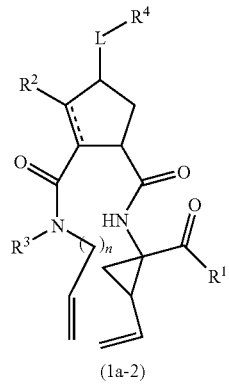

(1a-2)

The intermediates (1a-1) can alternatively be prepared as follows:

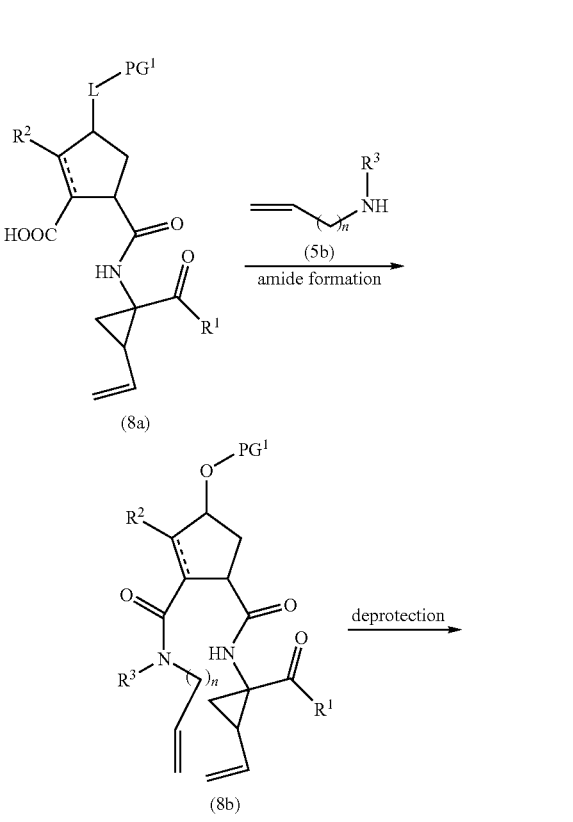

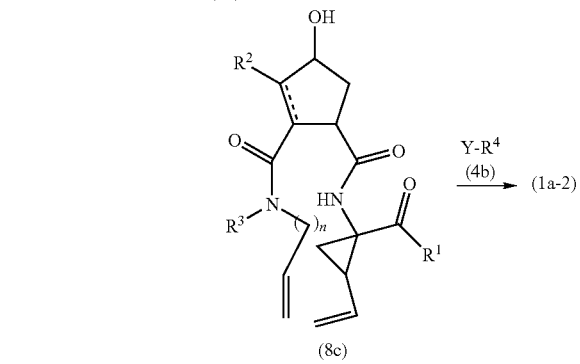

(8c)

PG[1] is an O-protecting group as described above. The same reaction conditions as described above may be used: amide formation as described above, removal of $PG^1$ as in the description of the protecting groups and introduction of $R^4$ as in the reactions of (4a) with the reagents (4b).

The intermediates of formula (2a) may be prepared by first cyclizing the open amide (9a) to a macrocyclic ester (9b), which in turn is converted to (2a) as follows:

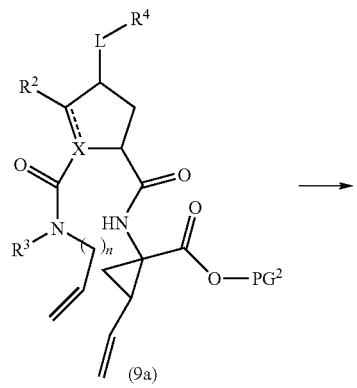

(9a)

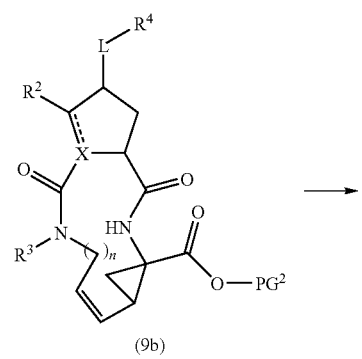

(9b)

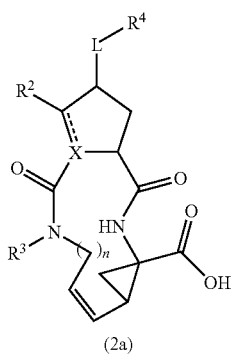

(2a)

$PG^2$ is a carboxyl protecting group, e.g. one of the carboxyl protecting groups mentioned above, in particular a $C_{1-4}$alkyl or benzyl ester, e.g. a methyl, ethyl or t.butyl ester. The reaction of (9a) to (9b) is a metathesis reaction and is conducted as described above. The group PG is removed following procedures also described above. Where $PG^1$ is a $C_{1-4}$alkyl ester, it is removed by alkaline hydrolysis, e.g. with NaOH or preferably LiOH, in an aqueous solvent, e.g. a $C_{1-4}$alkanol/water mixture. A benzyl group can be removed by catalytic hydrogenation.

In an alternative synthesis, intermediates (2a) can be prepared as follows:

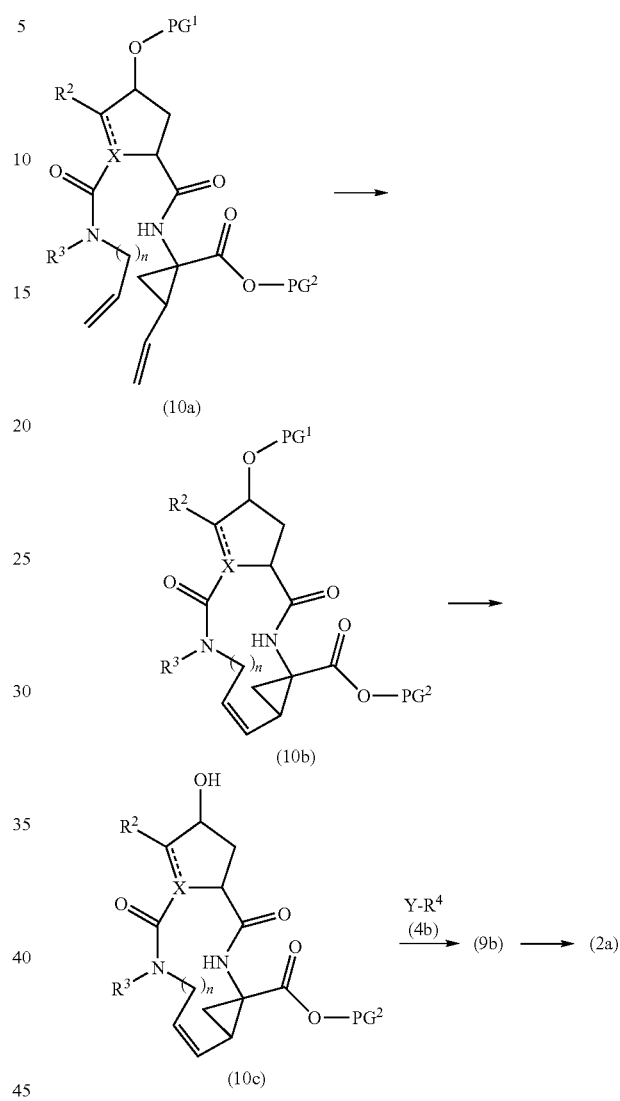

The $PG^1$ group is selected such that it is selectively cleavable towards $PG^2$. $PG^2$ may be e.g. methyl or ethyl esters, which can be removed by treatment with an alkali metal hydroxide in an aqueous medium, in which case $PG^1$ e.g. is t.butyl or benzyl. $PG^2$ may be t.butyl esters removable under weakly acidic conditions or $PG^1$ may be benzyl esters removable with strong acid or by catalytic hydrogenation, in the latter two cases $PG^1$ e.g. is a benzoic ester such as a 4-nitrobenzoic ester.

First, intermediates (10a) are cyclized to the macrocyclic esters (10b), the latter are deprotected by removal of the $PG^1$ group to (10c), which are reacted with intermediates (4b), followed by removal of carboxyl protecting group $PG^2$. The cyclization, deprotection of $PG^1$ and $PG^2$ and the coupling with (4b) are as described above.

The $R^1$ group can be introduced at any stage of the synthesis, either as the last step as described above, or earlier, before the macrocycle formation. The following scheme illustrates the introduction of the group $R^1$ being

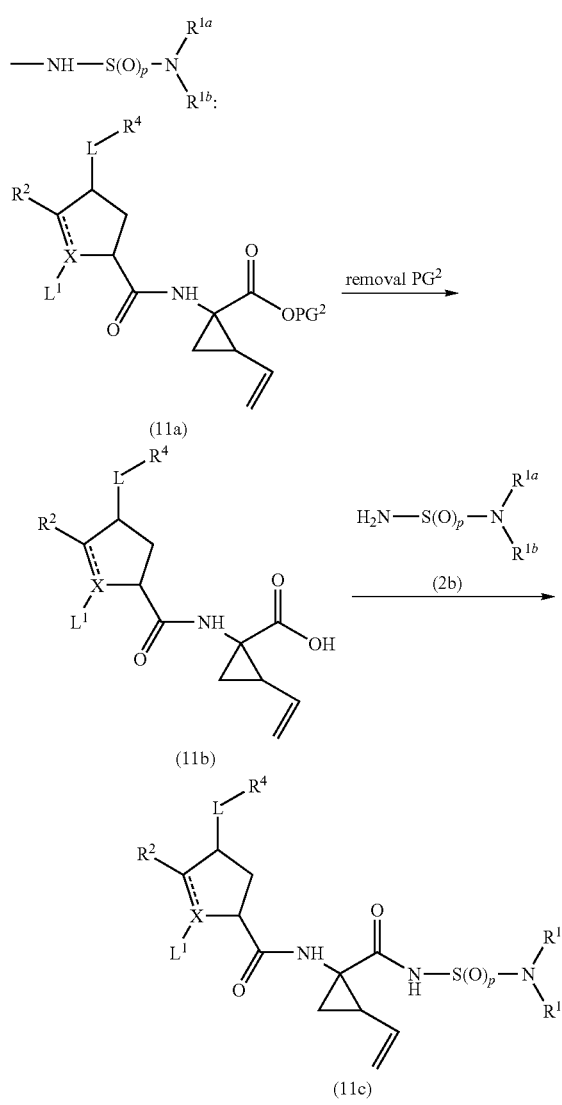

(11a)

(11b)

(11c)

In the above scheme, PG² is as defined above and L¹ is a P3 group

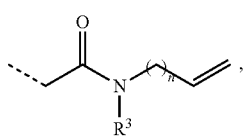

(b)

wherein n and R³ are as defined above and where X is N, L¹ may also be a nitrogen-protecting group (PG, as defined above) and where X is C, L¹ may also be a group —COOPG$^{2a}$, wherein the group PG$^{2a}$ is a carboxyl protecting group similar as PG², but wherein PG$^{2a}$ is selectively cleavable towards PG². In one embodiment PG$^{2a}$ is t.butyl and PG² is methyl or ethyl.

The intermediates (11c) and (11d) wherein L¹ represents a group (b) correspond to the intermediates (1a) and may be processed further as specified above.

Coupling of P1 and P2 Building Blocks

The P1 and P2 building blocks are linked using an amide forming reaction following the procedures described above. The P1 building block may have a carboxyl protecting group PG² (as in (12b)) or may already be linked to P1' group (as in (12c)). L² is a N-protecting group (PG), or a group (b), as specified above. L³ is hydroxy, -OPG¹ or a group -L-R⁴ as specified above. Where in any of the following reaction schemes L³ is hydroxy, prior to each reaction step, it may be protected as a group -OPG¹ and, if desired, subsequently deprotected back to a free hydroxy function. Similarly as described above, the hydroxy function may be converted to a group -L-R⁴.

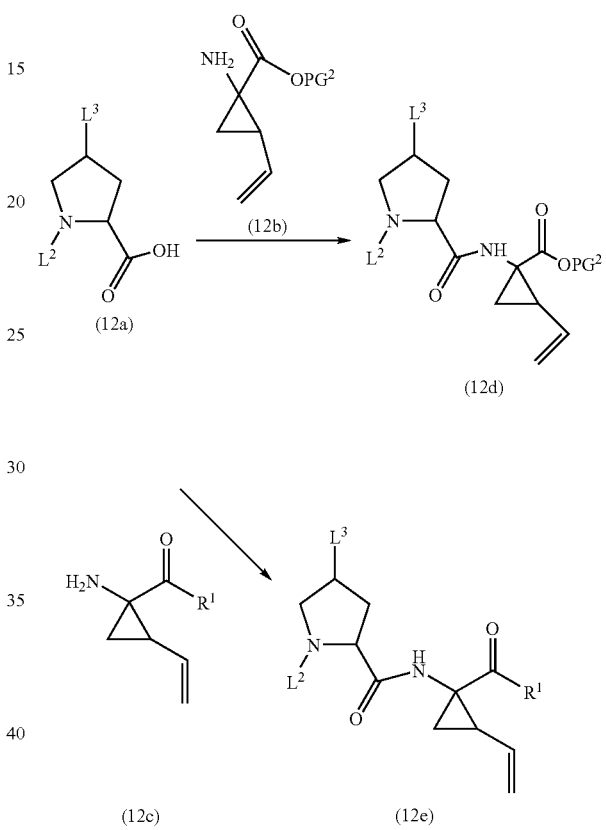

(12a) (12b) (12d)

(12c) (12e)

In the procedure of the above scheme, a cyclopropyl amino acid (12b) or (12c) is coupled to the acid function of the P2 building block (12a) with the formation of an amide linkage, following the procedures described above. Intermediates (12d) or (12e) are obtained. Where in the latter L² is a group (b), the resulting products are P3-P2-P1 sequences encompassing some of the intermediates (11c) or (11d) in the previous reaction scheme. Removal of the acid protecting group in (12d), using the appropriate conditions for the protecting group used, followed by coupling with an amine H₂N—SO₂R⁶ (2b) or with HOR⁵ (2c) as described above, again yields the intermediates (12e), wherein —COR¹ are amide or ester groups. Where L is a N-protecting group, it can be removed yielding intermediates (5a) or (6a). In one embodiment, PG in this reaction is a BOC group and PG² is methyl or ethyl. Where additionally L³ is hydroxy, the starting material (12a) is Boc-L-hydroxyproline. In a particular embodiment, PG is BOC, PG² is methyl or ethyl and L³ is -L-R⁴.

In one embodiment, L² is a group (b) and these reactions involve coupling P1 to P2-P3, which results in the intermediates (1a-1) or (1a) mentioned above. In another embodiment, $L^2$ is a N-protecting group PG, which is as specified above, and the coupling reaction results in intermediates (12d-1) or (12e-1), from which the group PG can be removed, using reaction conditions mentioned above, obtaining intermediates (12-f) or respectively (12g), which encompass intermediates (5a) and (6a) as specified above:

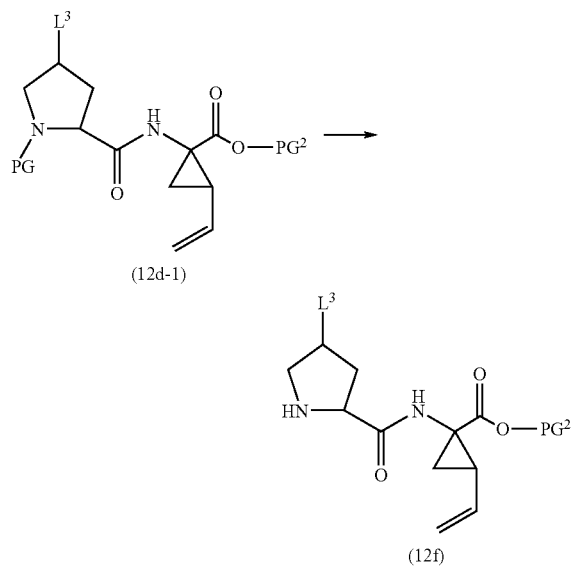

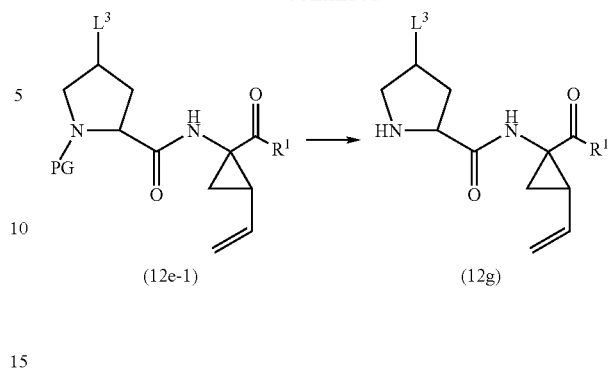

In one embodiment, the group $L_3$ in the above schemes represents a group —O—$PG^1$ which can be introduced on a starting material (12a) wherein $L^3$ is hydroxy. In this instance $PG^1$ is chosen such that it is selectively cleavable towards group $L^2$ being PG.

In a similar way, P2 building blocks wherein X is C, which are cyclopentane or cyclopentene derivatives, can be linked to P1 building blocks as outlined in the following scheme wherein $R^1$, $R^2$, $L^3$, $PG^2$ and PG are carboxyl protecting groups. $PG^{2a}$ typically is chosen such that it is selectively cleavable towards group $PG^2$. Removal of the $PG^{2a}$ group in (13c) yields intermediates (7a) or (8a), which can be reacted with (5b) as described above.

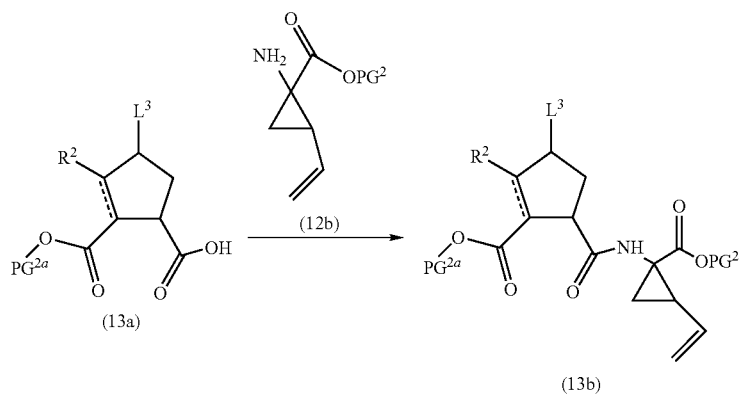

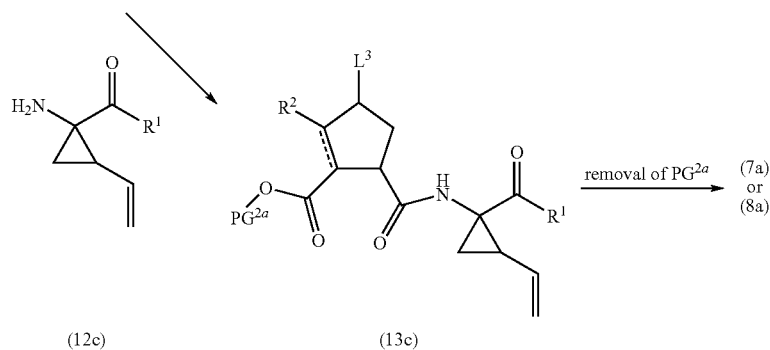

In one particular embodiment, where X is C, R² is H, and where X and the carbon bearing R² are linked by a single bond (P2 being a cyclopentane moiety), PG²ᵃ and L³ taken together form a bond and the P2 building block is represented by formula:

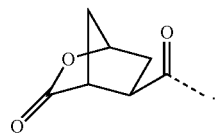

(c)

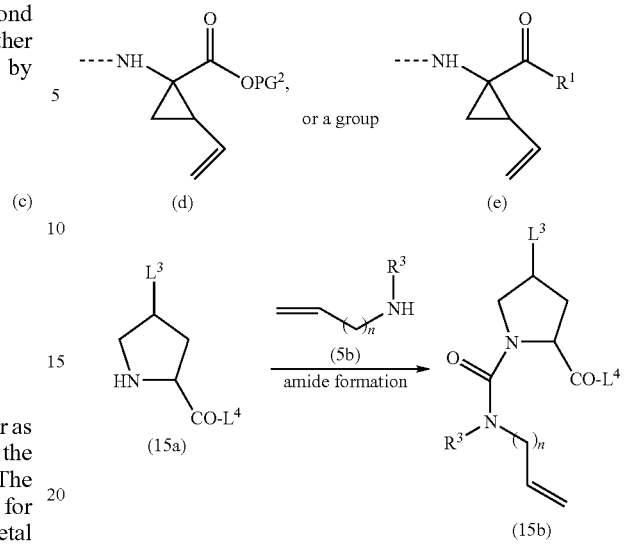

Bicyclic acid (14a) is reacted with (12b) or (12c) similar as described above to (14b) and (14c) respectively, wherein the lactone is opened giving intermediates (14c) and (14e). The lactones can be opened using ester hydrolysis procedures, for example using basic conditions such as an alkali metal hydroxide, e.g. NaOH, KOH, in particular LiOH.

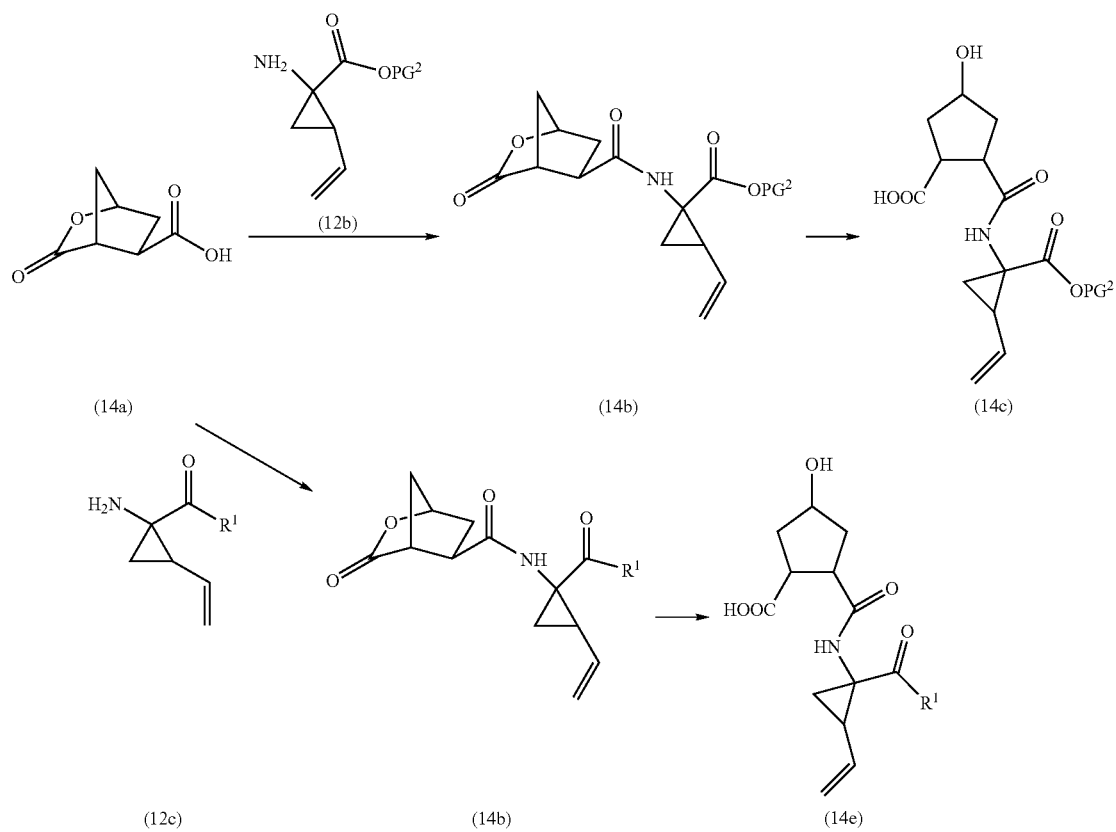

Intermediates (14c) and (14e) can be processed further as described hereinafter.

Coupling of P3 and P2 Building Blocks

For P2 building blocks that have a pyrrolidine moiety, the P3 and P2 or P3 and P2-P1 building blocks are linked using a carbamate forming reaction following the procedures described above for the coupling of (5a) with (5b). A general procedure for coupling P2 blocks having a pyrrolidine moiety is represented in the following reaction scheme wherein L³ is as specified above and L⁴ is a group —O-PG², a group In one embodiment L⁴ in (15a) is a group -OPG², the PG² group may be removed and the resulting acid coupled with cyclopropyl amino acids (12a) or (12b), yielding intermediates (12d) or (12e) wherein L² is a radical (d) or (e).

A general procedure for coupling P3 blocks with a P2 block or a with a P2-P1 block wherein the P2 is a cyclopentane or cyclopentene is shown in the following scheme.

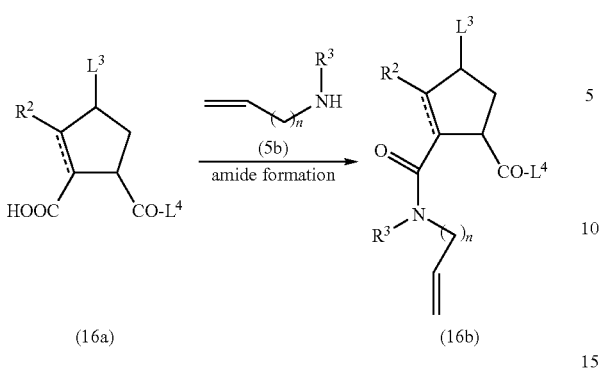

(16a)    (16b)

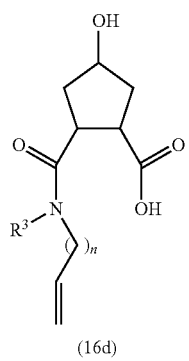

(16d)

In a particular embodiment $L^3$ and $L^4$ taken together may form a lactone bridge as in (14a), and the coupling of a P3 block with a P2 block is as follows:

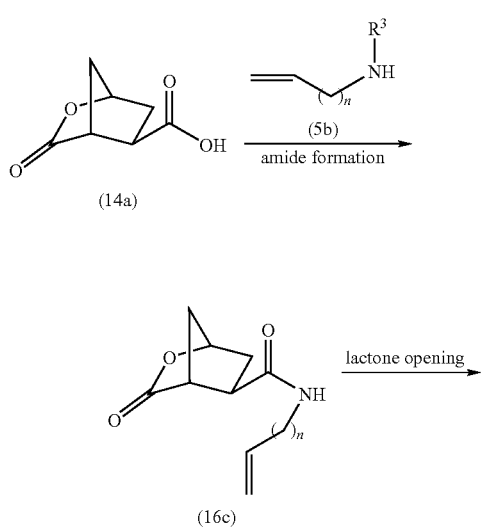

(14a)

(16c)

Bicyclic lactone (14a) is reacted with (5b) in an amide forming reaction to amide (16c) in which the lactone bridge is opened to (16d). The reaction conditions for the amide forming and lactone opening reactions are as described above or hereinafter. Intermediate (16d) in turn can be coupled to a P1 group as described above.

The reactions in the above schemes are conducted using the same procedures as described above for the reactions of (5a), (7a) or (8a) with (5b) and in particular the above reactions wherein $L^4$ is a group (d) or (e) correspond to the reactions of (5a), (7a) or (8a) with (5b), described above.

The building blocks P1, P1', P2 and P3 used in the preparation of the compounds of formula (I) can be prepared starting from art-known intermediates. A number of such syntheses are described hereafter in more detail.

The individual building blocks can first be prepared and subsequently coupled together or alternatively, precursors of the building blocks can be coupled together and modified at a later stage to the desired molecular composition.

The functionalities in each of the building blocks may be protected to avoid side reactions.

Synthesis of P2 Building Blocks

The P2 building blocks contain either a pyrrolidine, a cyclopentane, or a cyclopentene moiety substituted with a group $-L-R^4$.

P2 building blocks containing a pyrrolidine moiety can be derived from commercially available hydroxy proline.

The preparation of P2 building blocks that contain a cylopentane ring may be performed as shown in the scheme below.

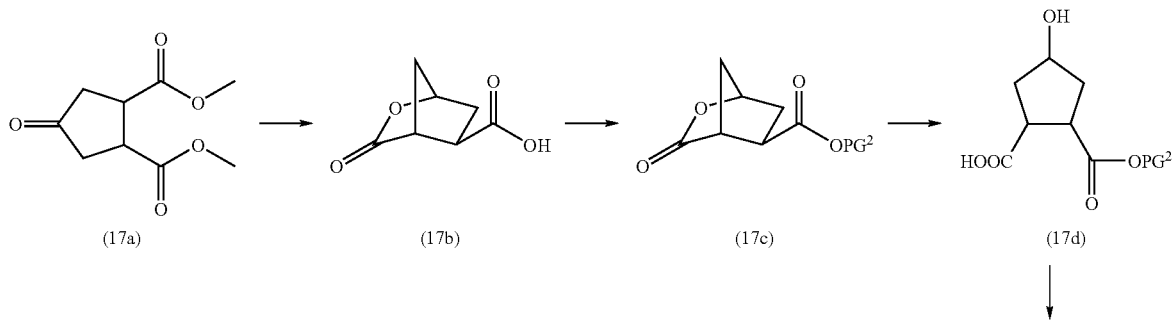

(17a)    (17b)    (17c)    (17d)

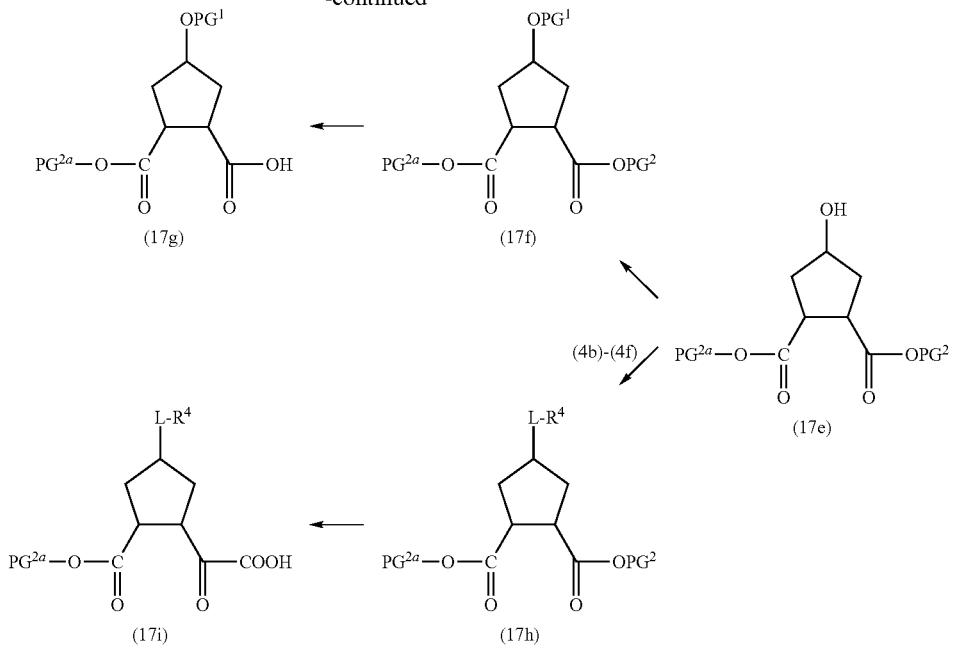

The bicyclic acid (17b) can be prepared, for example, from 3,4-bis(methoxycarbonyl)-cyclopentanone (17a), as described by Rosenquist et al. in Acta Chem. Scand. 46 (1992) 1127-1129. A first step in this procedure involves the reduction of the keto group with a reducing agent like sodium borohydride in a solvent such as methanol, followed by hydrolysis of the esters and finally ring closure to the bicyclic lactone (17b) using lactone forming procedures, in particular by using acetic anhydride in the presence of a weak base such as pyridine. The carboxylic acid functionality in (17b) can then be protected by introducing an appropriate carboxyl protecting group, such as a group $PG^2$, which is as specified above, thus providing bicyclic ester (17c). The group $PG^2$ in particular is acid-labile such as a t.butyl group and is introduced e.g. by treatment with isobutene in the presence of a Lewis acid or with di-tert-butyl dicarbonate in the presence of a base such as a tertiary amine like dimethylamino-pyridine or triethylamine in a solvent like dichloromethane. Lactone opening of (17c) using reaction conditions described above, in particular with lithium hydroxide, yields the acid (17d), which can be used further in coupling reactions with PI building blocks. The free acid in (17d) may also be protected, preferably with an acid protecting group $PG^{2a}$ that is selectively cleavable towards $PG^2$, and the hydroxy function may be converted to a group $-OPG^1$ or to a group $-L-R^4$ using reagents and reaction conditions as described above for the reaction of (4a) with (4b)-(4f), or for the preparation of end products or intermediates wherein L is a directbond, described hereinafter. The products obtained upon removal of the group PG are intermediates (17g) and (17i) which correspond to intermediates (13a) or (16a) specified above.

Intermediates with specific stereochemistry may be prepared by resolving the intermediates in the above reaction sequence. For example, (17b) may be resolved following art-known procedures, e.g. by salt form action with an optically active base or by chiral chromatography, and the resulting stereoisomers may be processed further as described above. The OH and COOH groups in (17d) are in cis position. Trans analogs can be prepared by inverting the stereochemistry at the carbon bearing the OH function by using specific reagents in the reactions introducing $-O-PG^1$ or $-L-R^4$ groups that invert the stereochemistry, such as, e.g. by applying a Mitsunobu reaction. of a $-L-R^4$-substituent as described In one embodiment, the intermediates (17d) are coupled to P1 blocks (12b) or (12c), which coupling reactions correspond to the coupling of (13a) or (16a) with the same P1 blocks, using the same conditions. Subsequent introduction above, followed by removal of the acid protection group $PG^2$, yields intermediates (8a-1), which are a subclass of the intermediates (7a), or part of the intermediates (16a). The reaction products of the $PG^2$ removal can be further coupled to a P3 building block. In one embodiment $PG^2$ in (17d) is t.butyl which can be removed under acidic conditions, e.g. with trifluoroacetic acid.

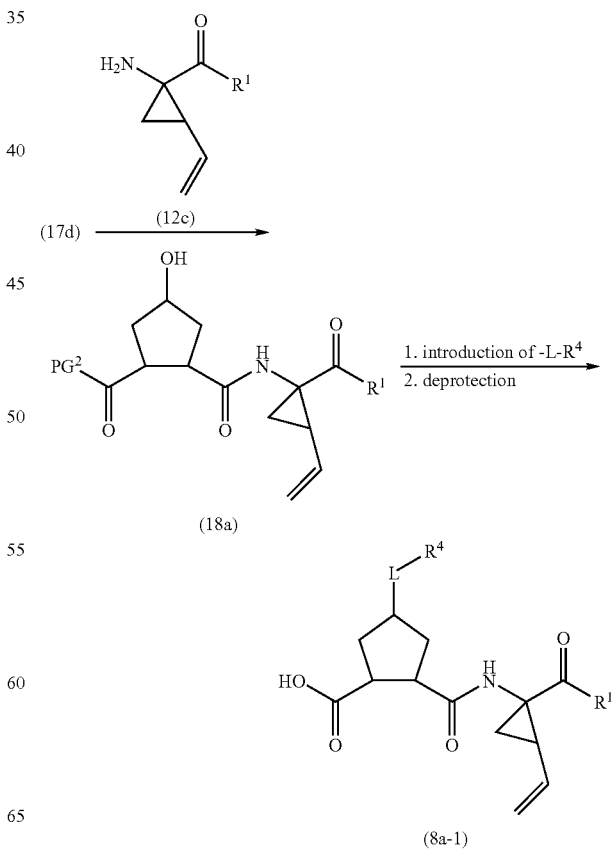

An unsaturated P2 building block, i.e. a cyclopentene ring, may be prepared as illustrated in the scheme below.

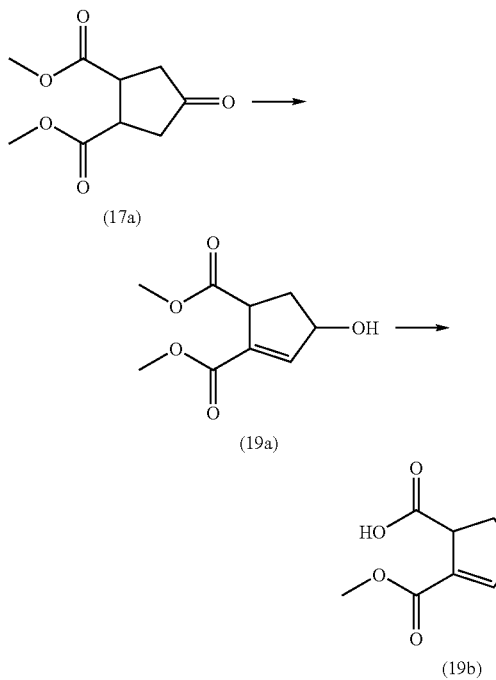

A bromination-elimination reaction of 3,4-bis(methoxycarbonyl)cyclopentanone (17a) as described by Dolby et al. in J. Org. Chem. 36 (1971) 1277-1285 followed by reduction of the keto functionality with a reducing agent like sodium borohydride provides the cyclopentenol (19a). Selective ester hydrolysis using for example lithium hydroxide in a solvent like a mixture of dioxane and water, provides the hydroxy substituted monoester cyclopentenol (19b).

An unsaturated P2 building block wherein $R^2$ can also be other than hydrogen, may be prepared as shown in the scheme below.

Oxidation of commercially available 3-methyl-3-buten-1-ol (20a), in particular by an oxidizing agent like pyridinium chlorochromate, yields (20b), which is converted to the corresponding methyl ester, e.g. by treatment with acetyl chloride in methanol, followed by a bromination reaction with bromine yielding the α-bromo ester (20c). The latter can then be condensed with the alkenyl ester (20e), obtained from (20d) by an ester forming reaction. The ester in (20e) preferably is a t.butyl ester which can be prepared from the corresponding commercially available acid (20d), e.g. by treatment with di-tert-butyl dicarbonate in the presence of a base like dimethylaminopyridine. Intermediate (20e) is treated with a base such as lithium diisopropyl amide in a solvent like tetrahydrofuran, and reacted with (20c) to give the alkenyl diester (20f). Cyclisation of (20f) by an olefin metathesis reaction, performed as described above, provides cyclopentene derivative (20g). Stereoselective epoxidation of (20g) can be carried out using the Jacobsen asymmetric epoxidation method to obtain epoxide (20h). Finally, an epoxide opening reaction under basic conditions, e.g. by addition of a base, in particular DBN (1,5-diazabicyclo-[4.3.0]non-5-ene), yields the alcohol (20i). Optionally, the double bond in intermediate (20i) can be reduced, for example by catalytic hydrogenation using a catalyst like palladium on carbon, yielding the corresponding cyclopentane compound. The t.butyl ester may be removed to the corresponding acid, which subsequently is coupled to a P1 building block.

The -L-$R^4$ group can be introduced on the pyrrolidine, cyclopentane or cyclopentene rings at any convenient stage of the synthesis of the compounds according to the present invention. One approach is to first introduce the -L-$R^4$ group to the said rings and subsequently add the other desired building blocks, i.e. P1 (optionally with the P1' tail) and P3, followed by the macrocycle formation. Another approach is to couple the building blocks P2, bearing no -L-$R^4$ substituent, with each P1 and P3, and to add the -L-$R^4$ group either before or after the macrocycle formation. In the latter procedure, the P2 moieties have a hydroxy group, which may be protected by a hydroxy protecting group $PG^1$.

The -L-$R^4$-groups can be introduced on building blocks P2 by reacting hydroxy substituted intermediates (21a) or (21d)

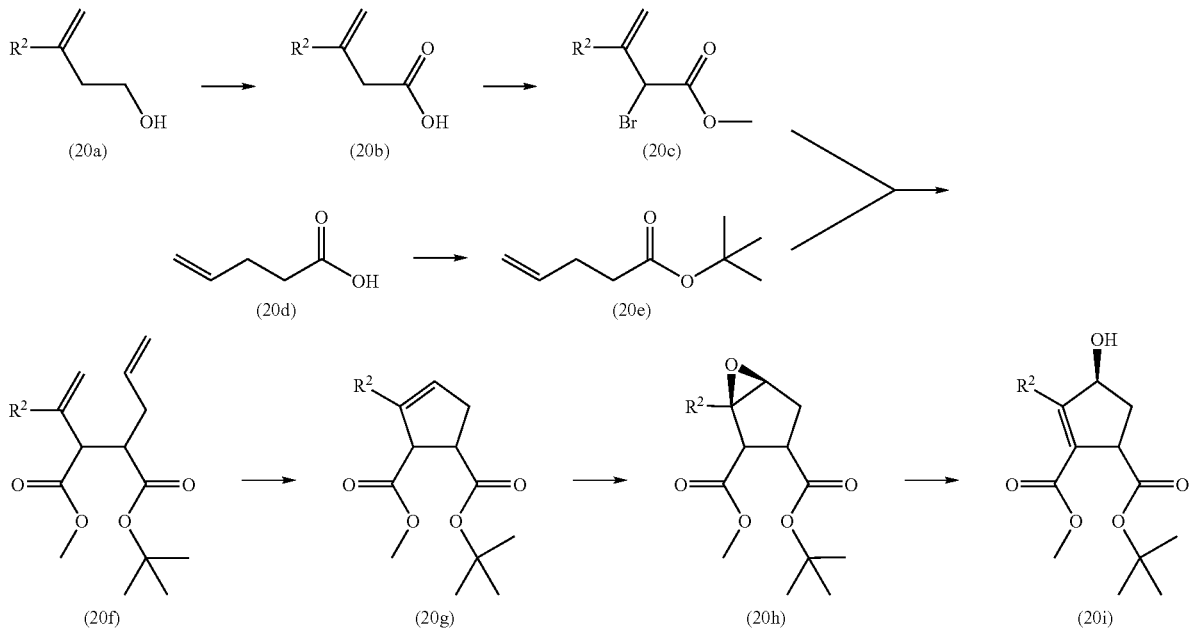

with intermediates (4b)-(4f) as described above for the synthesis of (I) starting from (4a). These reactions are represented in the schemes below, wherein $L^2$ is as specified above and $L^5$ and $L^{5a}$ independently from one another, represent hydroxy, a carboxyl protecting group -OPG$^2$ or -OPG$^{2a}$, or L may also represent a P1 group such as a group (d) or (e) as specified above, or $L^{5a}$ may also represent a P3 group such as a group (b) as specified above The groups PG$^2$ and PG are as specified above. Where the groups $L^5$ and $L^{5a}$ are PG or PG$^{2a}$, they are chosen such that each group is selectively cleavable towards the other. For example, one of $L^5$ and $L^{5a}$ may be a methyl or ethyl group and the other a benzyl or t.butyl group.

In one embodiment in (21a), $L^2$ is PG and $L^5$ is -OPG$^2$, or in (21d), $L^{5a}$ is -OPG$^2$ and $L^5$ is -OPG$^2$ and the PG$^2$ groups are removed as described above.

such as NaOH, in particular with LiOH. In another embodiment, hydroxy substituted cyclopentane or cyclopentene analogs (21d) are converted to (21e), which, where $L^5$ and L are -OPG or -OPG may be converted to the corresponding acids (21f) by removal of the group PG$^2$. Removal of PG$^{2a}$ in (21e-1) leads to similar intermediates.

Intermediates (4b), which are isoquinoline derivatives, can be prepared using art-known procedures. For example, US 2005/0143316 provides diverse methods for the synthesis of isoquinolines as R$^4$—OH or R$^4$-LG intermediates. Methodology for the synthesis of such isoquinolines has been described by N. Briet et al., Tetrahedron, 2002, 5761 and is shown below, wherein R$^{4a}$, R$^{4b}$ and R$^{4b'}$ are substituents on the isoquinoline moiety having the meanings defined herein for the substituents on the R$^4$-group.

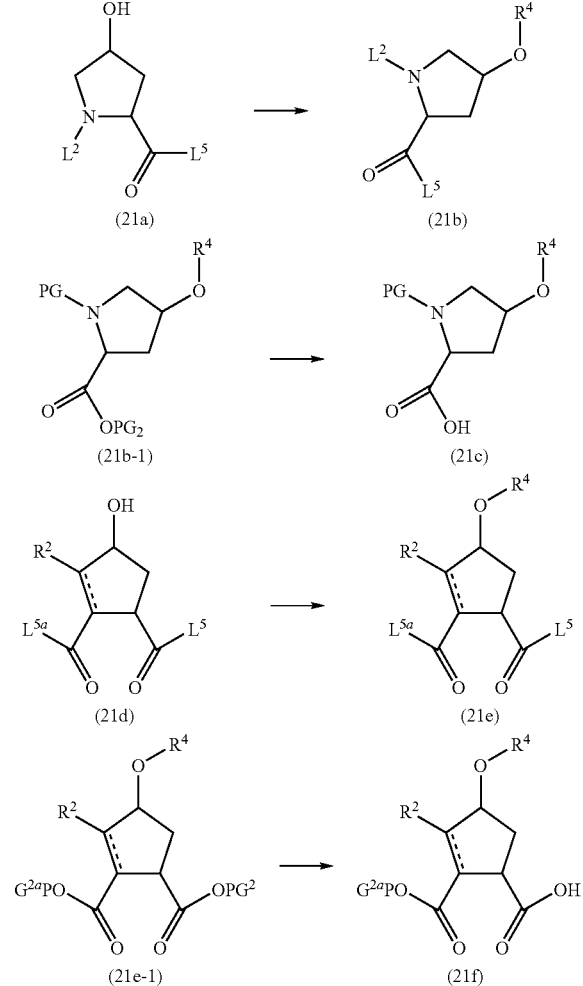

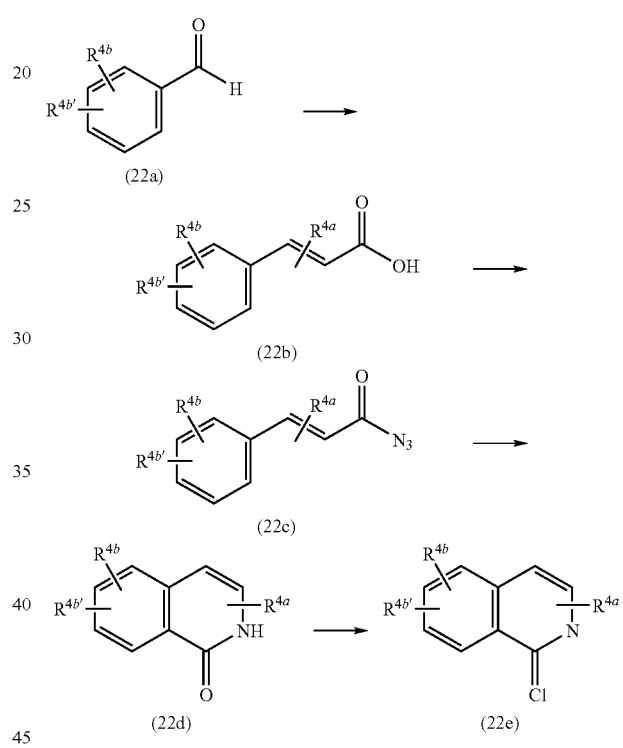

In another embodiment the group $L^2$ is BOC, $L^5$ is hydroxy and the starting material (21a) is commercially available BOC-hydroxyproline, or any other stereoisomeric form thereof, e.g. BOC-L-hydroxyproline, in particular the trans isomer of the latter. Where $L^5$ in (21b) is a carboxyl-protecting group, it may be removed following procedures described above to (21c). In still another embodiment PG in (21b-1) is Boc and PG$^2$ is a lower alkyl ester, in particular a methyl or ethyl ester. Hydrolysis of the latter ester to the acid can be done by standard procedures, e.g. acid hydrolysis with hydrochloric acid in methanol or with an alkali metal hydroxide Cinnamic acid derivatives (22b) are converted to 1-chloroisoquinolines in a three-step process. The resulting chloroisoquinolines (22e) can be subsequently coupled to hydroxypyrrolidine, hydroxycyclopentane or hydroxycyclopentene derivatives as described herein. In a first step, the carboxyl group in the cinnamic acids (22b) is activated, for example by treatment with a $C_{1-6}$alkyl (in particular methyl or ethyl) chloroformate in the presence of a base. The resulting mixed anhydrides are then treated with sodium azide yielding the acyl azides (22c). Several other methods are available for the formation of acylazides from carboxylic acids, for example the carboxylic acid can be treated with diphenylphosphorylazide (DPPA) in an aprotic solvent such as methylene chloride, in the presence of a base. In a next step the acyl azides (22c) are converted to the corresponding isoquinolones (22d) in particular by heating the acylazides in a high boiling solvent such as diphenylether. The starting cinnamic acids (22d) are commercially available or can be obtained from the corresponding benzaldehydes (22a) by direct condensation with malonic acids or derivatives thereof, or by employing a Wittig reaction. The intermediate isoquinolones (22d) can be converted to the corresponding 1-chloro-isoquinolines by treatment with a halogenating agent such as phosphorous oxychloride.

$R^4$-groups which are isoquinolines can also be prepared following procedures as described in K. Hirao, R. Tsuchiya, Y. Yano, H. Tsue, Heterocycles 42(1) 1996, 415-422.

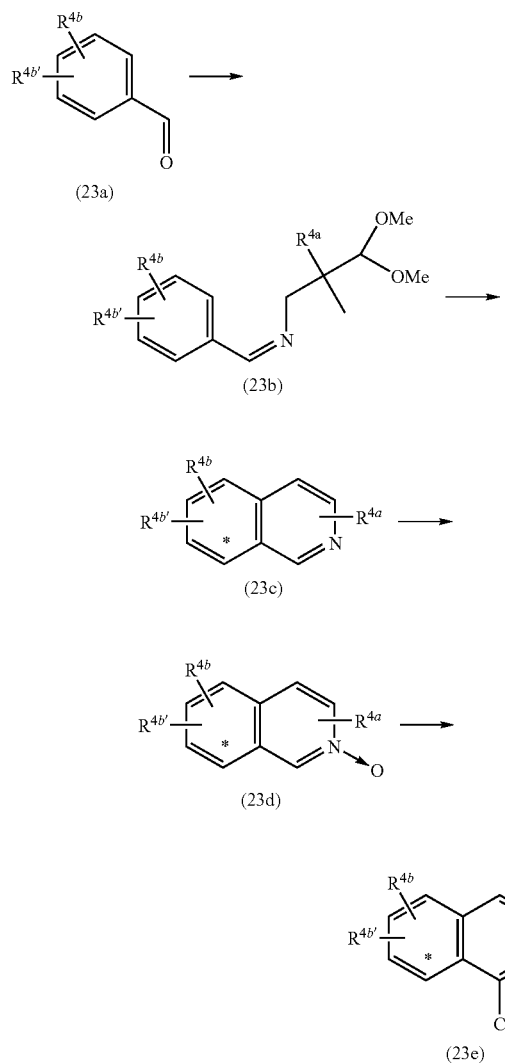

An alternative method for the synthesis of the isoquinoline ring system is the Pomeranz-Fritsh procedure. This method begins with the conversion of a benzaldehyde derivative (23a) to a functionalized imine (23b), which then is converted to an isoquinoline ring system by treatment with acid at elevated temperature. This method is particularly useful for preparing isoquinoline intermediates that are substituted at the C8 position indicated by the asterisk. The intermediate isoquinolines (23c) can be converted to the corresponding 1-chloroquinolines (23e) in a two-step process. The first step comprises the formation of an isoquinoline N-oxide (23d) by treatment of isoquinoline (23c) with a peroxide such as meta-chloroperbenzoic acid in an appropriate solvent such as dichloromethane. Intermediate (23d) is converted to the corresponding 1-chloroisoquinoline by treatment with a halogenating agent such as phosphorous oxychloride.

Another method for the synthesis of the isoquinoline ring system is shown in the scheme below.

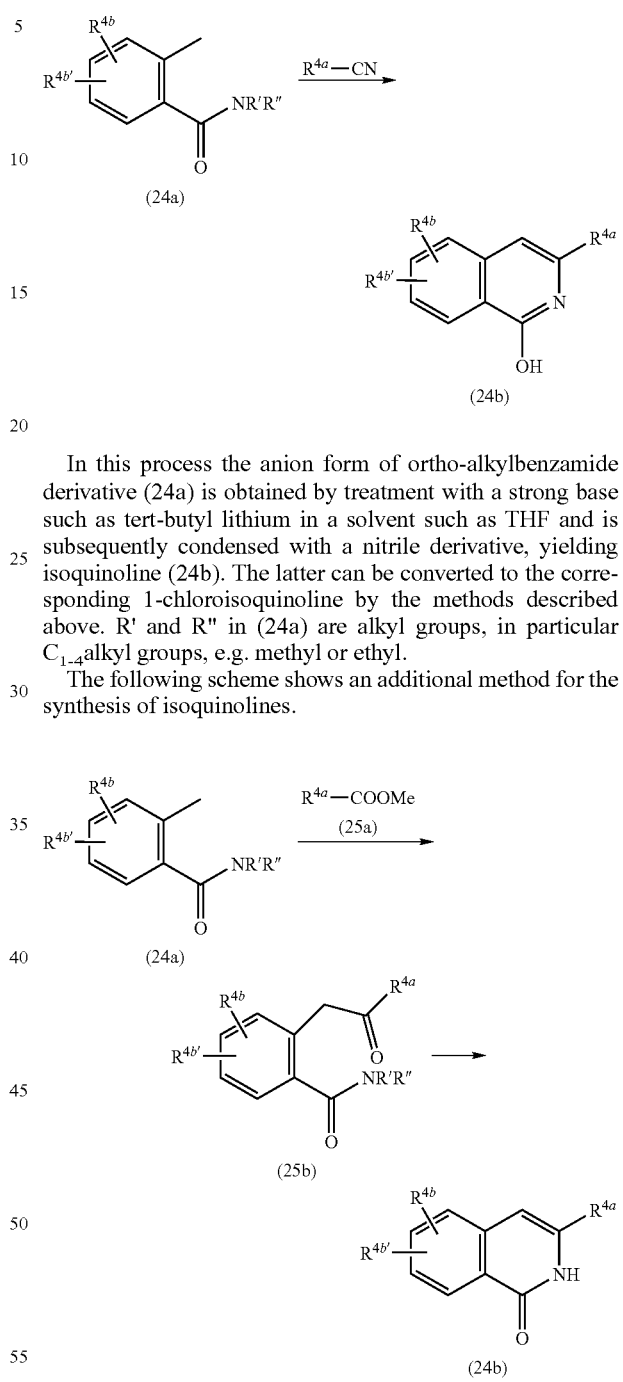

In this process the anion form of ortho-alkylbenzamide derivative (24a) is obtained by treatment with a strong base such as tert-butyl lithium in a solvent such as THF and is subsequently condensed with a nitrile derivative, yielding isoquinoline (24b). The latter can be converted to the corresponding 1-chloroisoquinoline by the methods described above. R' and R" in (24a) are alkyl groups, in particular $C_{1-4}$ alkyl groups, e.g. methyl or ethyl.

The following scheme shows an additional method for the synthesis of isoquinolines.

Intermediate (24a) is deprotonated using a strong base as described above. R' and R" are as specified above. The resulting intermediate anion is condensed with an ester (25a), obtaining ketone intermediate (25b). In a subsequent reaction the latter intermediate (25b) is reacted with ammonia or an ammonium salt, e.g. ammonium acetate, at elevated temperature, resulting in the formation of isoquinolone (24b).

A variety of carboxylic acids with the general structure (25a) can be used in the above synthesis. These acids are available either commercially or can be prepared via art-known procedures. An example of the preparation of 2-(substituted)aminocarboxy-aminothiazole derivatives (25a-1), following the procedure described by Berdikhina et al. in Chem. Heterocycl. Compd. (Engl. Transl.) (1991), 427-433, is shown in the following reaction scheme which illustrates the preparation of 2-carboxy-4-isopropyl-thiazole (25c-1):

dichloromethane followed by removal of the tert-butyl group under acidic conditions. Subsequent condensation of thiourea derivative (27c) with 3-bromopyruvic acid provides the thiazole carboxylic acid (25a-2).

Yet an additional method for the preparation of isoquinolines is illustrated in the following reaction scheme.

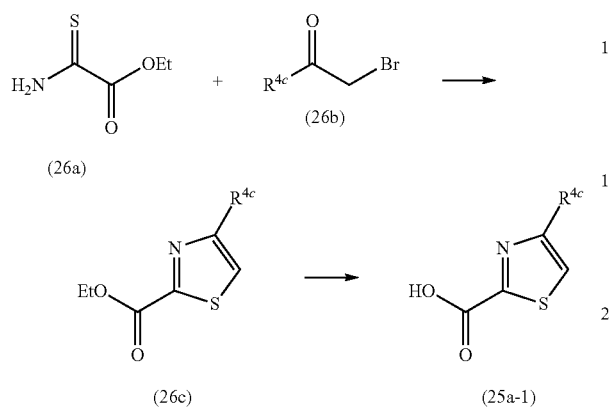

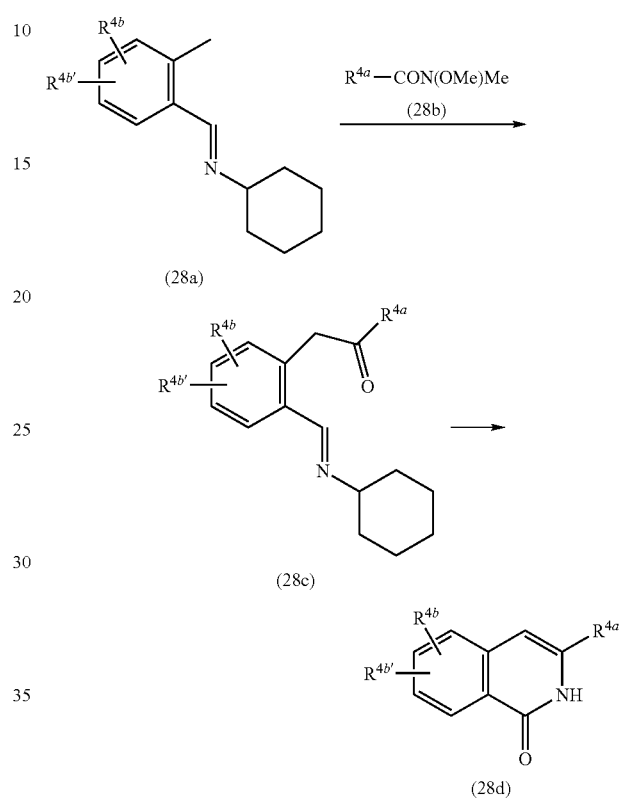

Ethyl thiooxamate (26a) is reacted with the β-bromoketone (26b) to form the thiazolyl carboxylic acid ester (26c) which is hydrolyzed to the corresponding acid (25a-1). The ethyl ester in these intermediates may be replaced by other carboxyl protecting groups $PG^2$, as defined above. In the above scheme $R^{4c}$ is as defined above and in particular is $C_{1-4}$alkyl, more in particular i.propyl.

The bromoketone (26b) may be prepared from 3-methylbutan-2-one (MIK) with a sililating agent (such as TMSCl) in the presence of a suitable base (in particular LiHMDS) and bromine.

The synthesis of further carboxylic acids (25a), in particular of substituted amino thiazole carboxylic acids (25a-2) is illustrated herebelow:

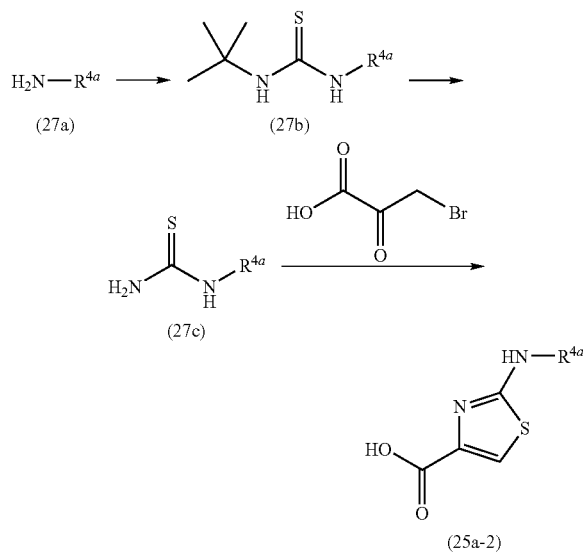

Thiourea (27c) with various substituents $R^{4a}$, which in particular are $C_{1-6}$alkyl, can be formed by reaction of the appropriate amine (27a) with tert-butylisothiocyanate in the presence of a base like diisopropylethylamine in a solvent like In the first step of this process an ortho-alkylarylimine derivative (28a) is subjected to deprotonation conditions (e.g. sec-butyl lithium, THF) and the resulting anion is condensed with an activated carboxylic acid derivative such as a Weinreb amide (28b). The resulting keto imine (28c) is converted to the isoquinoline (28d) by condensation with ammonium acetate at elevated temperatures. The thus obtained isoquinolines can be converted to the corresponding 1-chloroisoquinolines by the methods described herein.

The isoquinolines described herein, either as such or incorporated onto the hydroxy-pyrrolidine, hydroxycyclopentane or hydroxycyclopentane moieties in the compounds of formula (I) or in any of the intermediates mentioned herein, can be further functionalized. An example of such functionalization is illustrated herebelow.

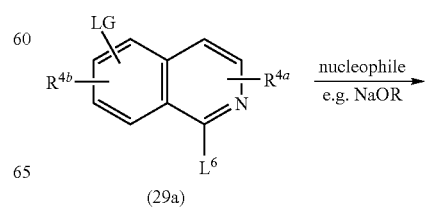

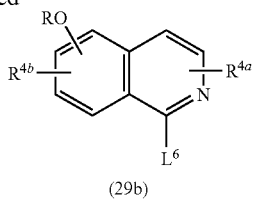

(29b)

The above scheme shows the conversion of a 1-chloro-6-fluoro-isoquinoline to the corresponding 1-chloro-6-$C_{1-6}$alkoxy-isoquinoline moiety (29b), by treatment of (29a) with a sodium or potassium alkoxide in an alcohol solvent from which the alkoxide is derived. $L^6$ in the above scheme represents halo or a group

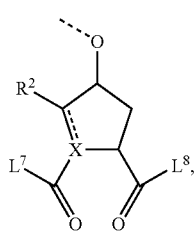

R in the above scheme represents $C_{1-6}$alkyl and LG is a leaving group. In one embodiment LG is fluoro. $L^7$ and $L^8$ represent various substituents that can be linked at these positions of the P2 moiety, in particular groups such as $OL^5$, or $L^8$ may be a P1 group and $L^7$ a P3 group, or $L^7$ and $L^8$ taken together may form the remainder of the macrocyclic ring system of the compounds of formula (I).

The following scheme provides an example for the modification of isoquinolines by Suzuki reactions. These couplings can be employed to functionalize an isoquinoline at each position of the ring system provided said ring is suitably activated or functionalized, as for example with chloro.

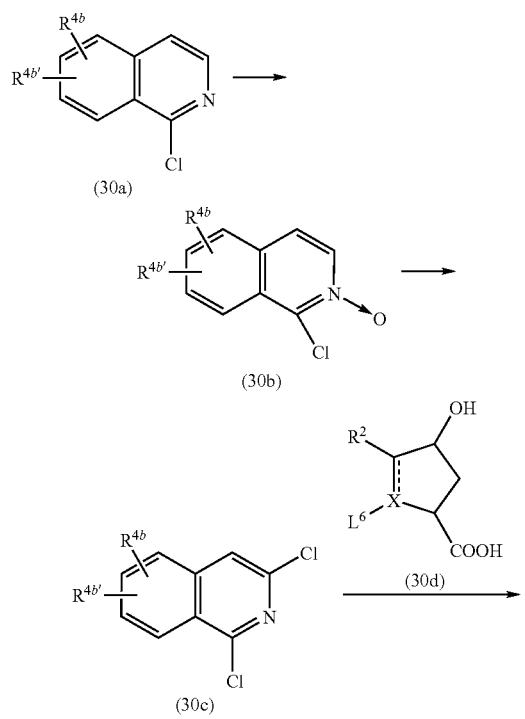

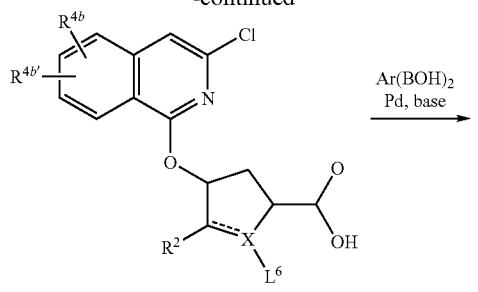

(30e)

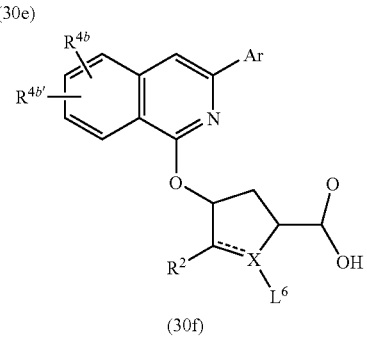

(30f)

This sequence begins with 1-chloroisoquinoline (30a) which upon treatment with a peroxide such as metachloroperbenzoic acid is converted to the corresponding N-oxide (30b). The latter intermediate is converted to the corresponding 1,3-dichloro-isoquinoline (30c) by treatment with a halogenating agent, e.g. phosphorous oxychloride. Intermediate (30c) can be coupled with an intermediate (30d), wherein $L^6$ is a group PG where X is N, or $L^6$ is a group —$COOPG^2$ where X is C, using methods described herein for introducing —O—$R^4$-groups, to provide intermediate (30e). Intermediate (30e) is derivatized using a Suzuki coupling with an aryl boronic acid, in the presence of a palladium catalyst and a base, in a solvent such as THF, toluene or a dipolar aprotic solvent such as DMF, to provide the C3-arylisoquinoline intermediate (30f). Heteroarylboronic acids can also be employed in this coupling process to provide C3-heteroarylisoquinolines.

Suzuki couplings of isoquinolines systems with aryl or heteroaryl groups can also be employed at a later synthesis stage in the preparation of compounds of formula (I). The isoquinoline ring systems can also be functionalized by employing other palladium catalyzed reactions, such as the Heck, Sonogashira or Stille couplings as illustrated for example in US 2005/1043316.

Compounds of the present invention, or intermediates containing a P2 building block or the building blocks P2 themselves, wherein a heterocyclic $R^4$ group is attached via a ring nitrogen directly to the pyrrolidine or cyclopentane/cyclopentene rings, i.e. L is a direct bond, in one embodiment can be prepared by a replacement reaction wherein a suitable leaving group LG on the pyrrolidine or cyclopentane/cyclopentene ring is replaced by the desired $R^4$ group, in particular a nitrogen-containing cyclic group. Examples of the latter comprise tetrazole, triazole, imidazole and pyrrole groups. In one procedure the hydroxy function on the pyrrolidine or cyclopentane/cyclopentene moieties such as in intermediates (4a), (6d), (8c), (10c) or (17e), is reacted with a leaving group introducing reagent, such as with a halogenating agent, for example phosphoryl chloride or the like, or with an alkyl or arylsulfonyl chloride, e.g. with tosyl, mesyl, brosyl, triflyl chloride. The thus formed intermediate is then reacted with a heterocycle having a ring nitrogen substituted with hydrogen (i.e. N—H). In another procedure, the building blocks P1, P2 and P3 or building blocks P1 and P2 are assembled and cyclized, wherein the P2 building block has a pyrrolidine or cyclopentane/cyclopentene moiety substituted with hydroxy, to precursors of the compounds of formula (I), wherein the hydroxy group is converted into a leaving group and reacted with a N-containing heterocycle, similarly as described above.

Alternatively the $R^4$ group can be introduced by a Mitsunobu reaction wherein the hydroxy group of the pyrrolidine or cyclopentane/ene ring is reacted with a nitrogen atom from the heterocyclic $R^4$ group.

Compounds of formula (I) wherein L is a direct bond and $R^4$ is a ring system connected to the pyrrolidine or cyclopentane/ene moiety via a carbon atom can be prepared by building up the ring starting from the same hydroxy intermediates mentioned above. Again, this can either be done at the building block stage or after assembling and cyclizing the building blocks. For example, the hydroxy function may be converted into a leaving group, which in turn is substituted by a cyano group. This cyano group in turn can be further converted into the desired heterocycles. For example, compounds wherein a tetrazole derivative is attached through a carbon atom of the tetrazolic ring can be prepared by building up the tetrazole moiety directly onto the pyrrolidine- or cyclopentane/ene-ring precursor. This can be achieved for instance by transforming the hydroxy group of the nitrogen-ring precursor into a cyano group followed by reaction with an azide reagent like sodium azide. Triazole derivatives can also be built up directly onto the nitrogen-ring precursor for example by transforming the hydroxy group of the nitrogen-ring precursor into an azide group followed by a 3+2 cycloaddition reaction of the obtained azide with a suitable alkyne derivative.

Structurally diverse tetrazoles for use in the above described substitution or Mitsunobu reactions can be prepared by reacting various nitrile compounds, either commercially available or easily synthesized, with sodium azide. Triazole derivatives can be prepared by reaction of an alkyne compound with trimethylsilyl azide. Useful alkyne compounds are either commercially available or they can be prepared for instance according to a Sonogashira reaction, i.e. reaction of a primary alkyne, an aryl halide and triethylamine in the presence of $PdCl_2(PPh)_3$ and CuI as described for example in A. Elangovan, Y.-H. Wang, T.-I. Ho, *Org. Lett.*, 2003, 5, 1841-1844. The heterocyclic substituent can also be modified when attached to the P2 building block either before or after coupling of the P2 building block to the other building blocks.

Further alternatives for the preparation of compounds or intermediates wherein L is a bond and $R^4$ is an optionally substituted heterocycle can be found for example in WO 2004/072243.

Synthesis of P1 Building Blocks

The cyclopropane amino acid used in the preparation of the P1 fragment is commercially available or can be prepared using art-known procedures.

In particular the amino-vinyl-cyclopropyl ethyl ester (12b) may be obtained according to the procedure described in WO 00/09543 or as illustrated in the following scheme, wherein $PG^2$ is a carboxyl protecting group as specified above:

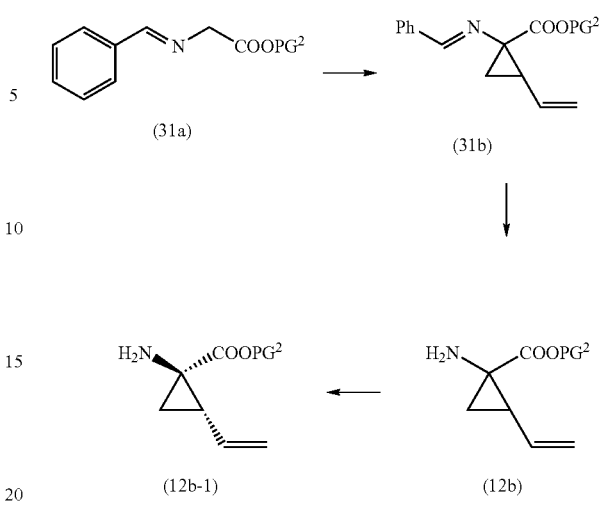

Treatment of commercially available or easily obtainable imine (31a) with 1,4-dihalo-butene in presence of a base produces (31b), which after hydrolysis yields cyclopropyl amino acid (12b), having the allyl substituent syn to the carboxyl group. Resolution of the enantiomeric mixture (12b) results in (12b-1). The resolution is performed using art-known procedures such as enzymatic separation; crystallization with a chiral acid; or chemical derivatization; or by chiral column chromatography. Intermediates (12b) or (12b-1) may be coupled to the appropriate proline derivatives as described above.

P1 building blocks for the preparation of compounds according to general formula (I) wherein $R^1$ is —$OR^5$ or —NH—$SO_2R^6$ can be prepared by reacting amino acids (32a) with the appropriate alcohol or amine respectively under standard conditions for ester or amide formation. Cyclopropyl amino acids (32a) are prepared by introducing a N-protecting group PG, and removal of $PG^2$ and the amino acids (32a) are converted to the amides (12c-1) or esters (12c-2), which are subgroups of the intermediates (12c), as outlined in the following reaction scheme, wherein PG is as specified above.

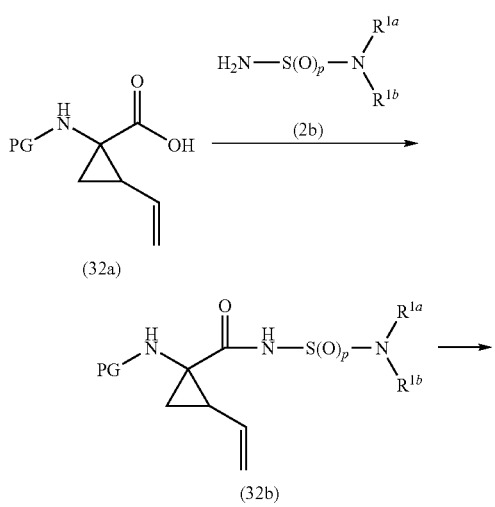

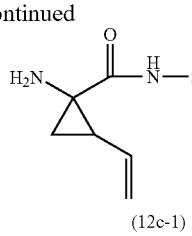

(12c-1)

The reaction of (32a) with amine (2b) is an amide forming procedure and can be performed following the procedures described above. This reaction yields intermediates (32b) from which the amino protecting group is removed by standard methods such as those described above. This in turn results in the desired intermediate (12c-1). Starting materials (32a) may be prepared from the above mentioned intermediates (12b) by first introducing a N-protecting group PG and subsequent removal of the group $PG^2$.

In one embodiment the reaction of (32a) with (2b) is done by treatment of the amino acid with a coupling agent, for example N,N'-carbonyl-diimidazole (CDI) or the like, in a solvent like THF followed by reaction with (2b) in the presence of a base such as 1,8-diazabicyclo[5.4.0]undec-7-ene (DBU). Alternatively the amino acid can be treated with (2b) in the presence of a base like diisopropylethylamine followed by treatment with a coupling agent such as benzotriazole-1-yl-oxy-tris-pyrrolidino-phosphonium hexafluorophosphate (commercially available as PyBOP®) to effect the introduction of the sulfonamide group.

Intermediates (12c-1) in turn may be coupled to the appropriate proline, cyclopentane or cyclopentene derivatives as described above.

Synthesis of P1' Fragments

The $—R^1$ fragments (also referred to as P1' fragments) can be prepared using art-known procedures or as shown herebelow.

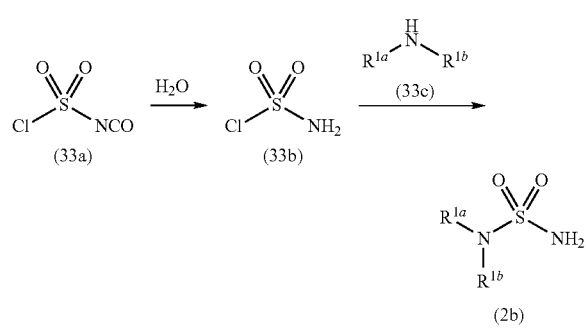

Intermediates of formula (2b) may be prepared by a two-step process using chlorosulfonylisocyanate (33a) as starting material. Said isocyanate (33a) can be hydrolyzed to the corresponding chlorosulfamoyl chloride (33b) by treatment with water in a suitable solvent such as DMA, DMF, 1-methyl-2-pyrrolidinone, dichloro-methane, chloroform, ethers such as tetrahydrofuran, 1,4-dioxane, glyme and diglyme, and alcohols such as methanol, ethanol or tert-butanol. The sulfamoylchloride (6b) upon treatment with the appropriate amine (6c), in the presence of a base, provides the desired sulfamide derivative (2b).

Compounds of formula (2b) may as well be prepared from a sulfamide in the presence of a suitable solvent. Preparation of the sulfamide moieties (2b) is also illustrated in the following references:

E. Cohen, B. Klarberg; J. Am. Chem. Soc., 1962, 84, 1994.
G. Weiss, G. Schulze, Liebigs Ann. Chem., 1969, 729, 40.
R. Graf, Chem. Ber., 1959, 92, 509.
J. A. Kloek, K. L. Leschinsky, J. Org. Chem., 1976, 41, 4028.
R. E. Olson, T. M. Sielecki, et al; J. Med. Chem., 1999; 42, 1178.
R. P. Dickinson, K. N. Dack, et al; J. Med. Chem., 1997; 40, 3442.
M. J. Tozer, I. M. Buck et al.; Bioorg. Med. Chem. Leff., 1999, 9, 3103. G. Dewynter et al.; Tetrahedron, 1993, 49, 65.
WO-02/53557 (Actelion Pharmaceuticals Ltd.).

The sulfamide derivative is coupled to a cyclopropyl amino acid, such as (32a) as described above.

Alternatively, the sulfamide group can be introduced at a later stage of the synthesis, for example at the last step. In this case an amino acid having an unprotected amino function and a protected acid function, is coupled to the acid function of the P2 building block using the conditions for amide bond formation as described above. Removal of the acid protecting group, using the appropriate conditions for the protecting group used, followed by coupling of the sulfamide as described above, yields intermediates such as (12e-1), (13c) and (14d).

Synthesis of the P3 Building Blocks

The P3 building blocks are available commercially or can be prepared according to methodologies known to the skilled in the art. One of these methodologies is shown in the scheme below and uses monoacylated amines, such as trifluoroacetamide or a Boc-protected amine.

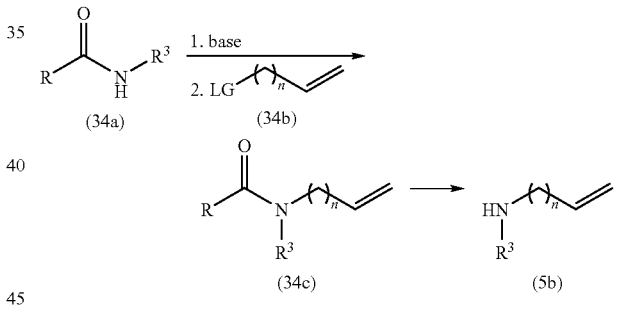

In the above scheme, R together with the CO group forms a N-protecting group, in particular R is t-butoxy, trifluoromethyl; $R^3$ and n are as defined above and LG is a leaving group, in particular halogen, e.g. chloro or bromo.

The monoacylated amines (34a) are treated with a strong base such as sodium hydride and are subsequently reacted with a reagent $LG-C_{5-8}$alkenyl (34b), in particular halo$C_{5-8}$alkenyl, to form the corresponding protected amines (34c). Deprotection of (34c) affords (5b), which are building blocks P3. Deprotection will depend on the functional group R, thus if R is t-butoxy, deprotection of the corresponding Boc-protected amine can be accomplished with an acidic treatment, e.g. trifluoroacetic acid.

Alternatively, when R is for instance trifluoromethyl, removal of the R group is accomplished with a base, e.g. sodium hydroxide.

The following scheme illustrates yet another method for preparing a P3 building block, namely a Gabriel synthesis of primary $C_{5-8}$alkenylamines, which can be carried out by the treatment of a phthalimide (35a) with a base, such as NaOH or KOH, and with (34b), which is as specified above, followed by hydrolysis of the intermediate N-alkenyl imide to generate a primary $C_{5-8}$alkenylamine (5b-1).

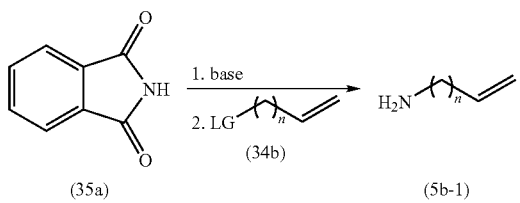

In the above scheme, n is as defined above.

Compounds of formula (I) may be converted into each other following art-known functional group transformation reactions. For example, amino groups may be N-alkylated, nitro groups reduced to amino groups, a halo atom may be exchanged for another halo.

The compounds of formula (I) may be converted to the corresponding N-oxide forms following art-known procedures for converting a trivalent nitrogen into its N-oxide form. Said N-oxidation reaction may generally be carried out by reacting the starting material of formula (I) with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarbo-peroxoic acid or halo substituted benzenecarboperoxoic acid, e.g. 3-chlorobenzene-carboperoxoic acid, peroxoalkanoic acids, e.g. peroxoacetic acid, alkylhydroperoxides, e.g. tert-butyl hydro-peroxide. Suitable solvents are, for example, water, lower alcohols, e.g. ethanol and the like, hydrocarbons, e.g. toluene, ketones, e.g. 2-butanone, halogenated hydrocarbons, e.g. dichloromethane, and mixtures of such solvents.

Pure stereochemically isomeric forms of the compounds of formula (I) may be obtained by the application of art-known procedures. Diastereomers may be separated by physical methods such as selective crystallization and chromatographic techniques, e.g., counter-current distribution, liquid chromatography and the like.

The compounds of formula (I) may be obtained as racemic mixtures of enantiomers which can be separated from one another following art-known resolution procedures. The racemic compounds of formula (I), which are sufficiently basic or acidic may be converted into the corresponding diastereomeric salt forms by reaction with a suitable chiral acid, respectively chiral base. Said diastereomeric salt forms are subsequently separated, for example, by selective or fractional crystallization and the enantiomers are liberated therefrom by alkali or acid. An alternative manner of separating the enantiomeric forms of the compounds of formula (I) involves liquid chromatography, in particular liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound may be synthesized by stereospecific methods of preparation. These methods may advantageously employ enantiomerically pure starting materials.

In a further aspect, the present invention concerns a pharmaceutical composition comprising a therapeutically effective amount of a compound of formula (I) as specified herein, or a compound of any of the subgroups of compounds of formula (I) as specified herein, and a pharmaceutically acceptable carrier. A therapeutically effective amount in this context is an amount sufficient to prophylactically act against, to stabilize or to reduce viral infection, and in particular HCV viral infection, in infected subjects or subjects being at risk of being infected. In still a further aspect, this invention relates to a process of preparing a pharmaceutical composition as specified herein, which comprises intimately mixing a pharmaceutically acceptable carrier with a therapeutically effective amount of a compound of formula (I), as specified herein, or of a compound of any of the subgroups of compounds of formula (I) as specified herein.

Therefore, the compounds of the present invention or any subgroup thereof may be formulated into various pharmaceutical forms for administration purposes. As appropriate compositions there may be cited all compositions usually employed for systemically administering drugs. To prepare the pharmaceutical compositions of this invention, an effective amount of the particular compound, optionally in addition salt form or metal complex, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, particularly, for administration orally, rectally, percutaneously, or by parenteral injection. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, lubricants, binders, disintegrating agents and the like in the case of powders, pills, capsules, and tablets. Because of their ease in administration, tablets and capsules represent the most advantageous oral dosage unit forms, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations which are intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin.

The compounds of the present invention may also be administered via oral inhalation or insufflation by means of methods and formulations employed in the art for administration via this way. Thus, in general the compounds of the present invention may be administered to the lungs in the form of a solution, a suspension or a dry powder, a solution being preferred. Any system developed for the delivery of solutions, suspensions or dry powders via oral inhalation or insufflation are suitable for the administration of the present compounds.

Thus, the present invention also provides a pharmaceutical composition adapted for administration by inhalation or insufflation through the mouth comprising a compound of formula (I) and a pharmaceutically acceptable carrier. Preferably, the compounds of the present invention are administered via inhalation of a solution in nebulized or aerosolized doses.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, suppositories, powder packets, wafers, injectable solutions or suspensions and the like, and segregated multiples thereof.

The compounds of formula (I) show antiviral properties. Viral infections and their associated diseases treatable using the compounds and methods of the present invention include those infections brought on by HCV and other pathogenic flaviviruses such as Yellow fever, Dengue fever (types 1-4), St. Louis encephalitis, Japanese encephalitis, Murray valley encephalitis, West Nile virus and Kunjin virus. The diseases associated with HCV include progressive liver fibrosis, inflammation and necrosis leading to cirrhosis, end-stage liver disease, and HCC; and for the other pathogenic flaviviruses the diseases include yellow fever, dengue fever, hemorrhagic fever and encephalitis. A number of the compounds of this invention moreover are active against mutated strains of HCV. Additionally, many of the compounds of this invention show a favorable pharmacokinetic profile and have attractive properties in terms of bioavailabilty, including an acceptable half-life, AUC (area under the curve) and peak values and lacking unfavorable phenomena such as insufficient quick onset and tissue retention.

The in vitro antiviral activity against HCV of the compounds of formula (I) was tested in a cellular HCV replicon system based on Lohmann et al. (1999) Science 285:110-113, with the further modifications described by Krieger et al. (2001) Journal of Virology 75: 4614-4624, which is further exemplified in the examples section. This model, while not a complete infection model for HCV, is widely accepted as the most robust and efficient model of autonomous HCV RNA replication currently available. Compounds exhibiting anti-HCV activity in this cellular model are considered as candidates for further development in the treatment of HCV infections in mammals. It will be appreciated that it is important to distinguish between compounds that specifically interfere with HCV functions from those that exert cytotoxic or cytostatic effects in the HCV replicon model, and as a consequence cause a decrease in HCV RNA or linked reporter enzyme concentration. Assays are known in the field for the evaluation of cellular cytotoxicity based for example on the activity of mitochondrial enzymes using fluorogenic redox dyes such as resazurin. Furthermore, cellular counter screens exist for the evaluation of non-selective inhibition of linked reporter gene activity, such as firefly luciferase. Appropriate cell types can be equipped by stable transfection with a luciferase reporter gene whose expression is dependent on a constitutively active gene promoter, and such cells can be used as a counter-screen to eliminate non-selective inhibitors.

Due to their antiviral properties, particularly their anti-HCV properties, the compounds of formula (I) or any subgroup thereof, their prodrugs, N-oxides, addition salts, quaternary amines, metal complexes and stereochemically isomeric forms, are useful in the treatment of individuals experiencing a viral infection, particularly a HCV infection, and for the prophylaxis of these infections. In general, the compounds of the present invention may be useful in the treatment of warm-blooded animals infected with viruses, in particular flaviviruses such as HCV.

The compounds of the present invention or any subgroup thereof may therefore be used as medicines. Said use as a medicine or method of treatment comprises the systemic administration to viral infected subjects or to subjects susceptible to viral infections of an amount effective to combat the conditions associated with the viral infection, in particular the HCV infection.

The present invention also relates to the use of the present compounds or any subgroup thereof in the manufacture of a medicament for the treatment or the prevention of viral infections, particularly HCV infection.

The present invention furthermore relates to a method of treating a warm-blooded animal infected by a virus, or being at risk of infection by a virus, in particular by HCV, said method comprising the administration of an anti-virally effective amount of a compound of formula (I), as specified herein, or of a compound of any of the subgroups of compounds of formula (I), as specified herein.

Also, the combination of previously known anti-HCV compound, such as, for instance, interferon-α (IFN-α), pegylated interferon-α and/or ribavirin, and a compound of formula (I) can be used as a medicine in a combination therapy. The term "combination therapy" relates to a product containing mandatory (a) a compound of formula (I), and (b) optionally another anti-HCV compound, as a combined preparation for simultaneous, separate or sequential use in treatment of HCV infections, in particular, in the treatment of infections with HCV.

Anti-HCV compounds encompass agents selected from an HCV polymerase inhibitor, an HCV protease inhibitor, an inhibitor of another target in the HCV life cycle, and immunomodulatory agent, an antiviral agent, and combinations thereof.

HCV polymerase inhibitors include, but are not limited to, NM283 (valopicitabine), R803, JTK-109, JTK-003, HCV-371, HCV-086, HCV-796 and R-1479.

Inhibitors of HCV proteases (NS2-NS3 inhibitors and NS3-NS4A inhibitors) include, but are not limited to, the compounds of WO02/18369 (see, e.g., page 273, lines 9-22 and page 274, line 4 to page 276, line 11); BILN-2061, VX-950, GS-9132 (ACH-806), SCH-503034, and SCH-6. Further agents that can be used are those disclosed in WO-98/17679, WO-00/056331 (Vertex); WO 98/22496 (Roche); WO 99/07734, (Boehringer Ingelheim), WO 2005/073216, WO2005073195 (Medivir) and structurally similar agents.

Inhibitors of other targets in the HCV life cycle, including NS3 helicase; metalloprotease inhibitors; antisense oligonucleotide inhibitors, such as ISIS-14803, AVI-4065 and the like; siRNA's such as SIRPLEX-140-N and the like; vector-encoded short hairpin RNA (shRNA); DNAzymes; HCV specific ribozymes such as heptazyme, RPI.13919 and the like; entry inhibitors such as HepeX-C, HuMax-HepC and the like; alpha glucosidase inhibitors such as celgosivir, UT-231B and the like; KPE-02003002; and BIVN 401.

Immunomodulatory agents include, but are not limited to; natural and recombinant interferon isoform compounds, including α-interferon, β-interferon, γ-interferon, ω-interferon and the like, such as Intron A®, Roferon-A®, Canferon-A300R®, Advaferon®, Infergen®, Humoferon®, Sumiferon MP®, Alfaferone®, IFN-beta®, Feron® and the like; polyethylene glycol derivatized (pegylated) interferon compounds, such as PEG interferon-α-2a (Pegasys®), PEG interferon-α-2b (PEG-Intron®), pegylated IFN-α-con1 and the like; long acting formulations and derivatizations of interferon compounds such as the albumin-fused interferon albuferon α and the like; compounds that stimulate the synthesis of interferon in cells, such as resiquimod and the like; interleukins; compounds that enhance the development of type 1 helper T cell response, such as SCV-07 and the like; TOLL-like receptor agonists such as CpG-10101 (actilon), isatoribine and the like; thymosin α-1; ANA-245; ANA-246; histamine dihydrochloride; propagermanium; tetrachlorodecaoxide; ampligen; IMP-321; KRN-7000; antibodies, such as civacir, XTL-6865 and the like; and prophylactic and therapeutic vaccines such as InnoVac C, HCV E1E2/MF59 and the like.

Other antiviral agents include, but are not limited to, ribavirin, amantadine, viramidine, nitazoxanide; telbivudine; NOV-205; taribavirin; inhibitors of internal ribosome entry; broad-spectrum viral inhibitors, such as IMPDH inhibitors (e.g., compounds of U.S. Pat. No. 5,807,876, U.S. Pat. No. 6,498,178, U.S. Pat. No. 6,344,465, U.S. Pat. No. 6,054,472, WO97/40028, WO98/40381, WO00/56331, and mycophenolic acid and derivatives thereof, and including, but not limited to VX-950, merimepodib (VX-497), VX-148, and/or VX-944); or combinations of any of the above.

Thus, to combat or treat HCV infections, the compounds of formula (I) may be co-administered in combination with for instance, interferon-α (IFN-α), pegylated interferon-α and/or ribavirin, as well as therapeutics based on antibodies targeted against HCV epitopes, small interfering RNA (Si RNA), ribozymes, DNAzymes, antisense RNA, small molecule antagonists of for instance NS3 protease, NS3 helicase and NS5B polymerase.

Accordingly, the present invention relates to the use of a compound of formula (I) or any subgroup thereof as defined above for the manufacture of a medicament useful for inhibiting HCV activity in a mammal infected with HCV viruses, wherein said medicament is used in a combination therapy, said combination therapy preferably comprising a compound of formula (I) and another HCV inhibitory compound, e.g. (pegylated) IFN-α and/or ribavirin.

In still another aspect there are provided combinations of a compound of formula (I) as specified herein and an anti-HIV compound. The latter preferably are those HIV inhibitors that have a positive effect on drug metabolism and/or pharmacokinetics that improve bioavailabilty. An example of such an HIV inhibitor is ritonavir.

As such, the present invention further provides a combination comprising (a) an HCV NS3/4a protease inhibitor of formula (I) or a pharmaceutically acceptable salt thereof, and (b) ritonavir or a pharmaceutically acceptable salt thereof.

The compound ritonavir, and pharmaceutically acceptable salts thereof, and methods for its preparation are described in WO94/14436. For preferred dosage forms of ritonavir, see U.S. Pat. No. 6,037,157, and the documents cited therein: U.S. Pat. No. 5,484,801, U.S. Ser. No. 08/402,690, and WO95/07696 and WO95/09614. Ritonavir has the following formula:

In a further embodiment, the combination comprising (a) an HCV NS3/4a protease inhibitor of formula (I) or a pharmaceutically acceptable salt thereof; and (b) ritonavir or a pharmaceutically acceptable salt thereof, further comprises an additional anti-HCV compound selected from the compounds as described herein.

In one embodiment of the present invention there is provided a process for preparing a combination as described herein, comprising the step of combining an HCV NS3/4a protease inhibitor of formula (I) or a pharmaceutically acceptable salt thereof, and ritonavir or a pharmaceutically acceptable salt thereof. An alternative embodiment of this invention provides a process wherein the combination comprises one or more additional agent as described herein.

The combinations of the present invention may be used as medicaments. Said use as a medicine or method of treatment comprises the systemic administration to HCV-infected subjects of an amount effective to combat the conditions associated with HCV and other pathogenic flavi- and pestiviruses. Consequently, the combinations of the present invention can be used in the manufacture of a medicament useful for treating, preventing or combating infection or disease associated with HCV infection in a mammal, in particular for treating conditions associated with HCV and other pathogenic flavi- and pestiviruses.

In one embodiment of the present invention there is provided a pharmaceutical composition comprising a combination according to any one of the embodiments described herein and a pharmaceutically acceptable excipient. In particular, the present invention provides a pharmaceutical composition comprising (a) a therapeutically effective amount of an HCV NS3/4a protease inhibitor of the formula (I) or a pharmaceutically acceptable salt thereof, (b) a therapeutically effective amount of ritonavir or a pharmaceutically acceptable salt thereof, and (c) a pharmaceutically acceptable excipient. Optionally, the pharmaceutical composition further comprises an additional agent selected from an HCV polymerase inhibitor, an HCV protease inhibitor, an inhibitor of another target in the HCV life cycle, and immunomodulatory agent, an antiviral agent, and combinations thereof.

The compositions may be formulated into suitable pharmaceutical dosage forms such as the dosage forms described above. Each of the active ingredients may be formulated separately and the formulations may be co-administered or one formulation containing both and if desired further active ingredients may be provided.

As used herein, the term "composition" is intended to encompass a product comprising the specified ingredients, as well as any product which results, directly or indirectly, from the combination of the specified ingredients.

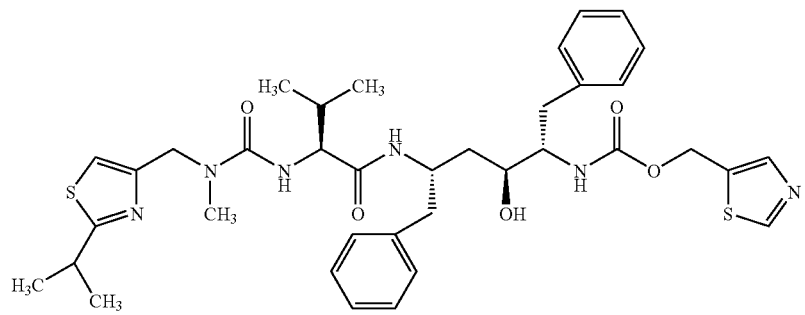

In one embodiment the combinations provided herein may also be formulated as a combined preparation for simultaneous, separate or sequential use in HIV therapy. In such a case, the compound of general formula (I) or any subgroup thereof, is formulated in a pharmaceutical composition containing other pharmaceutically acceptable excipients, and ritonavir is formulated separately in a pharmaceutical composition containing other pharmaceutically acceptable excipients. Conveniently, these two separate pharmaceutical compositions can be part of a kit for simultaneous, separate or sequential use.

Thus, the individual components of the combination of the present invention can be administered separately at different times during the course of therapy or concurrently in divided or single combination forms. The present invention is therefore to be understood as embracing all such regimes of simultaneous or alternating treatment and the term "administering" is to be interpreted accordingly. In a preferred embodiment, the separate dosage forms are administered about simultaneously.

In one embodiment, the combination of the present invention contains an amount of ritonavir, or a pharmaceutically acceptable salt thereof, which is sufficient to clinically improve the bioavailability of the HCV NS3/4a protease inhibitor of formula (I) relative to the bioavailability when said HCV NS3/4a protease inhibitor of formula (I) is administered alone.

In another embodiment, the combination of the present invention contains an amount of ritonavir, or a pharmaceutically acceptable salt thereof, which is sufficient to increase at least one of the pharmacokinetic variables of the HCV NS3/4a protease inhibitor of formula (I) selected from $t_{1/2}$, $C_{min}$, $C_{max}$, $C_{ss}$, AUC at 12 hours, or AUC at 24 hours, relative to said at least one pharmacokinetic variable when the HCV NS3/4a protease inhibitor of formula (I) is administered alone.

A further embodiment relates to a method for improving the bioavailability of a HCV NS3/4a protease inhibitor comprising administering to an individual in need of such improvement a combination as defined herein, comprising a therapeutically effective amount of each component of said combination.

In a further embodiment, the invention relates to the use of ritonavir or a pharmaceutically acceptable salt thereof, as an improver of at least one of the pharmacokinetic variables of a HCV NS3/4a protease inhibitor of formula (I) selected from $t_{1/2}$, $C_{min}$, $C_{max}$, $C_{ss}$, AUC at 12 hours, or AUC at 24 hours; with the proviso that said use is not practised in the human or animal body.

The term "individual" as used herein refers to an animal, preferably a mammal, most preferably a human, who has been the object of treatment, observation or experiment.

Bioavailability is defined as the fraction of administered dose reaching systemic circulation. $t_{1/2}$ represents the half life or time taken for the plasma concentration to fall to half its original value. $C_{ss}$ is the steady state concentration, i.e. the concentration at which the rate of input of drug equals the rate of elimination. $C_{min}$ is defined as the lowest (minimum) concentration measured during the dosing interval. $C_{max}$ represents the highest (maximum) concentration measured during the dosing interval. AUC is defined as the area under the plasma concentration-time curve for a defined period of time.

The combinations of this invention can be administered to humans in dosage ranges specific for each component comprised in said combinations. The components comprised in said combinations can be administered together or separately. The NS3/4a protease inhibitors of formula (I) or any subgroup thereof, and ritonavir or a pharmaceutically acceptable salt or ester thereof, may have dosage levels of the order of 0.02 to 5.0 grams-per-day.

When the HCV NS3/4a protease inhibitor of formula (I) and ritonavir are administered in combination, the weight ratio of the HCV NS3/4a protease inhibitor of formula (I) to ritonavir is suitably in the range of from about 40:1 to about 1:15, or from about 30:1 to about 1:15, or from about 15:1 to about 1:15, typically from about 10:1 to about 1:10, and more typically from about 8:1 to about 1:8. Also useful are weight ratios of the HCV NS3/4a protease inhibitors of formula (I) to ritonavir ranging from about 6:1 to about 1:6, or from about 4:1 to about 1:4, or from about 3:1 to about 1:3, or from about 2:1 to about 1:2, or from about 1.5:1 to about 1:1.5. In one aspect, the amount by weight of the HCV NS3/4a protease inhibitors of formula (I) is equal to or greater than that of ritonavir, wherein the weight ratio of the HCV NS3/4a protease inhibitor of formula (I) to ritonavir is suitably in the range of from about 1:1 to about 15:1, typically from about 1:1 to about 10:1, and more typically from about 1:1 to about 8:1. Also useful are weight ratios of the HCV NS3/4a protease inhibitor of formula (I) to ritonavir ranging from about 1:1 to about 6:1, or from about 1:1 to about 5:1, or from about 1:1 to about 4:1, or from about 3:2 to about 3:1, or from about 1:1 to about 2:1 or from about 1:1 to about 1.5:1.

The term "therapeutically effective amount" as used herein means that amount of active compound or component or pharmaceutical agent that elicits the biological or medicinal response in a tissue, system, animal or human that is being sought, in the light of the present invention, by a researcher, veterinarian, medical doctor or other clinician, which includes alleviation of the symptoms of the disease being treated. Since the instant invention refers to combinations comprising two or more agents, the "therapeutically effective amount" is that amount of the agents taken together so that the combined effect elicits the desired biological or medicinal response. For example, the therapeutically effective amount of a composition comprising (a) the compound of formula (I) and (b) ritonavir, would be the amount of the compound of formula (I) and the amount of ritonavir that when taken together have a combined effect that is therapeutically effective.

In general it is contemplated that an antiviral effective daily amount would be from 0.01 mg/kg to 500 mg/kg body weight, more preferably from 0.1 mg/kg to 50 mg/kg body weight. It may be appropriate to administer the required dose as two, three, four or more sub-doses at appropriate intervals throughout the day. Said sub-doses may be formulated as unit dosage forms, for example, containing 1 to 1000 mg, and in particular 5 to 200 mg of active ingredient per unit dosage form.

The exact dosage and frequency of administration depends on the particular compound of formula (I) used, the particular condition being treated, the severity of the condition being treated, the age, weight, sex, extent of disorder and general physical condition of the particular patient as well as other medication the individual may be taking, as is well known to those skilled in the art. Furthermore, it is evident that said effective daily amount may be lowered or increased depending on the response of the treated subject and/or depending on the evaluation of the physician prescribing the compounds of the instant invention. The effective daily amount ranges mentioned hereinabove are therefore only guidelines.

According to one embodiment, the HCV NS3/4a protease inhibitor of formula (I) and ritonavir may be co-administered once or twice a day, preferably orally, wherein the amount of the compounds of formula (I) per dose is from about 1 to about 2500 mg, and the amount of ritonavir per dose is from 1 to about 2500 mg. In another embodiment, the amounts per dose for once or twice daily co-administration are from about 50 to about 1500 mg of the compound of formula (I) and from about 50 to about 1500 mg of ritonavir. In still another embodiment, the amounts per dose for once or twice daily co-administration are from about 100 to about 1000 mg of the compound of formula (I) and from about 100 to about 800 mg of ritonavir. In yet another embodiment, the amounts per dose for once or twice daily co-administration are from about 150 to about 800 mg of the compound of formula (I) and from about 100 to about 600 mg of ritonavir. In yet another embodiment, the amounts per dose for once or twice daily co-administration are from about 200 to about 600 mg of the compound of formula (I) and from about 100 to about 400 mg of ritonavir. In yet another embodiment, the amounts per dose for once or twice daily co-administration are from about 200 to about 600 mg of the compound of formula (I) and from about 20 to about 300 mg of ritonavir. In yet another embodiment, the amounts per dose for once or twice daily co-administration are from about 100 to about 400 mg of the compound of formula (I) and from about 40 to about 100 mg of ritonavir.

Exemplary combinations of the compound of formula (I) (mg)/ritonavir (mg) for once or twice daily dosage include 50/100, 100/100, 150/100, 200/100, 250/100, 300/100, 350/100, 400/100, 450/100, 50/133, 100/133, 150/133, 200/133, 250/133, 300/133, 50/150, 100/150, 150/150, 200/150, 250/150, 50/200, 100/200, 150/200, 200/200, 250/200, 300/200, 50/300, 80/300, 150/300, 200/300, 250/300, 300/300, 200/600, 400/600, 600/600, 800/600, 1000/600, 200/666, 400/666, 600/666, 800/666, 1000/666, 1200/666, 200/800, 400/800, 600/800, 800/800, 1000/800, 1200/800, 200/1200, 400/1200, 600/1200, 800/1200, 1000/1200, and 1200/1200. Other exemplary combinations of the compound of formula (I) (mg)/ritonavir (mg) for once or twice daily dosage include 1200/400, 800/400, 600/400, 400/200, 600/200, 600/100, 500/100, 400/50, 300/50, and 200/50.

In one embodiment of the present invention there is provided an article of manufacture comprising a composition effective to treat an HCV infection or to inhibit the NS3 protease of HCV; and packaging material comprising a label which indicates that the composition can be used to treat infection by the hepatitis C virus; wherein the composition comprises a compound of the formula (I) or any subgroup thereof, or the combination as described herein.

Another embodiment of the present invention concerns a kit or container comprising a compound of the formula (I) or any subgroup thereof, or a combination according to the invention combining an HCV NS3/4a protease inhibitor of formula (I) or a pharmaceutically acceptable salt thereof, and ritonavir or a pharmaceutically acceptable salt thereof, in an amount effective for use as a standard or reagent in a test or assay for determining the ability of potential pharmaceuticals to inhibit HCV NS3/4a protease, HCV growth, or both. This aspect of the invention may find its use in pharmaceutical research programs.

The compounds and combinations of the present invention can be used in high-throughput target-analyte assays such as those for measuring the efficacy of said combination in HCV treatment.

EXAMPLES

The following examples are intended to illustrate the present invention and not to limit it thereto.

Example 1

Preparation of N-[18-[2-(4-isopropylthiazol-2-yl)-7-methoxyquinolin-4-yl]-2,15-dioxo-3,14,16-triazatricyclo[14.3.0.0$^{4,6}$]nonadec-7-ene-4-carbonyl](N',N'-di-methyl)sulfamide (9)

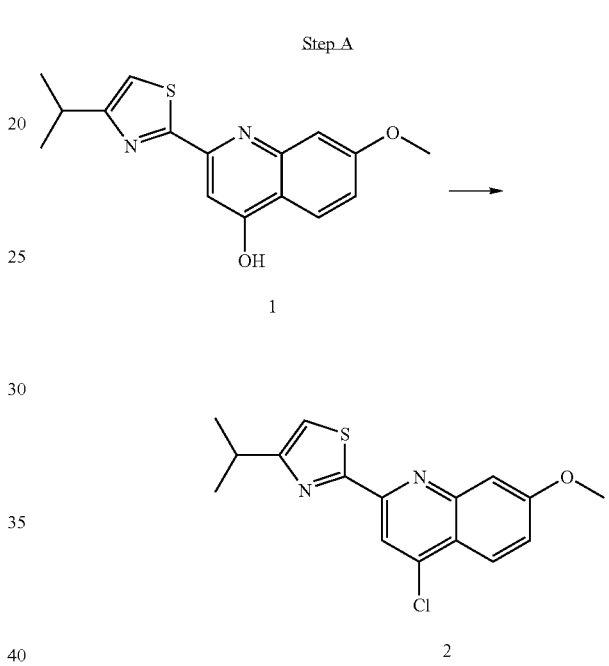

A solution of 2-(4-isopropylthiazol-2-yl)-7-methoxyquinolin-4-ol (1, 3.6 g) in phosphorus oxychloride (20 mL) was heated at 100° C. for 40 min (reaction was monitored by LC-MS). Then, the reaction was cooled down to room temperature and the excess of phosphorus oxychloride was evaporated. The residual oil was partitioned between a saturated solution of sodium bicarbonate and extracted with ether (3×70 mL). The combined organic extracts were washed with brine, dried over magnesium sulfate, concentrated by rotary evaporation and passed through short pad of silica (hexanes) to give 3.6 g (62%) of the desired product 2 as white powder.

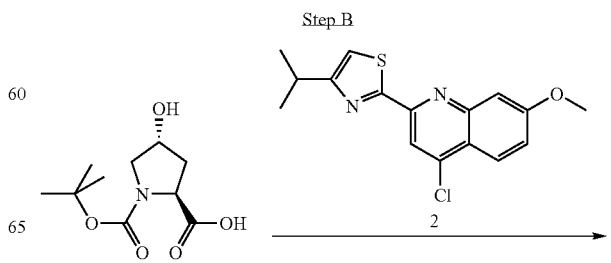

-continued

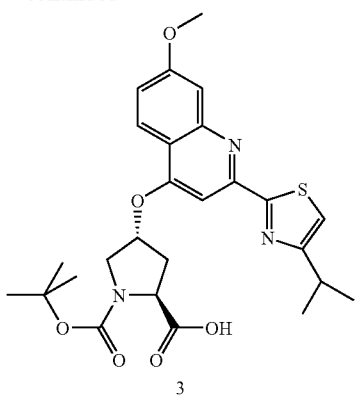

3

To a stirred solution of Boc-hydroxyproline (2.6 g, 11.2 mmol) in DMSO (80 mL) was added potassium tert-butoxide (3.8 g, 3 eq). After approximately 1 h of stirring 4-chloro-2-(4-isopropylthiazol-2-yl)-7-methoxyquinoline (2, 3.6 g, 11.2 mmol) was added and the reaction mixture was stirred at room temperature overnight. Then, the reaction mixture was diluted with water (350 mL) and neutralized with 1N HCl. The resulting suspension was extracted into ethylacetate (3×100 mL), washed with brine and dried over magnesium sulfate. Filtration and concentration by rotary evaporation gave after drying overnight on high vacuum 3.6 g (62%) of the desired product 3: Purity by HPLC >95%, m/z=514 (M+H)$^+$.

Step C

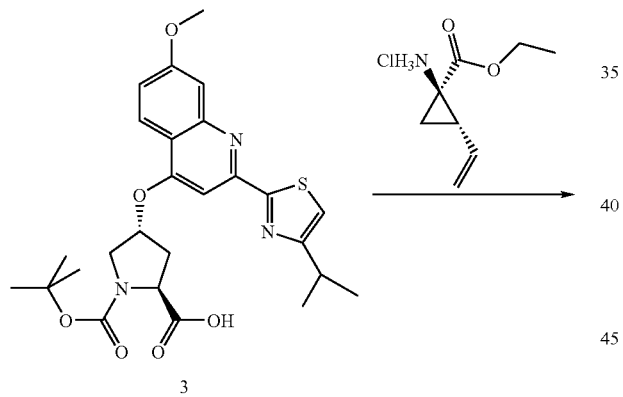

4

The acid 3 (3.6 g, 7 mmol) was mixed with the 1-amino-2-vinyl-cyclopropane-carboxylic acid methyl ester hydrochloride (1.47 g, 7.6 mmol), and then dissolved in DMF. The reaction mixture was flushed with argon and cooled down in an ice bath and DIPEA (1.5 mL) was added in one portion. Then, the reaction mixture was stirred for 10-15 min at 0° C., before HATU (2.93 g, 7.7 mmol) was added at 0° C. under argon, in one portion. After 40 min at 0° C. (reaction was monitored by LC-MS), the reaction mixture was concentrated by rotary evaporation (not to complete dryness), then mixed with a solution of saturated sodium bicarbonate and extracted into EtOAc (3×100 mL). The organic layer was washed with brine, dried over magnesium sulfate and concentrated by rotary evaporation. Purification by column chromatography on silica (DCM) and then on YMC silica (200 g, gradient hexanes/EA 3:2 to 2:3) afforded 3.81 g (84%) of the target product 4 as a white powder.

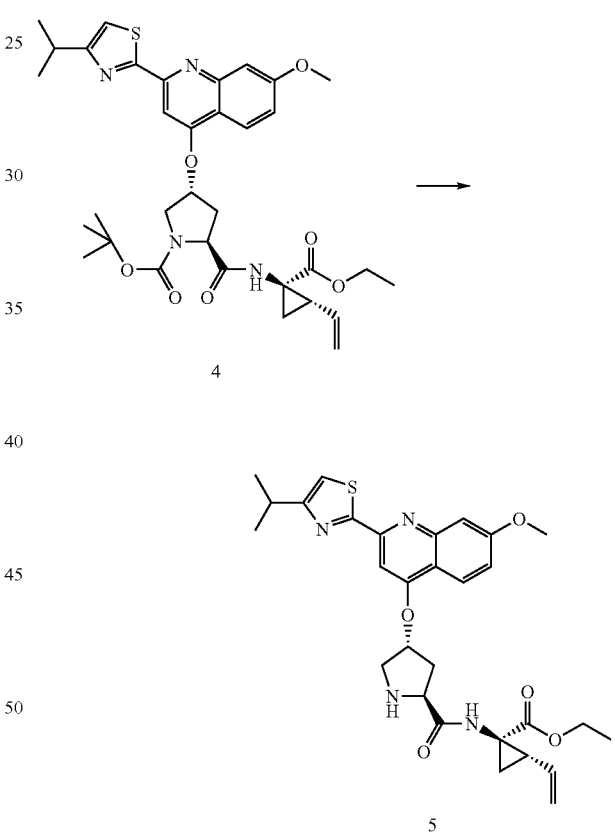

A solution of 4 (3.81 g, 5.8 mmol) in dichloromethane (30 mL) and trifluoroacetic acid (30 mL) was stirred at room temperature for about 1.5 h. Then, the solvent was evaporated and the residue partitioned between saturated sodium bicarbonate (100 mL) and ether (3×100 mL). The ether layers were combined, washed with brine, dried over magnesium sulfate and evaporated to give 3.13 g (98.3%) of the target product 5: m/z=551 (M+H)$^+$.

Step E

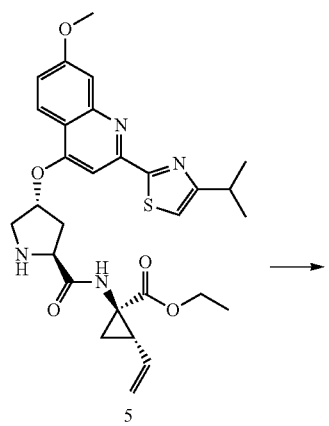

5

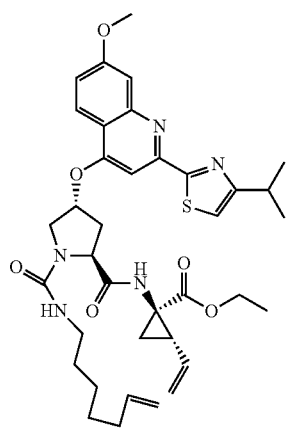

6

Sodium hydrogencarbonate (1.0 g) was added to a solution of 5 (1.4 g, 2.5 mmol) in tetrahydrofuran (50 mL). Then, phosgene (5 mL, 1.9 M in toluene) was added at 0° C. under argon. The resulting suspension was stirred for 40 min at room temperature (monitoring with LS-MS). Then, the reaction mixture was filtered and washed with THF (2×30 mL). The filtrate was concentrated by rotary evaporation and re-dissolved in dichloromethane (50 mL). Sodium hydrogencarbonate (1.0 g) and N-methylhept-6-enylamine (1.5 g, 13 mmol) was added. The reaction mixture was stirred at room temperature overnight, and then filtered. Purification by chromatography on silica gel (ether) provided 1.42 g (84%) the target product 6: m/z=690 (M+H)$^+$.

Step F

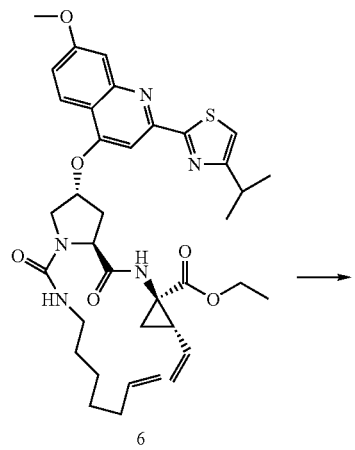

6

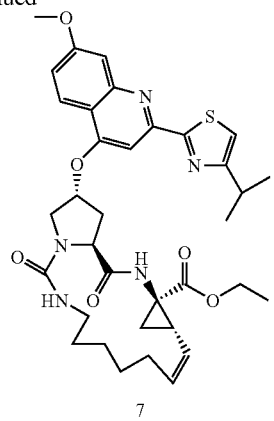

7

A solution of 6 (1.42 g, 2 mmol) in dry dichloroethane (900 mL, 0.0023M solution) was bubbled with argon for approximately 15 min. Then, Hoveyda-Grubbs 1$^{st}$ generation catalyst (120 mg, 12 mol %) was added and the reaction mixture was heated at reflux under stirring with a slow flow of argon for 16 h. The reaction mixture was then cooled to room temperature and MP-TMT palladium scavenger (approximately 200 mg) was added and the mixture. After 2.5 h, the scavenger was removed by filtration and washed with 50 mL dichloromethane. The solution obtained was concentrated by rotary evaporation. The residue was purified by column chromatography on YMC silica (100 g, EtOAc/hexanes 1:1) to give 806 mg (57%) of the target product 7: m/z=662 (M+H)$^+$.

Step G

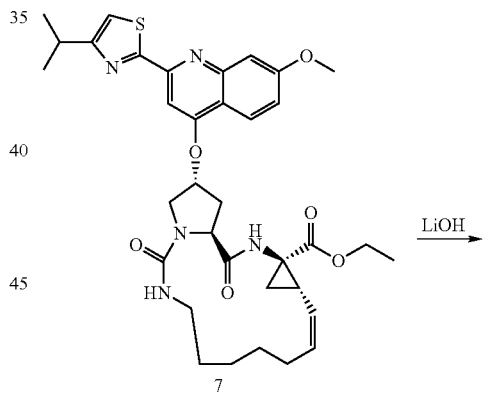

7

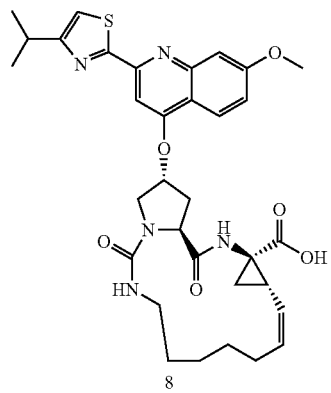

8

Lithium hydroxide (300 mg) in water (6 mL) was added to a solution of the macro-cyclic ester 7 (806 mg, 2.1 mmol) in tetrahydrofuran (12 mL) and methanol (6 mL). After 1 h at 50° C., the volume was reduced to half by evaporation and water (30 mL) was added. Acidification (pH=2) followed by extraction with chloroform gave 760 mg of the target product 8 as a white powder: m/z=662 (M+H)$^+$.

Step H

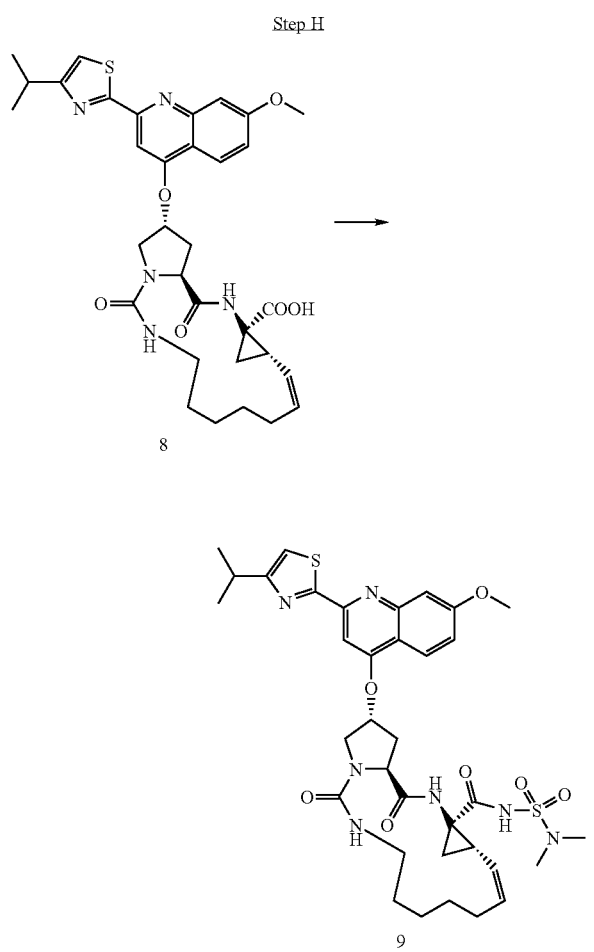

A solution of acid 8 (760 mg, 1.2 mmol) and CDI (389 mg, 2.4 mmol, 2 eq) in dry THF (10 mL) is heated at reflux for 2 h under N$_2$. The reaction mixture is allowed to cool down at room temperature: this solution is called solution A. Optionally, the azalactone derivative present in solution A, if desired, can be isolated. In another flask, LiHMDS (1.0 M solution in hexanes, 4.8 mmol) is added under nitrogen at 0° C. to a solution of N,N-dimethylsulfamide (4.8 mmol) in dry THF (10 mL). The resulting mixture is allowed to warm up to room temperature for 1 h: this solution is called solution B. Then, solution B is added under nitrogen to solution A. The resulting mixture is stirred at room temperature for 2 h. Then, the solvent is evaporated and the residue partitioned between EtOAc and water (pH adjusted to 3.0 with HCl). The crude material is purified by column chromatography EtOAc/Petroleum ether 1:1), then triturated in water, filtered and washed with water to give the title product 9 as a white powder. m/z=740 (M+H)$^+$.

Example 2

Preparation of N-[17-[2-(3-isopropylpyrazol-1-yl)-7-methoxy-8-methylquinolin-4-yloxy]-13-methyl-2,14-dioxo-3,13-diazatricyclo[13.3.0.0$^{4,6}$]octadec-7-ene-4-carbonyl](dimethylamino)sulfonamide (29)

Step 1: Synthesis of ethyl 4-hydroxy-7-methoxy-8-methylquinoline-3-carboxylate (11)

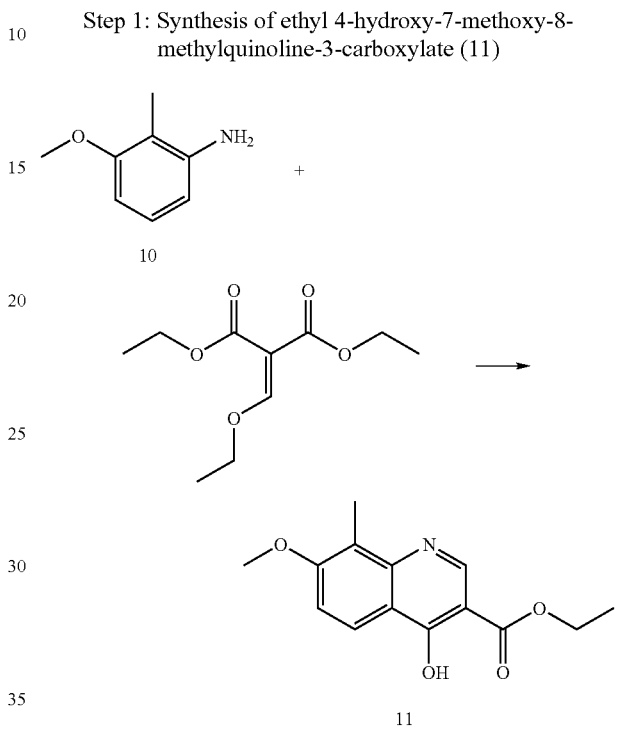

Diethyl ethoxymethylenemalonate (17.2 g, 79.6 mmol) was added to 2-methyl-m-anisidine (8.4 g, 61.2 mmol) (exothermic reaction). Then, diethylether (100 mL) was added and the mixture was stirred overnight at room temperature. The solvent was evaporated and the residue re-dissolved in ether (50 mL), filtered, washed with heptane and dried to give 12 g of an intermediate. This intermediate was added portion wise to diphenyl ether (50 mL) pre-heated at 230° C. The reaction mixture was successively heated to 250° C. for 1.5 h, cooled at room temperature, and diluted with heptane (200 mL). The precipitate was filtered off, and successively washed with heptane and ether to give 9.2 g (57.5%) of the target product 11 as a yellow powder: m/z=262 (M+H)$^+$.

Step 2: Synthesis of 4-Hydroxy-7-methoxy-8-methylquinoline (12)

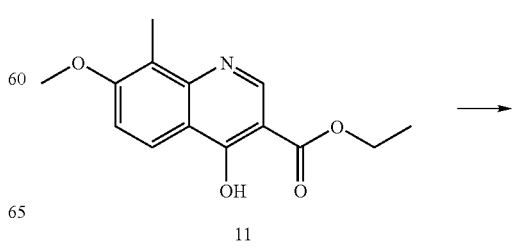

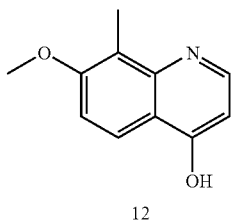

12

A suspension of ethyl 4-hydroxy-7-methoxy-8-methylquinoline-3-carboxylate (11, 9.2 g, 35.2 mmol) in 5N NaOH (150 mL) was refluxed for 1.5 h (until a clear solution was obtained). Then, the solution was cooled to 0° C. and the pH adjusted to 2-3 with concentrated HCl. The solid was filtered off and successively washed with water, acetone and ether. This powder was added in small portions to diphenylether (40 mL), pre-heated at 250° C. The resulting suspension became a solution after 20 min ($CO_2$ formation was observed). After 1 h at 250° C., the brown solution was cooled to room temperature and diluted with heptanes (200 mL). The precipitate was filtered off and washed with heptanes and ether to give 6.4 g (96%) of the target product 12 as a yellow powder: m/z=190 $(M+H)^+$.

Step 3: Synthesis of
4-Chloro-7-methoxy-8-methylquinoline (13)

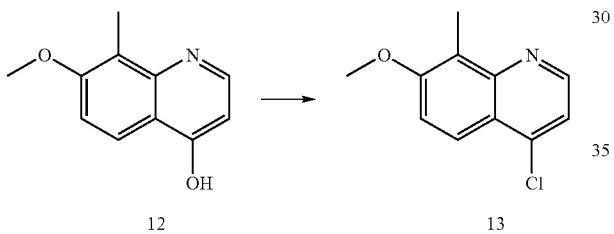

12 → 13

A solution of 4-hydroxy-7-methoxy-8-methylquinoline (12, 6.4 g, 33.8 mmol) in $POCl_3$ (17.2 g, 111.6 mmol) was heated at reflux for 1 h under nitrogen. Then, the resulting solution was cooled down to room temperature and the excess of $POCl_3$ was evaporated under reduced pressure. The residue was partitioned between ice-cold 1N NaOH and AcOEt. The organic layer was dried ($Na_2SO_4$), and evaporated. The residue was purified by silica-gel filtration (AcOEt/$CH_2Cl_2$/Heptane, 4:4:2) to give 6.5 g (92.5%) of the target product 13 as yellow needles: m/z=208 $(M+H)^+$.

Step 4: Synthesis of
4-Chloro-7-methoxy-8-methylquinoline N-oxide
(14)

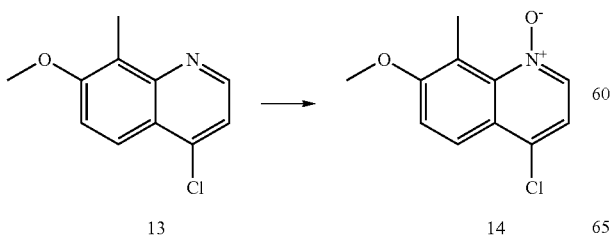

13 → 14

Metachloroperbenzoic acid (90.2 g, 366.0 mmol) was added portion wise over 3 h to a solution of 4-chloro-7-methoxy-8-methylquinoline (13, 15.2 g, 73.2 mmol) in $CHCl_3$ (1 L). Then, the solution was partitioned between ice-cooled NaOH 1N and $CH_2Cl_2$ (8 successive extractions). The organic layers were combined, dried ($Na_2SO_4$) and evaporated. The residue was purified by column chromatography (gradient of AcOEt/$CH_2Cl_2$, 1:2 to 1:0) to give 3.0 g (18.3%) of the title product 14 as a pale yellow powder: m/z=224 $(M+H)^+$.

Step 5: Synthesis of
4-benzyloxy-7-methoxy-8-methylquinoline N-oxide
(62)

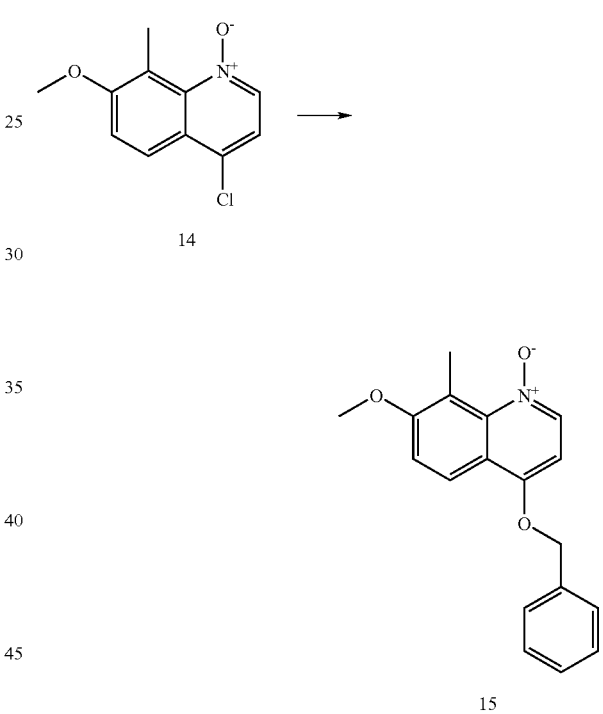

14 → 15

NaH (973 mg, 60% in mineral oil, 24.3 mmol) was added at 0° C., under inert atmosphere, to benzylalcohol (2.96 mL, 28.6 mmol) in DMF (10 mL). After 5 min at 0° C., the solution was warmed up to room temperature. After 10 min at room temperature, 4-chloro-7-methoxy-8-methylquinoline N-oxide (14, 3.2 g, 14.3 mmol) was added in one portion. The resulting black solution was stirred at room temperature under inert atmosphere for another 30 min, then poured into ice-cooled water, and extracted 4 times with AcOEt. Combined organic layers were dried ($Na_2SO_4$) and evaporated. The residue was purified by column chromatography (gradient AcOEt/$CH_2Cl_2$, 1:1 to 1:0, then AcOEt/MeOH 9:1) to give 2.5 g (59%) of the target product 15 as a yellow powder: m/z=296 $(M+H)^+$.

Step 6: Synthesis of 4-benzyloxy-2-chloro-7-methoxy-8-methylquinoline (16)

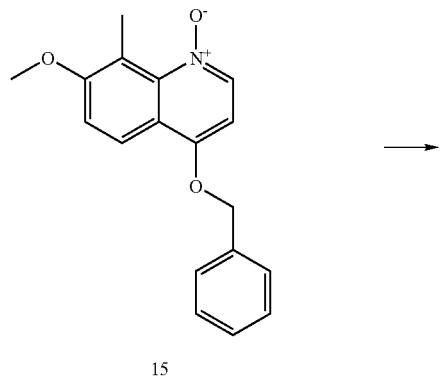

15

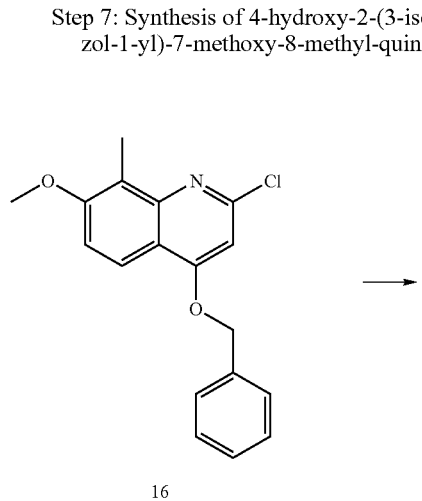

16

POCl$_3$ was added under inert atmosphere at −78° C. to 4-benzyloxy-7-methoxy-8-methylquinoline N-oxide (15, 2.5 g, 8.47 mmol). Then the reaction mixture was allowed to warm up to room temperature, then heated to reflux. After 35 min, the solution was cooled to room temperature and the excess of POCl$_3$ was evaporated under reduced pressure. The residue was partitioned between ice-cooled water and AcOEt, dried (Na$_2$SO$_4$) and evaporated. The residue was triturated in ether, then filtered and successively washed with small portions of methanol and ether to give 2.4 g (90.4%) of the target product 16 as a white powder: m/z=314 (M+H)$^+$.

Step 7: Synthesis of 4-hydroxy-2-(3-isopropylpyrazol-1-yl)-7-methoxy-8-methyl-quinoline (17)

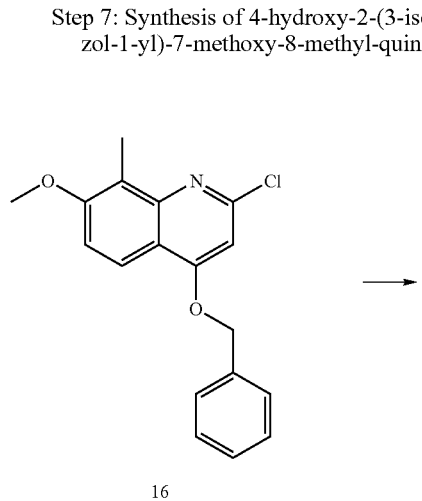

16

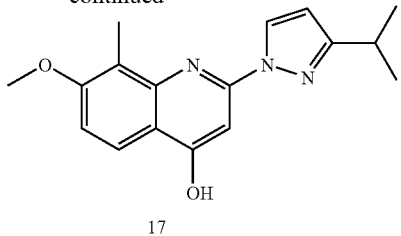

17

A mixture of 4-benzyloxy-2-chloro-7-methoxy-8-methylquinoline (16, 1.00 g, 3.19 mmol) and 3-isopropylpyrazole was heated at 155° C. for 12 h. Then, the reaction mixture was partitioned between AcOEt and water, dried (Na$_2$SO$_4$) and evaporated. The residue was purified by column chromatography (AcOEt/CH$_2$Cl$_2$, 1:1) to give 900 mg (95%) of the target product 17 as a yellowish powder: m/z=298 (M+H)$^+$.

Step 8: Synthesis of N-(hex-5-enyl)-N-methyltrifluoroacetamide (18)

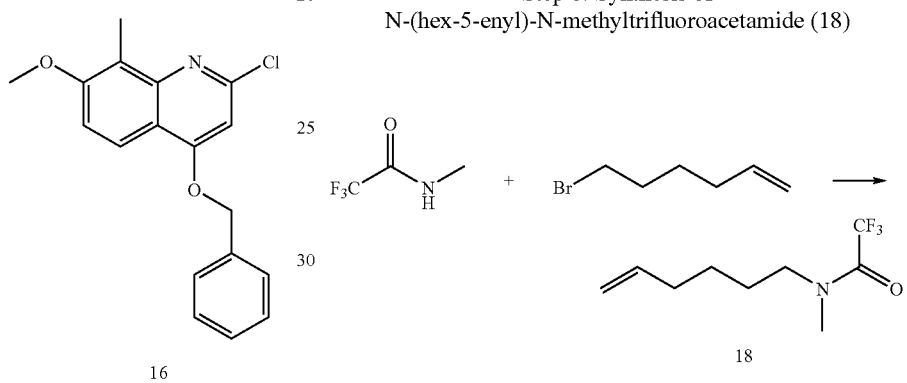

18

Sodium hydride (1.05 eq) was slowly added at 0° C. to a solution of N-methyltrifluoro-acetamide (25 g) in DMF (140 mL). The mixture was stirred for 1 h at room temperature under nitrogen. Then, a solution of bromohexene (32.1 g) in DMF (25 mL) was added dropwise and the mixture was heated to 70° C. for 12 hours. The reaction mixture was poured on water (200 mL) and extracted with ether (4×50 mL), dried (MgSO$_4$), filtered and evaporated to give 35 g of the target product 18 as a yellowish oil which was used without further purification in the next step.

Step 9: Synthesis of (hex-5-enyl)(methyl)amine (19)

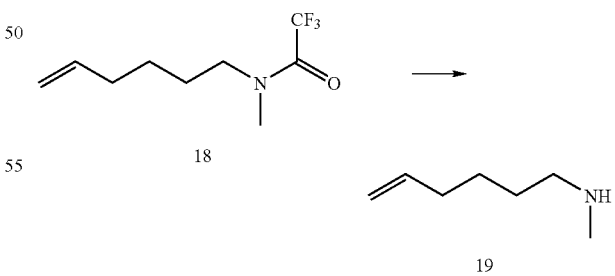

A solution of potassium hydroxide (187.7 g) in water (130 mL) was added dropwise to a solution of 18 (35 g) in methanol (200 mL). The mixture was stirred at room temperature for 12 hours. Then, the reaction mixture was poured on water (100 mL) and extracted with ether (4×50 mL), dried (MgSO$_4$), filtered and the ether was distilled under atmospheric pressure. The resulting oil was purified by distillation under vacuum (13 mm Hg pressure, 50° C.) to give 7.4 g (34%) of the title product 19 as a colourless oil: ¹H-NMR (CDCl₃): δ 5.8 (m, 1H), 5 (ddd, J=17.2 Hz, 3.5 Hz, 1.8 Hz, 1H), 4.95 (m, 1H), 2.5 (t, J=7.0 Hz, 2H), 2.43 (s, 3H), 2.08 (q, J=7.0 Hz, 2H), 1.4 (m, 4H), 1.3 (br s, 1H).

Step 10: Synthesis of intermediate 21

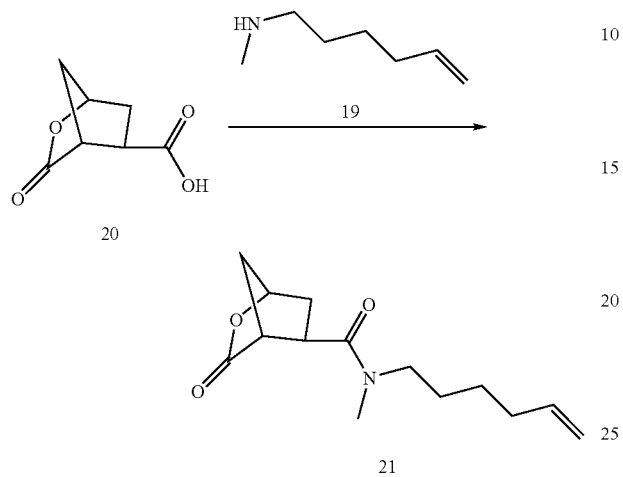

3-Oxo-2-oxa-bicyclo[2.2.1]heptane-5-carboxylic acid 20 (500 mg, 3.2 mmol) in 4 mL of DMF was added at 0° C. to HATU (1.34 g, 3.52 mmol) and N-methylhex-5-enylamine (435 mg, 3.84 mmol) in DMF (3 mL), followed by DIPEA. After stirring for 40 min at 0° C., the mixture was stirred at room temperature for 5 h. Then, the solvent was evaporated, the residue dissolved in EtOAc (70 mL) and washed with saturated NaHCO₃ (10 mL). The aqueous layer was extracted with EtOAc (2×25 mL). The organic layers were combined, washed with saturated NaCl (20 mL), dried (Na₂SO₄), and evaporated. Purification by flash chromatography (EtOAc/ petroleum ether, 2:1) afforded 550 mg (68%) of the target product 21 as a colorless oil: m/z=252 (M+H)⁺.

Step 11: Synthesis of intermediate 22

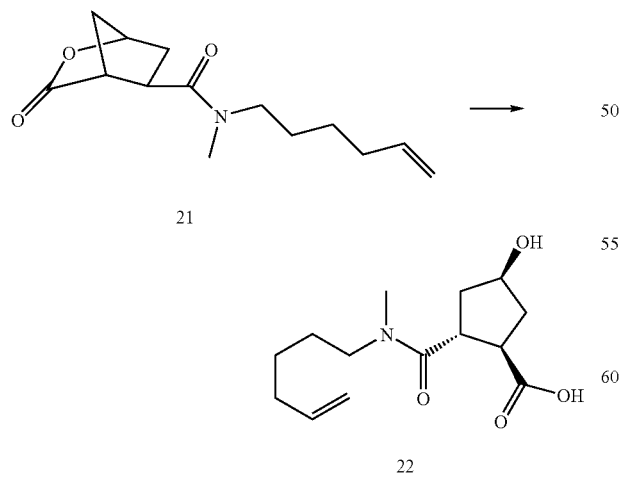

A solution of LiOH (105 mg in 4 mL of water) was added at 0° C. to the lactone amide 21. After 1 h, the conversion was completed (HPLC). The mixture was acidified to pH 2-3 with 1N HCl, extracted with AcOEt, dried (MgSO₄), evaporated, co-evaporated with toluene several times, and dried under high vacuum overnight to give 520 mg (88%) of the target product 22: m/z=270 (M+H)⁺.

Step 12: Synthesis of intermediate 24

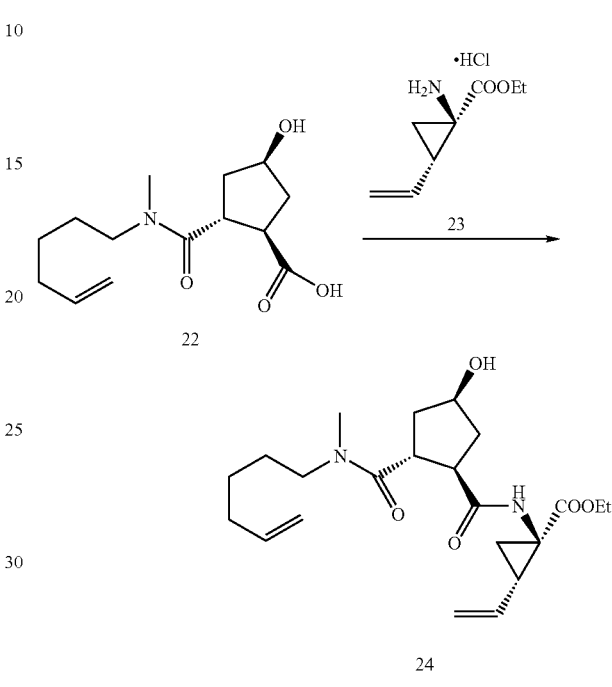

The 1-(amino)-2-(vinyl)cyclopropanecarboxylic acid ethyl ester hydrochloride 23 (4.92 g, 31.7 mmol) and HATU (12.6 g, 33.2 mmol) were added to 22 (8.14 g, 30.2 mmol). The mixture was cooled in an ice bath under argon, and then DMF (100 mL) and DIPEA (12.5 mL, 11.5 mmol) were successively added. After 30 min at 0° C., the solution was stirred at room temperature for 3 h. Then, the reaction mixture was partitioned between EtOAc and water, washed successively with 0.5 N HCl (20 mL) and saturated NaCl (2×20 mL), and dried (Na₂SO₄). Purification by flash chromatography (AcOEt/CH₂Cl₂/Petroleum ether, 1:1:1) afforded 7.41 g (60%) of the target product 24 as a colorless oil: m/z=407 (M+H)⁺.

Step 13: Synthesis of intermediate 25

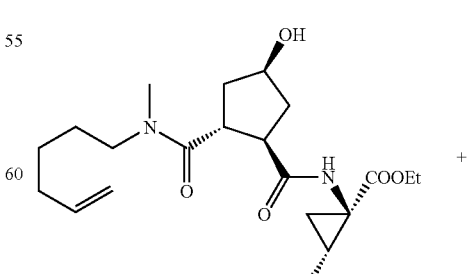

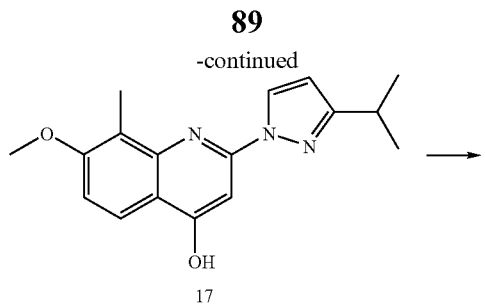

17

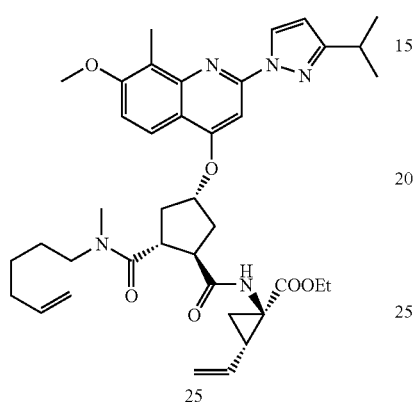

25

DIAD (429 mg, 2.1 mmol) was added at −20° C. under nitrogen atmosphere to a solution of 24 (552 mg, 1.4 mmol), quinoline 17 (390 mg, 1.3 mmol) and triphenylphosphine (583 mg, 2.2 mmol) in dry THF (15 mL). After 2 h at −20° C., the reaction was quenched with ice-cooled water and extracted with ether. The organic layer was successively washed with brine, dried (Na$_2$SO$_4$) and evaporated. The crude material was purified by flash column chromatography (AcOEt/CH$_2$Cl$_2$, 1:9) to give 670 mg (74%) of the target product 25: m/z=686 (M+H)$^+$.

Step 14: Synthesis of intermediate 26

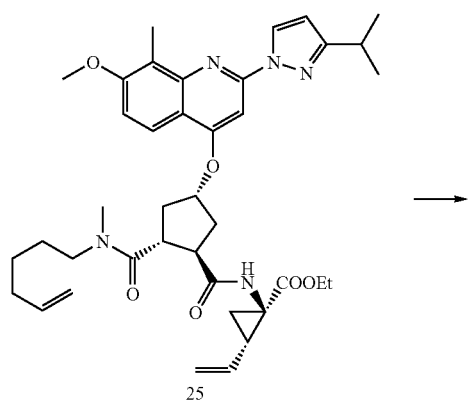

25

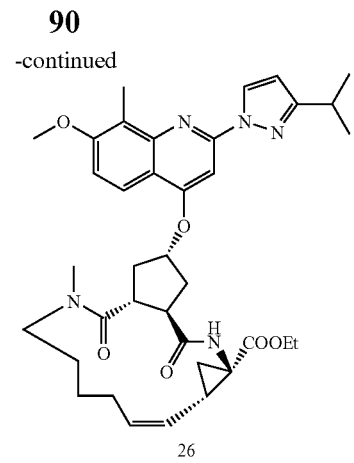

26

A solution of 25 (670 mg, 0.98 mmol) and Hoveyda-Grubbs 1$^{st}$ generation catalyst (130 mg, 0.22 mmol) in dried and degassed 1,2-dichloroethane (300 mL) is heated at 80° C. under nitrogen for 36 h. Then, the solvent is evaporated and the residue purified by silica gel chromatography (ether) to give the target product 26: m/z=658 (M+H)$^+$.

Step 15: Synthesis of intermediate 27

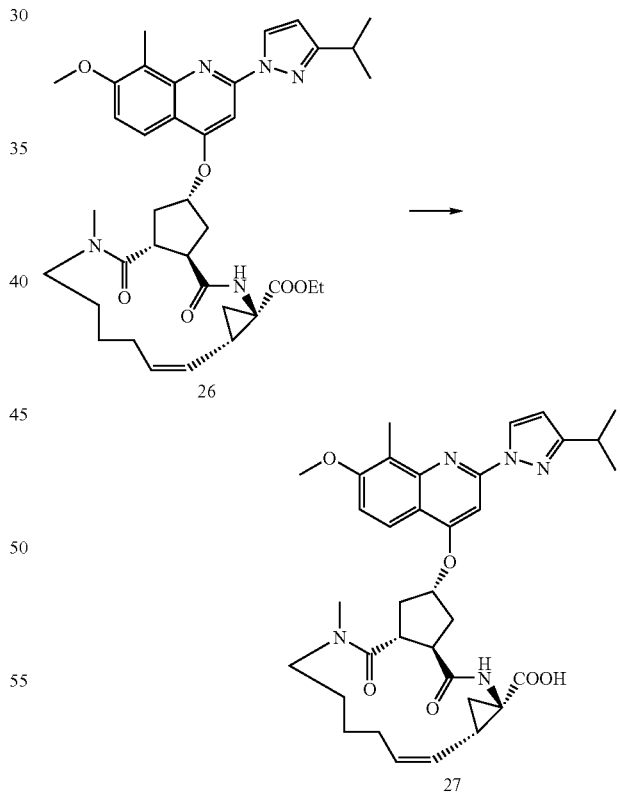

A solution of LiOH (1.14 g, 26.6 mmol) in water (10 mL) was added to a stirred solution of 26 (350 mg, 0.532 mmol) in THF (15 mL) and MeOH (15 mL). After 72 h, the pH of the reaction mixture was adjusted to 4 with diluted HCl. The resulting solution was partitioned between water and AcOEt. The organic layer was successively washed with brine, dried ($Na_2SO_4$) and evaporated to give 335 mg (100%) of the target compound 27: m/z=630 $(M+H)^+$.

Step 16: Synthesis of N-[17-[2-(3-isopropylpyrazol-1-yl)-7-methoxy-8-methylquinolin-4-yloxy]-13-methyl-2,14-dioxo-3,13-diazatricyclo[13.3.0.0$^{4,6}$]octadec-7-ene-4-carbonyl](dimethylamino)sulfonamide (29)

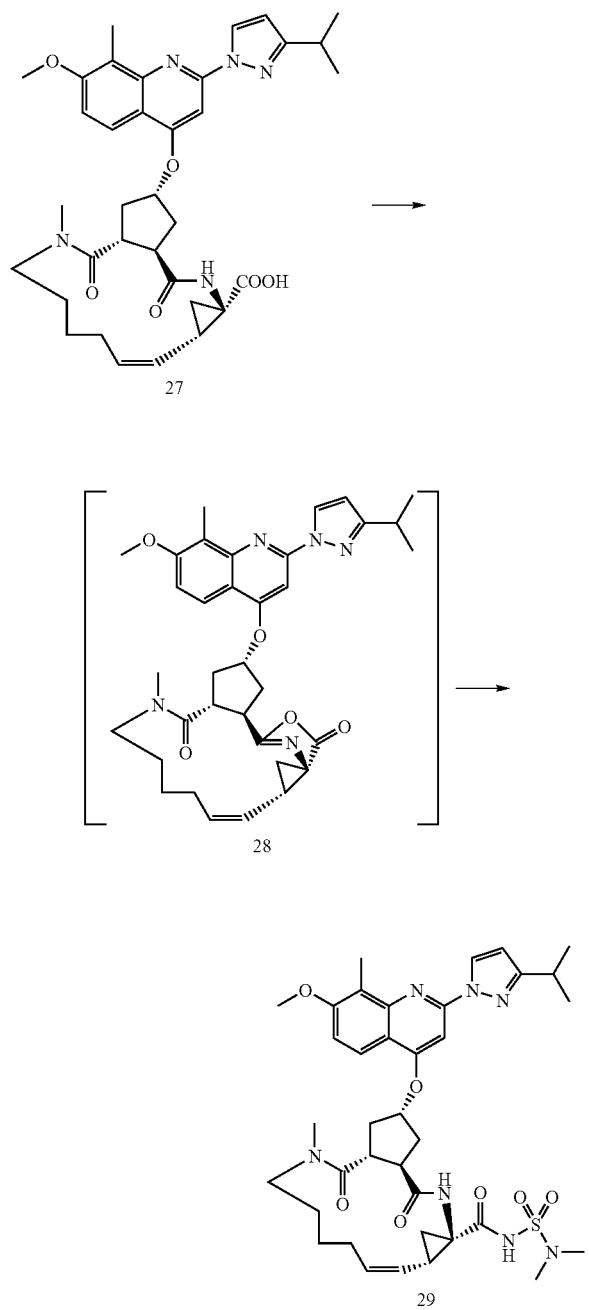

A mixture of 27 (181 mg, 0.29 mmol) and CDI (117 mg, 0.72 mmol) in dry THF (15 mL) was heated at reflux under nitrogen for 50 min. LCMS analysis showed one peak of the intermediate 28, which if needed, can be isolated by column chromato-graphy or can be reacted with the appropriate sulfonamide in a one-pot reaction. The reaction mixture was cooled down to room temperature and dimethylaminosulfonamide (98 mg, 0.79 mmol) was added. Then, DBU (141 mg, 0.92 mmol) was added and the reaction mixture was heated to 55° C. After 12 h, the solvent was evaporated, and the residue partitioned between AcOEt and acidic water (pH=4). The organic layer was dried ($Na_2SO_4$) and evaporated under reduced pressure to give a crude material, which was purified by column chromatography ($AcOEt/CH_2Cl_2$, 25:75) to give 70 mg (33%) of the target compound 29 as a white powder: m/z=736 $(M+H)^+$. $^1$H NMR ($CDCl_3$): 1.20-1.50 (m, 10H), 1.60-1.75 (m, 1H), 1.79-1.91 (m, 2H), 1.92-2.03 (m, 1H), 2.19-2.48 (m, 3H), 2.52-2.63 (m, 5H), 2.89-2.96 (m, 7H), 3.03 (s, 3H), 3.04-3.14 (m, 1H), 3.35-3.42 (m, 2H), 3.97 (s, 3H), 4.60 (dt, J=13.2 Hz, J=2.2 Hz, 1H), 5.05 (t, J=10.4 Hz, 1H), 5.26-3.35 (m, 1H), 5.64-5.70 (m, 1H), 6.26 (s, 1H), 6.32 (d, J=2.5 Hz, 1H), 7.11-7.15 (m, 1H), 7.30 (s, 1H), 7.95 (d, J=9.1 Hz, 1H), 8.69 (d, J=2.5 Hz, 1H), 10.6 (br s, 1H).

Example 3

Preparation of N-[17-[2-(5-bromo-2-fluorophenyl)-6,7-dihydro-5H-cyclo-pentapyrimidin-4-yloxy]-13-methyl-2,14-dioxo-3,13-diazatricyclo[13.3.0.0$^{4,6}$] octadec-7-ene-4-carbonyl](dimethylamino)sulfonamide (30)

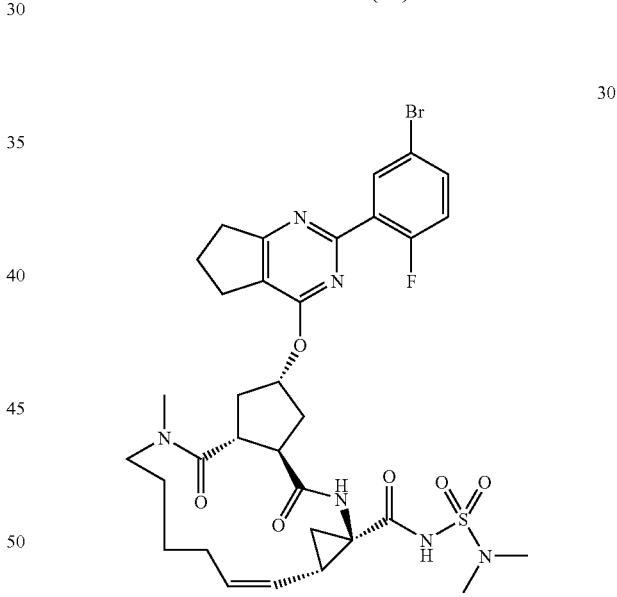

The title compound was prepared from 2-(5-bromo-2-fluorophenyl)-4-hydroxy-6,7-dihydro-5H-cyclopentapyrimidine and intermediate 24 following the procedure (Steps 13-16) reported for the preparation of N-[17-[2-(3-isopropylpyrazol-1-yl)-7-methoxy-8-methylquinolin-4-yloxy]-13-methyl-2,14-dioxo-3,13-diazatricyclo-[13.3.0.0$^{4,6}$]octadec-7-ene-4-carbonyl](dimethylamino)sulfonamide (29): m/z=748 $(M+H)^+$. $^1$H NMR ($CDCl_3$): 1.13-1.51 (m, 4H), 1.54-1.95 (m, 4H), 2.08-2.45 (m, 5H), 2.50-2.65 (m, 2H), 2.80-3.15 (m, 14H), 3.22-3.40 (m, 2H), 4.60 (t, J=12.4 Hz, 1H), 5.05 (t, J=9.9 Hz, 1H), 5.60-5.75 (m, 2H), 6.24 (s, 1H), 7.05 (t, J=9.5 Hz, 1H), 7.48-7.55 (m, 1H), 8.10-8.18 (m, 1H), 10.6 (br s, 1H).

Example 4

Preparation of N-[17-[2-(4-isopropylthiazol-2-yl)-7-methoxyquinolin-4-yloxy]-13-methyl-2,14-dioxo-3,13-diazatricyclo[13.3.0.0^{4,6}]octadec-7-ene-4-carbonyl](dimethylamino)sulfonamide (37)

Step 1: Synthesis of 2-(1-ethoxycarbonyl-2-vinyl-cyclopropylcarbamoyl)-4-[2-(4-iso-propyl-thiazol-2-yl)-7-methoxy-quinolin-4-yloxy]-cyclopentanecarboxylic acid (32)

perature. The resulting mixture was stirred for 2 h at room temperature, evaporated under reduced pressure, and co-evaporated twice with toluene. Purification by flash column chromatography (CH$_2$Cl$_2$/MeOH, 94:6) gave 290 mg (100%) of the title product 32 as a white solid.

Step 2: Synthesis of 1-({2-(hex-5-enyl-methyl-carbamoyl)-4-[2-(4-isopropyl-thiazol-2-yl)-7-methoxy-quinolin-4-yloxy]-cyclopentanecarbonyl}-amino)-2-vinyl-cyclopropanecarboxylic acid ethyl ester (33)

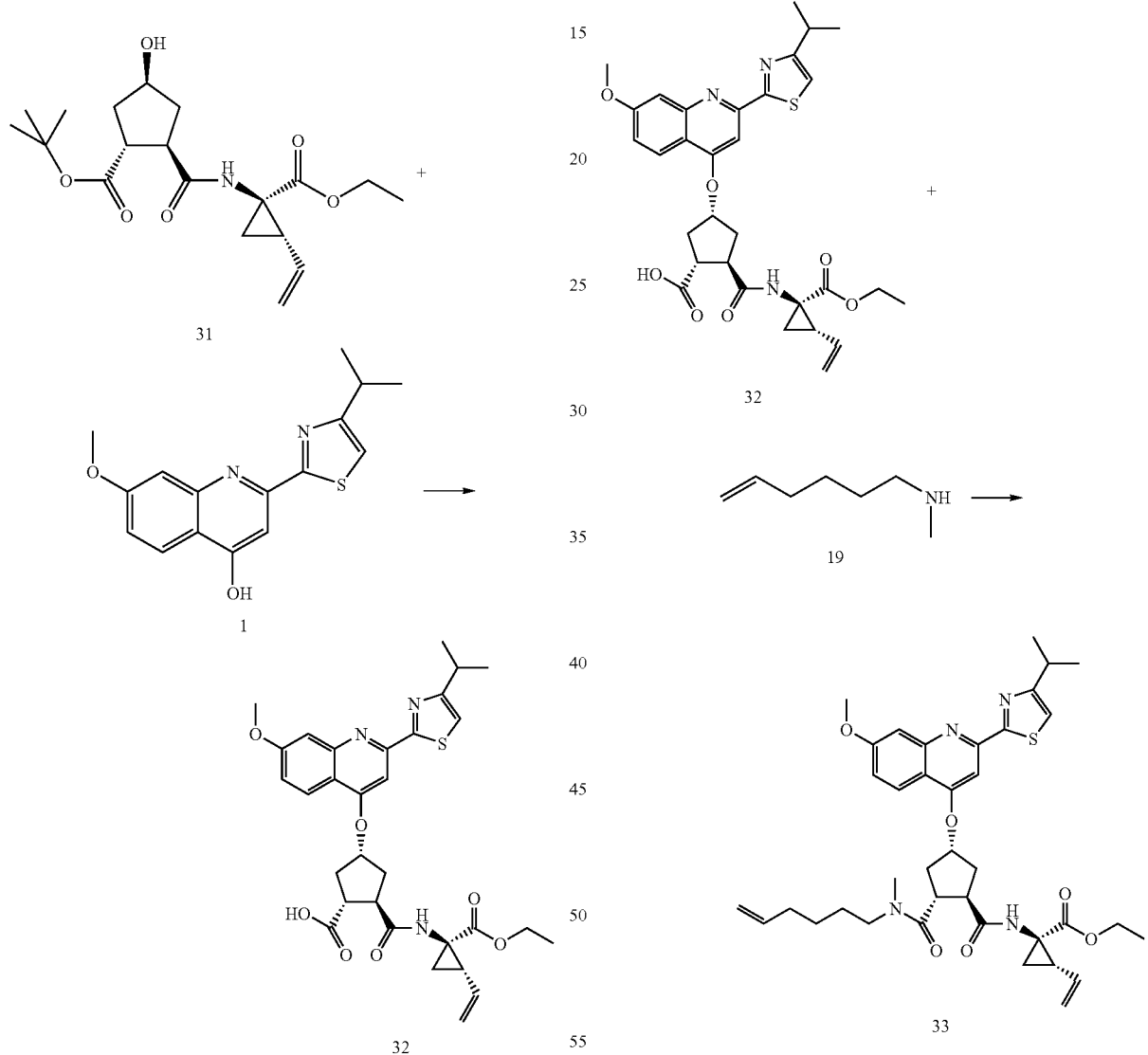

The alcohol 31 (249.3 mg, 0.678 mmol), PPh$_3$ (464 mg, 1.77 mmol), and the thiazole quinoline 1 (310 mg, 1.0 mmol) were dissolved in THF (13 mL), while cooling on an ice bath. Then, DIAD (350 µL, 1.77 mmol) was added dropwise. After 30 min at 0° C., the mixture was stirred at room temperature for 2 days, then concentrated under vacuum. Purification by flash column chromatography (silica, EtOAc/hexane) gave 320 mg of the Mitsunobu product. To this intermediate, a solution triethylsilane (142 mg, 1.22 mmol) in CH$_2$Cl$_2$ (25 mL) and TFA (25 mL) were added dropwise at room tem- To a solution of 2-(1-ethoxycarbonyl-2-vinyl-cyclopropylcarbamoyl)-4-[2-(4-iso-propyl-thiazol-2-yl)-7-methoxy-quinolin-4-yloxy]-cyclopentanecarboxylic acid (32, 0.49 mmol), N-methyl-5-hexenylamine HCl salt (19, 112.8 mg, 0.75 mmol), and HATU (277 mg, 0.73 mmol) in DMF (3 mL), was added at 0° C. DIEA (0.40 mL, 2.3 mmol). After 35 min at 0° C., the reaction mixture was stirred at room temperature for 3 h, then concentrated under vacuum. The residue was re-dissolved in AcOEt (20 mL) and then washed with saturated NaHCO$_3$ (5 mL). The aqueous layer was extracted with AcOEt (5 mL). Combined organic layers were washed with saturated NaCl (5 mL), dried (Na$_2$SO$_4$), and evaporated to give 660 mg of crude material. Purification by flash column chromatography (50 g silica; gradient AcOEt/petroleum ether, 3:2 to 3:1) gave 287 mg (85%) of the title product 33 as white solid: m/z=689 (M+H)$^+$.

Step 3: Synthesis of 17-[2-(4-isopropyl-thiazol-2-yl)-7-methoxy-quinolin-4-yloxy]-13-methyl-2,14-dioxo-3,13-diaza-tricyclo[13.3.0.0$^{4,6}$]octadec-7-ene-4-carboxylic acid ethyl ester (34)

Step 4: Synthesis of 17-[2-(4-isopropyl-thiazol-2-yl)-7-methoxy-quinolin-4-yloxy]-13-methyl-2,14-dioxo-3,13-diaza-tricyclo[13.3.0.0$^{4,6}$]octadec-7-ene-4-carboxylic acid (35)

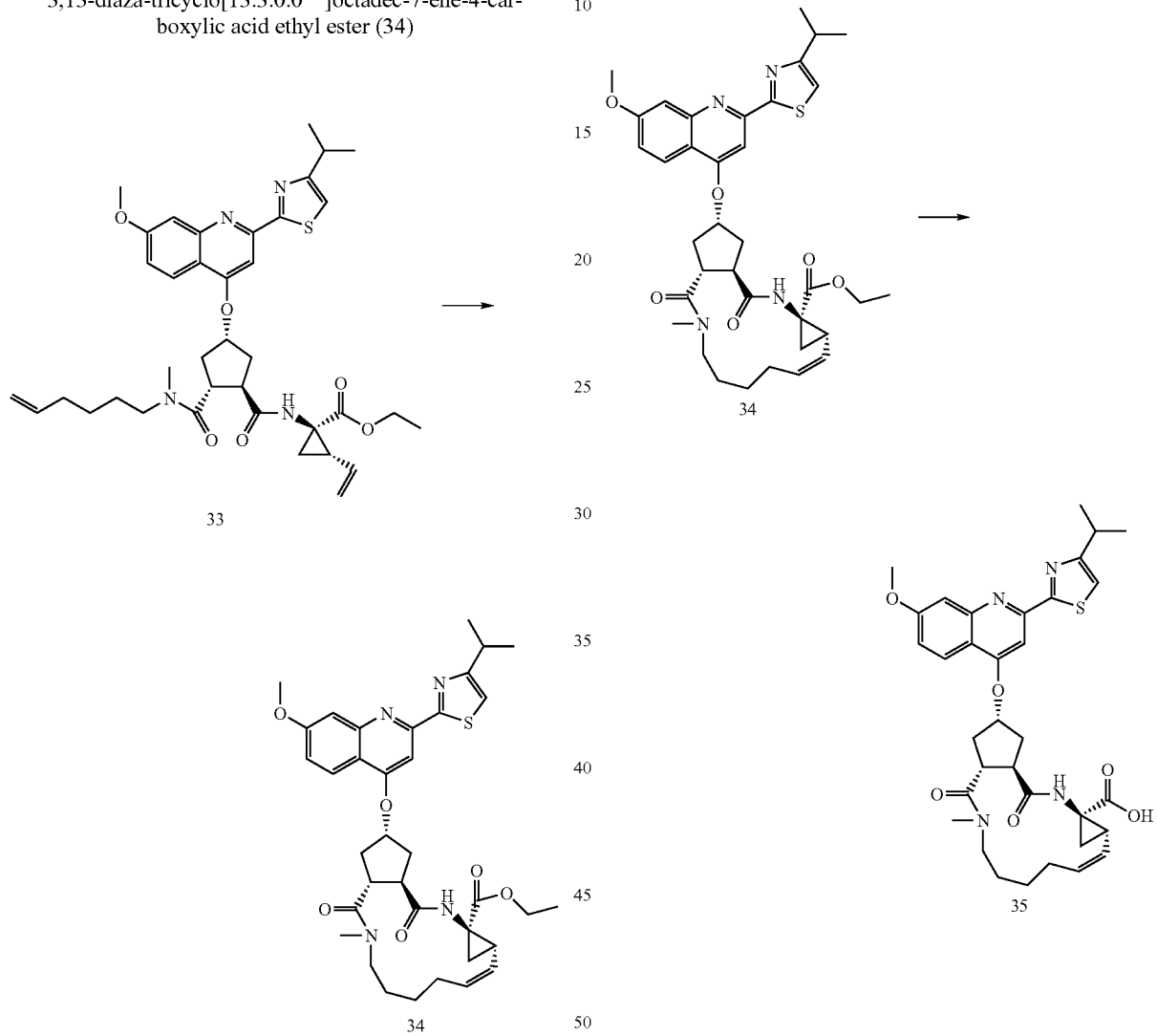

1-({2-(Hex-5-enyl-methyl-carbamoyl)-4-[2-(4-isopropyl-thiazol-2-yl)-7-methoxy-quinolin-4-yloxy]-cyclopentanecarbonyl}-amino)-2-vinyl-cyclopropanecarboxylic acid ethyl ester (33, 280 mg) was dissolved in DCE (280 mL) in a reflux setup. The system was successively evacuated and filled with argon (repeated 3 times). Then, Hoveyda-Grubbs 2$^{nd}$ generation catalyst (28 mg) was added and the system was evacuated and filled with argon twice. The resulting mixture was successively heated to refluxed overnight, concentrated, and subjected to flash column chromatography (silica, AcOEt/hexane) to give 197 mg (73%) of the title product 34 as grey-brown solid: m/z=661 (M+H)$^+$.

To a solution of 17-[2-(4-isopropyl-thiazol-2-yl)-7-methoxy-quinolin-4-yloxy]-13-methyl-2,14-dioxo-3,13-diaza-tricyclo[13.3.0.0$^{4,6}$]octadec-7-ene-4-carboxylic acid ethyl ester (34, 182 mg, 0.275 mmol) in dioxane (3 mL) and MeOH (1.5 mL) was added a 1 M aqueous solution of LiOH (3 mL). After 72 h, the reaction mixture was successively acidified to pH 2 with 1.7 M HCl and evaporated under vacuum. Then, 1 g of silica was added towards the end to adsorb the crude product. Purification by flash column chromatography (15 g YMC silica; gradient MeOH/CH$_2$Cl$_2$: 200 mL each 2%, 4%, 6%, 100 mL each 8%, 10%; forefraction 100 mL followed by 15-mL fractions, desired product fractions 33-42) gave 164 mg (94%) of the title product 35 as a yellow solid: Rf (10% MeOH—CH$_2$Cl$_2$)=0.38.

Step 5: Synthesis of N-[17-[2-(4-isopropylthiazol-2-yl)-7-methoxyquinolin-4-yloxy]-13-methyl-2,14-dioxo-3,13-diazatricyclo[13.3.0.0⁴,⁶]octadec-7-ene-4-carbonyl]-(dimethylamino)sulfonamide (37)

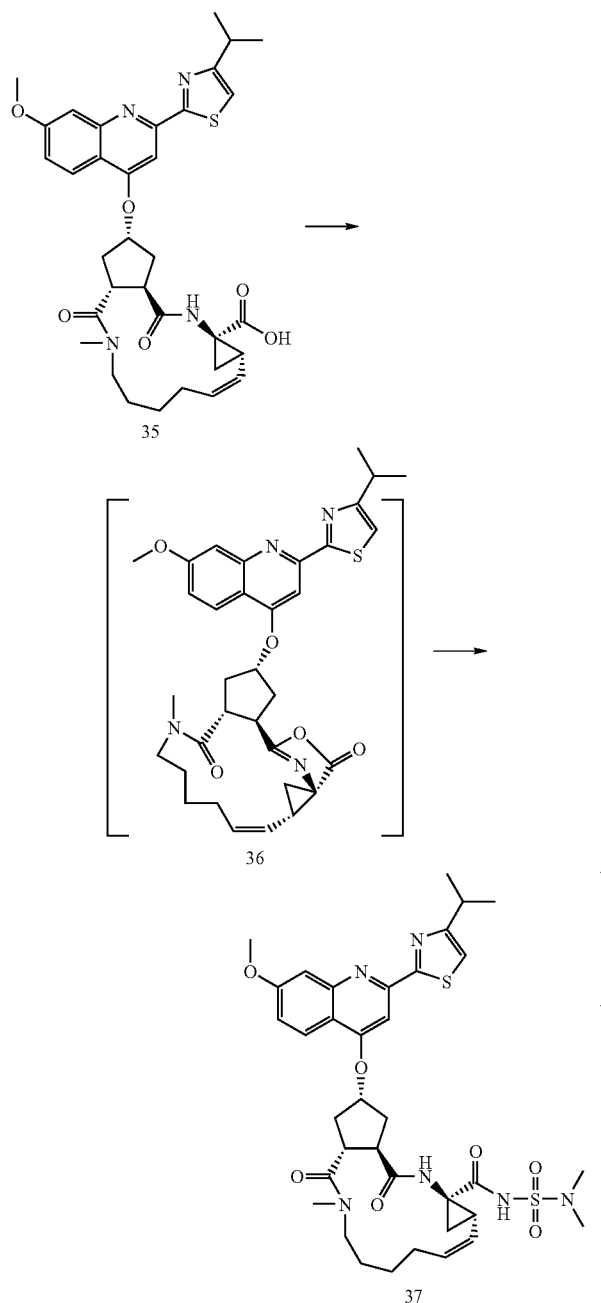

A mixture of 17-[2-(4-isopropyl-thiazol-2-yl)-7-methoxy-quinolin-4-yloxy]-13-methyl-2,14-dioxo-3,13-diaza-tricyclo[13.3.0.0⁴,⁶]octadec-7-ene-4-carboxylic acid (35, 39.8 mg, 0.063 mmol) and CDI (22 mg, 0.136 mmol) in dry THF (4 mL) was heated at 65° C. in a reflux setup. After 1.75 h the reaction mixture was cooled to room temperature. The formation of the stable intermediate 36 was observed. Then, a solution of DBU (30 μL, 0.20 mmol) and N,N-dimethylaminosulfonamide (23.4 mg, 0.19 mmol) in THF (1 mL), was added. The reaction was heated overnight at 55° C., then acidified with a 4 M solution of HCl (200 μL) in dioxane and evaporated. Purification by flash chromatography (YMC silica, gradient MeOH/AcOEt, 1:100 to 5:95) gave 4.3 mg of the title product 37 as light yellow solids: LCMS: $t_R$=3.64 min, >99% (Method Flow: 0.8 mL/min. UV 220 nm, ACE C8 3×50 mm; Mobile phase A: 10 mM NH₄Ac in 90% water, B: 10 mM NH₄Ac in 90% MeCN; Gradient: 5 to 99% B in 3 min, then 99% B for 2 min), m/z=739 (M+H)⁺. ¹H NMR (500 MHz, CDCl₃) major rotamer 1.2-1.4 (m, 3H), 1.39 (d, 6H, J=6.0 Hz), 1.46 (dd, 1H, J=9.7, 6.2 Hz), 1.66-1.80 (m, 2H), 1.87 (m, 1H), 1.99 (m, 1H), 2.22-2.32 (m, 1H), 2.32-2.46 (m, 2H), 2.50-2.62 (m, 2H), 2.80-2.84 (m, 1H), 2.98 (s, 3H), 3.04 (s, 3H), 3.20 (m, 1H), 3.40-3.44 (m, 2H), 3.77 (s, 3H), 3.97 (s, 3H), 4.6 (m, 1H), 5.05 (m, 1H), 5.37 (m, 1H), 5.68 (m, 1H), 6.39 (s, 1H), 7.05 (d, 1H, J=1.0 Hz), 7.13 (dd, 1H, J=9.0, 2.5 Hz), 7.38 (d, 1H, J=2.5 Hz), 7.51 (s, 1H), 8.04 (d, 1H, J=9.0 Hz), 10.62 (s, 1H).

Example 5

Preparation of N-[17-[2-(4-isopropylthiazol-2-yl)-7-methoxyquinolin-4-yloxy]-13-methyl-2,14-dioxo-3,13-diazatricyclo[13.3.0.0⁴,⁶]octadec-7-ene-4-carbonyl]-[(ethyl)(methyl)amino]sulfonamide (38)

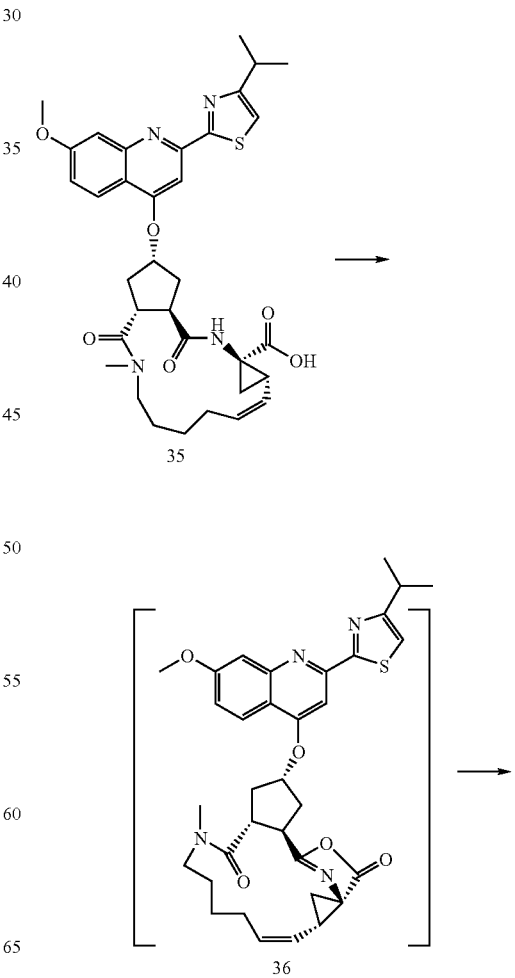

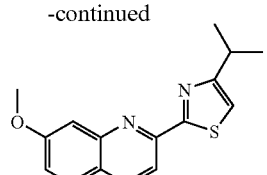

38

A mixture of 17-[2-(4-isopropyl-thiazol-2-yl)-7-methoxy-quinolin-4-yloxy]-13-methyl-2,14-dioxo-3,13-diaza-tricyclo[13.3.0.0^{4,6}]octadec-7-ene-4-carboxylic acid (35, 60 mg, 0.095 mmol) and CDI (0.23 mmol) in dry THF (5 mL) was heated at 65° C. in a reflux setup for 1 h, and then cooled to RT. The formation of the stable intermediate 36 was observed. Then, a solution of lithium bis(trimethylsilyl)amide (460 μL of 1.0M in THF) and N-ethyl-N-methylsulfonamide (62.5 mg, 0.45 mmol) in THF (7 mL), was added. After 1 h, the reaction was quenched with water, evaporated, diluted with THF, acidified with HCl in dioxane, and evaporated. Purification by flash chromatography (YMC silica, gradient MeOH/CH$_2$Cl$_2$, 2 to 5%) gave 9.6 mg of the title product as white solids. LCMS: $t_R$=3.51 min, >95%, m/z (API-ES+)=753 (M+1), $^1$H NMR (400 MHz, CDCl$_3$) major rotamer ☐ 1.16-1.28 (m, 5H), 1.36 (m, 1H), 1.39 (d, 6H, J=6.4 Hz), 1.42 (m, 1H), 1.62 (m, 1H), 1.70 (m, 1H), 1.87 (dd, 1H, J=8.2 Hz, 5.8 Hz), 2.00 (m, 1H), 2.20-2.31 (m, 1H), 2.33-2.44 (m, 2H), 2.50-2.62 (m, 2H), 2.88-2.94 (m, 4H), 3.04 (s, 3H), 3.17-3.28 (m, 2H), 3.38-3.45 (m, 3H), 3.97 (s, 3H), 4.60 (m, 1H), 5.04 (m, 1H), 5.37 (m, 1H), 5.66 (m, 1H), 6.23 (s, 1H), 7.04 (d, 1H, J=1.2 Hz), 7.12 (dd, 1H, J=8.8, 2.8 Hz), 7.37 (d, 1H, J=2.8 Hz), 7.51 (m, 1H), 8.03 (d, 1H, J=8.8 Hz), 10.53 (s, 1H).

Example 6

Synthesis of Chrystalline Cyclopentane

Synthesis of 3-Oxo-2-oxa-bicyclo[2.2.1]heptane-5-carboxylic acid tert-butyl ester (40)

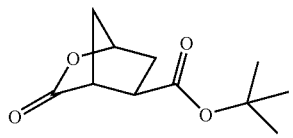

DMAP (14 mg, 0.115 mmol) and Boc$_2$O (252 mg, 1.44 mmol) was added to a stirred solution of 39 (180 mg, 1.15 mmol) in 2 mL CH$_2$Cl$_2$ under inert argon atmosphere at 0° C. The reaction was allowed to warm to room temperature and was stirred overnight. The reaction mixture was concentrated and the crude product was purified by flash column chromatography (toluene/ethyl acetate gradient 15:1, 9:1, 6:1, 4:1, 2:1) which gave the title compound (124 mg, 51%) as white crystals.

$^1$H-NMR (300 MHz, CD$_3$OD) δ 1.45 (s, 9H), 1.90 (d, J=11.0 Hz, 1H), 2.10-2.19 (m, 3H), 2.76-2.83 (m, 1H), 3.10 (s, 1H), 4.99 (s, 1H); $^{13}$C-NMR (75.5 MHz, CD$_3$OD) δ 27.1, 33.0, 37.7, 40.8, 46.1, 81.1, 81.6, 172.0, 177.7.

Alternative method for the preparation of compound 40

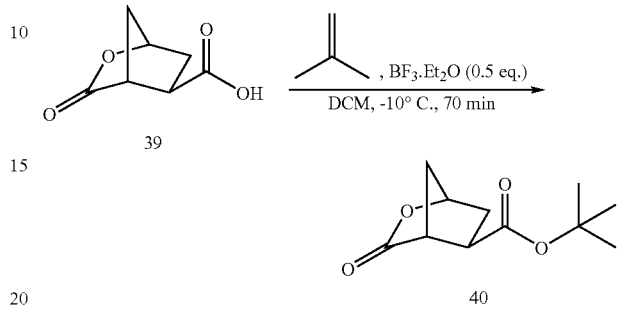

Compound 39 (13.9 g, 89 mmol) was dissolved in dichloromethane (200 ml) and then cooled to approximately −10° C. under nitrogen. Isobutylene was then bubbled into the solution until the total volume had increased to approximately 250 ml which gave a turbid solution. BF$_3$.Et$_2$O (5.6 ml, 44.5 mmol, 0.5 eq.) was added and the reaction mixture was kept at approximately −10° C. under nitrogen. After 10 min, a clear solution was obtained. The reaction was monitored by TLC (EtOAc-Toluene 3:2 acidified with a few drops of acetic acid and hexane-EtOAc 4:1, staining with basic permanganate solution). At 70 min only traces of compound 39 remained and aq. saturated NaHCO$_3$ (200 ml) was added to the reaction mixture, which was then stirred vigorously for 10 min. The organic layer was washed with saturated NaHCO$_3$ (3×200 ml) and brine (1×150 ml), then dried with sodium sulfite, filtered and the residue was evaporated to an oily residue. Upon addition of hexane to the residue, the product precipitated. Addition of more hexane and heating to reflux gave a clear solution from which the product crystallized. The crystals were collected by filtration and were washed with hexane (rt), then air-dried for 72 h giving colourless needles (12.45 g, 58.7 mmol, 66%).

Example 7

Synthesis of a Quinazoline as a P2 Building Block 2-(4-Fluorobenzoylamino)-4-methoxy-3-methylbenzoic acid methyl ester (41)

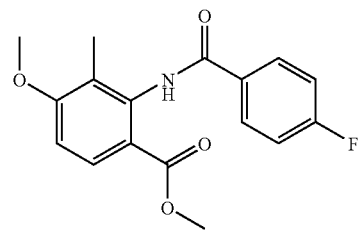

4-Fluoro benzoic acid (700 mg, 5 mmol) was dissolved in dichloromethane (20 ml) and pyridine (2 ml). 2-Amino-4-methoxy-3-methyl-benzoic acid methyl ester (878 mg, 4.5 mmol) was added and the mixture was refluxed for 5 h. Water was added and the mixture was extracted with dichloromethane. The organic phase was dried, filtered and evaporated and the afforded residue was purified by column chromatography on silica gel, eluted with ether-pentane 1:1 which gave pure title compound (870 mg, 61%).

MS (M+H$^+$) 318.

2-(4-Fluoro-benzoylamino)-4-methoxy-3-methyl-benzoic acid (42)

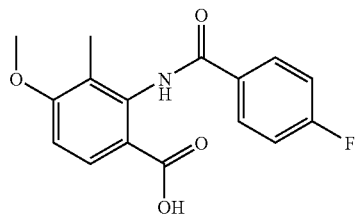

LiOH (1M, 4 mL) was added to a solution of 2-(4-fluoro-benzoylamino)-4-methoxy-3-methyl-benzoic acid methyl ester (41) (870 mg, 2.7 mmol), in tetrahydrofuran (15 ml), water (7.5 ml) and methanol (7.5 ml). The mixture was heated to 50° C. for 4 h. Water (30 ml) was then added and the volume reduced to half. Acidification with acetic acid followed by filtration gave pure title compound (830 mg, 100%).

MS (M+H$^+$) 304.

2-(4-Fluoro-phenyl)-7-methoxy-8-methyl-quinazolin-4-ol (43)

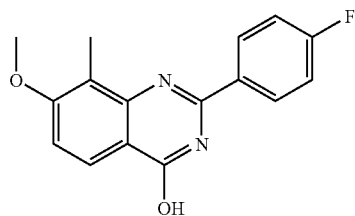

2-(4-Fluoro-benzoylamino)-4-methoxy-3-methyl-benzoic acid (42) (830 mg, 2.7 mmol) was heated to 150° C. in formamide (20 ml) for 4 h. The excess formamide was removed by distillation. Water was added and the precipitated product was filtered of to give pure title compound (642 mg, 83%).

MS (M+H$^+$) 285.

Example 8

General Procedure for the Preparation of Substituted quinazolin-4-ols

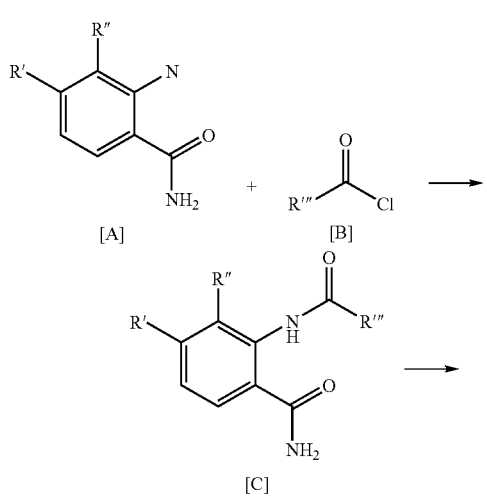

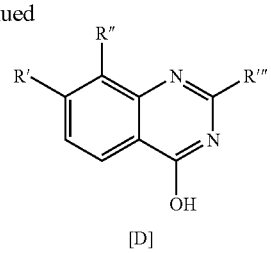

To a suspension of a substituted 2-amino-benzamide [A] (1 eq) in dry THF (60 ml) was added pyridine (2 eq) and the mixture was cooled to 5° C. The acid chloride [B] (1.25 eq) was added slowly and the mixture was stirred at room temperature overnight. The mixture was evaporated under reduced pressure and then suspended in water. The compound was left in the water for some hours, filtered and washed with cold water and diethyl ether. The product [C] was dried under vacuum. Yield: 90-100%. When the acid chloride [B] used was a nicotinyl chloride hydrochloride, then 2.5 eq of pyridine was used and the mixture was stirred for 2-3 days at room temperature instead of over night.

The formed amide [C] (1 eq) was added to a suspension of sodium carbonate (2.5 eq) in a 1:1 mixture of water and EtOH and the mixture was refluxed for two hours. The EtOH was removed under reduced pressure, a solution of 5% citric acid was added and the mixture was allowed to stay overnight. The product [D] was isolated by filtration, then washed with water and diethyl ether and dried under vacuum.

Example 9

7-Methoxy-8-methyl-2-pyridin-3-yl-quinazolin-4-ol (44)

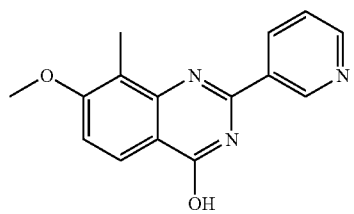

The general procedure described in Example 8 was followed using 2-amino-4-methoxy-3-methyl benzamide as benzamide derivative and nicotinyl chloride hydrochloride as acid chloride, which gave the title compound (2.5 g, 92%), [M+H]=268.

Example 10

7-Methoxy-8-methyl-2-pyridin-4-yl-quinazolin-4-ol (45)

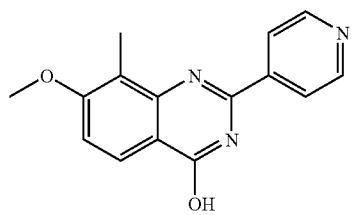

The general procedure described in Example 8 was followed using 2-amino-4-methoxy-3-methyl benzamide as benzamide derivative and isonicotinoyl chloride hydrochloride as acid chloride, which gave the title compound (1.6 g, 60%), [M+H]=268.

Example 11

7-Methoxy-8-methyl-2-ethyl-quinazolin-4-ol (46)

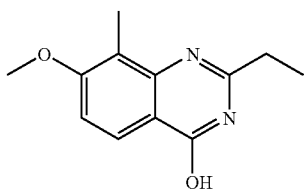

The general procedure described in Example 8 was followed using 2-amino-4-methoxy-3-methyl benzamide as benzamide derivative [A] and acetic acid chloride as acid chloride [B], which gave the title compound (2.2 g, 100%).
$^1$H-NMR DMSO-D$_6$ δ 1.2 (m, 3H), 2.38 (s, 3H), 2.6 (m, 2H), 3.90 (s, 3H), 7.18 (d, 2H), 7.96 (d, 2H), 11.88 (s, 1H).

Example 12

7-Methoxy-8-methyl-2-(4-methoxyphenyl)-quiazolin-4-ol (47)

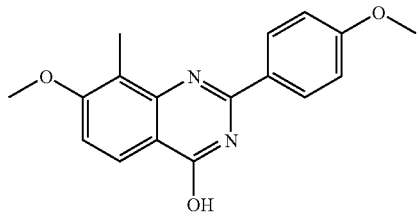

The general procedure described in Example 8 was followed using 2-amino-4-methoxy-3-methyl benzamide as benzamide derivative [A] and 4-methoxybenzoic acid chloride as acid chloride [B], which gave the title compound (5.5 g, 92%).
$^1$H-NMR DMSO-D$_6$ δ 2.38 (s, 3H), 3.82 (s, 3H), 3.92 (s, 3H), 7.04 (d, 2H), 7.20 (d, 1H), 8.00 (d, 1H), 8.20 (d, 2H), 12.18 (s, 1H).

Example 13

8-Methoxy-2-phenyl-quinazolin-4-ol (48)

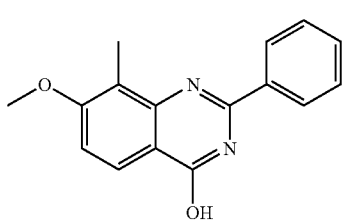

The general procedure described in Example 8 was followed using 2-amino-4-methoxy-3-methyl benzamide as benzamide derivative [A] and benzoyl chloride as acid chloride [B], which gave the title compound (2.0 g, 80%), [M+H]=253.
$^1$H-NMR DMSO-D$_6$ δ 3.97 (s, 3H), 7.39-7.72 (m, 6H), 8.19 (m, 2H), 12.48 (s, 1H).

Example 14

2-(3-Fluoro-phenyl)-7-methoxy-8-methyl-quinazolin-4-ol (49)

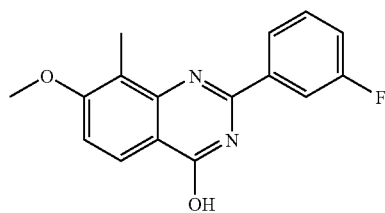

The general procedure described in Example 8 was followed using 2-amino-4-methoxy-3-methyl benzamide as benzamide derivative [A] and 3-fluoro-benzoyl chloride as acid chloride [B], which gave the title compound (2.1 g, 73%), [M+H]=271.

Example 15

2-(3, 5-Difluoro-phenyl)-7-methoxy-8-methyl-quinazolin-4-ol (50)

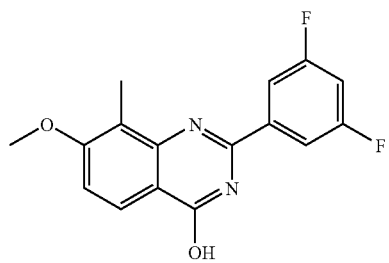

The general procedure described in Example 8 was followed using 2-amino-4-methoxy-3-methyl benzamide as benzamide derivative [A] and 3,5-difluoro-benzoyl chloride as acid chloride [B], which gave the title compound (2.1 g, 85%), [M+H]=303.

Example 16

7-Methoxy-8-methyl-quinazolin-4-ol (51)

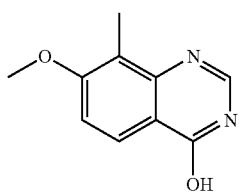

The title compound was formed as a biproduct when the ring closing reaction, step [B] to [C], in the general procedure was performed in DMF rather than in EtOH.

Example 17

Activity of Compounds of Formula (I)

Replicon Assay

The compounds of formula (I) were examined for activity in the inhibition of HCV RNA replication in a cellular assay. The assay demonstrated that the compounds of formula (I) exhibited activity against HCV replicons functional in a cell culture. The cellular assay was based on a bicistronic expression construct, as described by Lohmann et al. (1999) Science vol. 285 pp. 110-113 with modifications described by Krieger et al. (2001) Journal of Virology 75: 4614-4624, in a multi-target screening strategy. In essence, the method was as follows.

The assay utilized the stably transfected cell line Huh-7 luc/neo (hereafter referred to as Huh-Luc). This cell line harbors an RNA encoding a bicistronic expression construct comprising the wild type NS3-NS5B regions of HCV type 1b translated from an Internal Ribosome Entry Site (IRES) from encephalomyocarditis virus (EMCV), preceded by a reporter portion (FfL-luciferase), and a selectable marker portion (neo$^R$, neomycine phosphotransferase). The construct is bordered by 5' and 3' NTRs (non-translated regions) from HCV type 1b. Continued culture of the replicon cells in the presence of G418 (neo$^R$) is dependent on the replication of the HCV RNA. The stably transfected replicon cells that express HCV RNA, which replicates autonomously and to high levels, encoding inter alia luciferase, are used for screening the antiviral compounds.

The replicon cells were plated in 384 well plates in the presence of the test and control compounds which were added in various concentrations. Following an incubation of three days, HCV replication was measured by assaying luciferase activity (using standard luciferase assay substrates and reagents and a Perkin Elmer ViewLux™ ultraHTS microplate imager). Replicon cells in the control cultures have high luciferase expression in the absence of any inhibitor. The inhibitory activity of the compound on luciferase activity was monitored on the Huh-Luc cells, enabling a dose-response curve for each test compound. EC50 values were then calculated, which value represents the amount of the compound required to decrease by 50% the level of detected luciferase activity, or more specifically, the ability of the genetically linked HCV replicon RNA to replicate.

Inhibition Assay

The aim of this in vitro assay was to measure the inhibition of HCV NS3/4A protease complexes by the compounds of the present invention. This assay provides an indication of how effective compounds of the present invention would be in inhibiting HCV NS3/4A proteolytic activity.

The inhibition of full-length hepatitis C NS3 protease enzyme was measured essentially as described in Poliakov, 2002 Prot Expression & Purification 25 363 371. Briefly, the hydrolysis of a depsipeptide substrate, Ac-DED(Edans)EEA-buψ[COO]ASK(Dabcyl)-NH$_2$ (AnaSpec, San José, USA), was measured spectrofluorometrically in the presence of a peptide cofactor, KKGSVVIVGRIVLSGK (Åke Engström, Department of Medical Biochemistry and Microbiology, Uppsala University, Sweden). [Landro, 1997 #Biochem 36 9340-9348]. The enzyme (1 nM) was incubated in 50 mM HEPES, pH 7.5, 10 mM DTT, 40% glycerol, 0.1% n-octyl-D-glucoside, with 25 μM NS4A cofactor and inhibitor at 30° C. for 10 min, whereupon the reaction was initiated by addition of 0.5 μM substrate. Inhibitors were dissolved in DMSO, sonicated for 30 sec. and vortexed. The solutions were stored at −20° C. between measurements.

The final concentration of DMSO in the assay sample was adjusted to 3.3%. The rate of hydrolysis was corrected for inner filter effects according to published procedures. [Liu, 1999 Analytical Biochemistry 267 331-335]. Ki values were estimated by non-linear regression analysis (GraFit, Erithacus Software, Staines, MX, UK), using a model for competitive inhibition and a fixed value for Km (0.15 μM). A minimum of two replicates was performed for all measurements.

The following Table 1 lists compounds that were prepared according to any one of the above examples. The activities of the compounds tested are also depicted in Table 1.

| Compound nr. | structure | EC$_{50}$ (μM) Replicon assay | Ki (nM) Enzymatic assay |
|---|---|---|---|
| 37 | 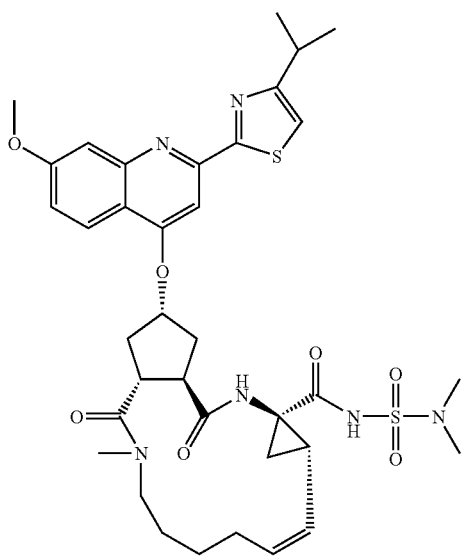 | 0.3 | 24 |

| Compound nr. | structure | EC$_{50}$ (μM) Replicon assay | Ki (nM) Enzymatic assay |
|---|---|---|---|
| 38 | 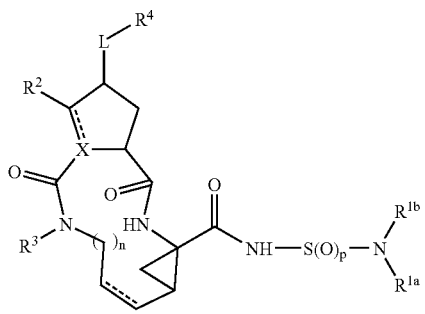 | 0.3 | 24 |

The invention claimed is:
1. A compound having the formula

(I)

an N-oxide, salt, or stereoisomer thereof,
wherein each dashed line (represented by - - -) represents an optional double bond;
X is N, CH and where X bears a double bond it is C;
$R^{1a}$ and $R^{1b}$ are, independently, hydrogen, $C_{3-7}$cycloalkyl, aryl, Het, $C_{1-6}$alkoxy, $C_{1-6}$alkyl optionally substituted with halo, $C_{1-6}$alkoxy, cyano, polyhalo$C_{1-6}$alkoxy, $C_{3-7}$cycloalkyl, aryl, or with Het; or $R^{1a}$ and $R^{1b}$ together with the nitrogen to which they are attached form a 4 to 6 membered saturated, partially unsaturated or completely unsaturated heterocyclic ring optionally containing additional 1 to 3 heteroatoms each independently selected from nitrogen, oxygen and sulfur, and wherein said heterocyclic ring may be optionally substituted with one or two substituents each independently selected from the group consisting of halo, $C_{1-6}$alkyl, polyhalo$C_{1-6}$alkyl, hydroxy, $C_{1-6}$alkoxy, polyhalo$C_{1-6}$alkoxy, $C_{1-6}$alkoxy$C_{1-6}$alkyl, carboxyl, $C_{1-6}$alkylcarbonyl, cyano, mono- and di$C_{1-6}$alkylamino, aryl and aryl$C_{1-6}$alkyl;
L is a direct bond, —O—, —O—$C_{1-4}$alkanediyl-, —O—CO—, —O—C(=O)—NR$^{5a}$— or —O—C(=O)—NR$^{5a}$—$C_{1-4}$alkanediyl-;

$R^2$ is hydrogen, and where X is C or CH, $R^2$ may also be $C_{1-6}$alkyl;
$R^3$ is hydrogen, $C_{1-6}$alkyl, $C_{1-6}$alkoxy$C_{1-6}$alkyl, $C_{3-7}$cycloalkyl, amino, mono- or di$C_{1-6}$alkylamino;
$R^4$ is aryl or a saturated, a partially unsaturated or completely unsaturated 5 or 6 membered monocyclic or 9 to 12 membered bicyclic heterocyclic ring system wherein said ring system contains one nitrogen, and optionally one to three additional heteroatoms selected from the group consisting of oxygen, sulfur and nitrogen, and wherein the remaining ring members are carbon atoms; wherein said ring system may be optionally substituted on any carbon or nitrogen ring atom with one, two, three, or four substituents each independently selected from $C_{3-7}$cycloalkyl, aryl, Het, —C(=O)NR$^{5a}$R$^{5b}$, —C(=O)R$^7$, —C(=O)OR$^{6a}$, and $C_{1-6}$alkyl optionally substituted with $C_{3-7}$cycloalkyl, aryl, Het, —C(=O)NR$^{5a}$R$^{5b}$, —NR$^{5a}$R$^{5b}$, —C(=O)R$^7$, —NR$^{5a}$C(=O)R$^7$, —NR$^{5a}$SO$_p$R$^8$, —SO$_p$R$^8$, —SO$_p$NR$^{5a}$R$^{5b}$, —C(=O)OR$^6$, or —NR$^{5a}$C(=O)OR$^{6a}$; and wherein the substituents on any carbon atom of the heterocyclic ring may also be selected from $C_{1-6}$alkoxy, hydroxy, halo, polyhalo-$C_{1-6}$alkyl, $C_{1-6}$alkylthio, oxo, cyano, nitro, azido, —NR$^{5a}$R$^{5b}$, —NR$^{5a}$C(=O)R$^7$, —NR$^{5a}$SO$_p$R$^8$, —SO$_p$R$^8$, —SO$_p$NR$^{5a}$R$^{5b}$, —C(=O)OH, and —NR$^{5a}$C(=O)OR$^{6a}$;
n is 3, 4, 5, or 6;
p is 1 or 2;
each $R^{5a}$ and $R^{5b}$ are, independently, hydrogen, $C_{3-7}$cycloalkyl, aryl, Het, $C_{1-6}$alkyl optionally substituted with halo, $C_{1-6}$alkoxy, cyano, polyhalo$C_{1-6}$alkoxy, $C_{3-7}$cycloalkyl, aryl, or with Het;
$R^6$ is hydrogen, $C_{2-6}$alkenyl, $C_{3-7}$cycloalkyl, Het, or $C_{1-6}$alkyl optionally substituted with $C_{3-7}$cycloalkyl, aryl or Het;
$R^7$ is $C_{2-6}$alkenyl, $C_{3-7}$cycloalkyl, Het, or $C_{1-6}$alkyl optionally substituted with $C_{3-7}$cycloalkyl, aryl or Het;
$R^7$ is hydrogen, $C_{1-6}$alkyl, $C_{3-7}$cycloalkyl, or aryl;

$R^8$ is hydrogen, polyhalo$C_{1-6}$alkyl, $C_{3-7}$cycloalkyl, aryl, Het, or $C_{1-6}$alkyl optionally substituted with $C_{3-7}$cycloalkyl, aryl or Het;

aryl as a group or part of a group is phenyl, naphthyl, indanyl, or 1,2,3,4-tetrahydro-naphthyl, each of which may be optionally substituted with one, two or three substituents selected from halo, $C_{1-6}$alkyl, polyhalo$C_{1-6}$alkyl, hydroxy, $C_{1-6}$alkoxy, polyhalo$C_{1-6}$alkoxy, $C_{1-6}$alkoxy$C_{1-6}$alkyl, carboxyl, $C_{1-6}$alkylcarbonyl, $C_{1-6}$alkoxycarbonyl, cyano, nitro, amino, mono- or di$C_{1-6}$alkylamino, aminocarbonyl, mono- or di$C_{1-6}$alkylaminocarbonyl, azido, mercapto, $C_{3-7}$cycloalkyl, phenyl, pyridyl, thiazolyl, pyrazolyl, pyrrolidinyl, piperidinyl, piperazinyl, 4-$C_{1-6}$alkylpiperazinyl, 4-$C_{1-6}$alkylcarbonyl-piperazinyl, and morpholinyl;

wherein the morpholinyl and piperidinyl groups may be optionally substituted with one or with two $C_{1-6}$alkyl radicals; and the phenyl, pyridyl, thiazolyl, pyrazolyl groups may be optionally substituted with 1, 2 or 3 substituents each independently selected from $C_{1-6}$alkyl, $C_{1-6}$alkoxy, halo, amino, mono- or di$C_{1-6}$alkylamino;

Het as a group or part of a group is a 5 or 6 membered saturated, partially unsaturated or completely unsaturated heterocyclic ring containing 1 to 4 heteroatoms each independently selected from nitrogen, oxygen and sulfur, being optionally condensed with a benzene ring, and wherein the group Het as a whole may be optionally substituted with one, two or three substituents each independently selected from the group consisting of halo, $C_{1-6}$alkyl, polyhalo$C_{1-6}$alkyl, hydroxy, $C_{1-6}$alkoxy, polyhalo$C_{1-6}$alkoxy, $C_{1-6}$alkoxy$C_{1-6}$alkyl, carboxyl, $C_{1-6}$alkylcarbonyl, $C_{1-6}$alkoxycarbonyl, cyano, nitro, amino, mono- or di$C_{1-6}$alkylamino, aminocarbonyl, mono- or di$C_{1-6}$alkylaminocarbonyl, $C_{3-7}$cycloalkyl, phenyl, pyridyl, thiazolyl, pyrazolyl, pyrrolidinyl, piperidinyl, piperazinyl, 4-$C_{1-6}$alkylpiperazinyl, 4-$C_{1-6}$alkylcarbonyl-piperazinyl, and morpholinyl; wherein the morpholinyl and piperidinyl groups may be optionally substituted with one or with two $C_{1-6}$alkyl radicals; and the phenyl, pyridyl, thiazolyl, pyrazolyl groups may be optionally substituted with 1, 2 or 3 substituents each independently selected from $C_{1-6}$alkyl, $C_{1-6}$alkoxy, halo, amino, mono- or di$C_{1-6}$alkylamino.

2. A compound according to claim 1, wherein the compound has the formula (I-c), (I-d), or (I-e):

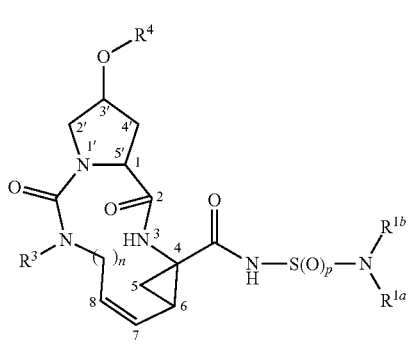

(I-c)

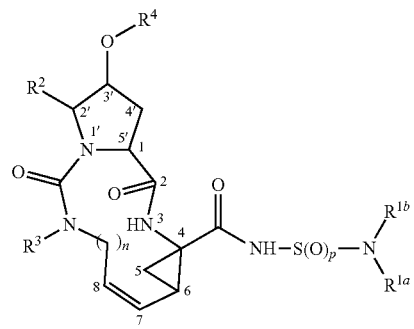

(I-d)

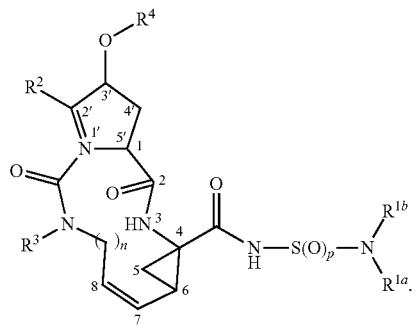

(I-e)

3. A compound according to any one of claims 1-2, wherein
(a) each $R^{1a}$ and $R^{1b}$ are, independently, hydrogen, or methyl, ethyl, or tert-butyl; or
(b) one of $R^{1a}$ and $R^{1b}$ is cyclopropyl, or phenyl; or
(c) $R^{1a}$ and $R^{1b}$ together with the nitrogen to which they are attached form pyrrolidinyl, piperidinyl, piperazinyl, 4-$C_{1-6}$alkylpiperazinyl, 4-$C_{1-6}$alkylcarbonylpiperazinyl-piperazinyl, or morpholinyl; or
(d) one of $R^{1a}$ and $R^{1b}$ is a Het group selected from

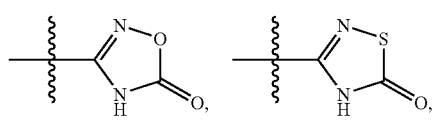

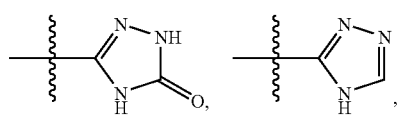

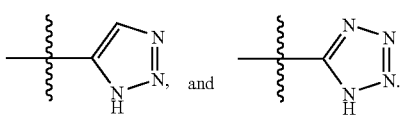

4. A compound according to claim 1, wherein L is —O—, —O—CO— or a direct bond.

5. A compound according to claim 1, wherein L is —O— and $R^1$ is quinolinyl, quinolin-4-yl, isoquinolinyl, isoquinolin-1-yl, quinazolinyl), quinazolin-4-yl, or pyrimidinyl, pyrimidin-4-yl, either of which is, independently, optionally mono, di, or tri substituted with $C_{1-6}$alkyl, $C_{1-6}$alkoxy, nitro, hydroxy, halo, trifluoromethyl, —NR$^{5a}$R$^{5b}$, —C(=O) NR$^{5a}$R$^{5b}$, $C_{3-7}$cycloalkyl, aryl, Het, —C(=O)OH, or —C(=O)OR$^{6a}$; wherein aryl or Het are each, independently, optionally substituted with halo, C$_{1-6}$alkyl, C$_{1-6}$alkoxy, amino, mono- or diC$_{1-6}$alkylamino, pyrrolidinyl, piperidinyl, piperazinyl, 4-C$_{1-6}$alkylpiperazinyl, 4-methylpiperazinyl, or morpholinyl; and wherein the morpholinyl and piperidinyl groups may optionally substituted with one or two C$_{1-6}$alkyl radicals.

6. A compound according to claim 1, wherein L is —O— and R$^4$ is (d-1) a radical of formula

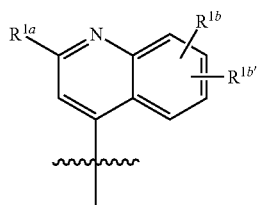

(d-1)

(d-2) a radical of formula

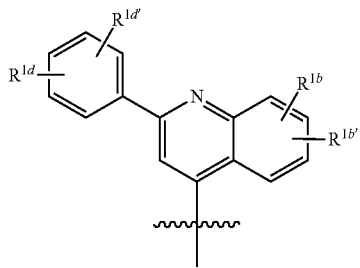

(d-2)

(d-3) a radical of formula

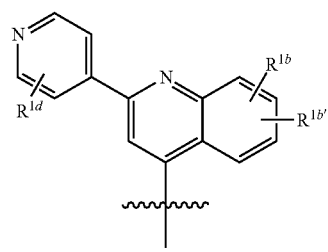

(d-3)

(d-4) a radical of formula

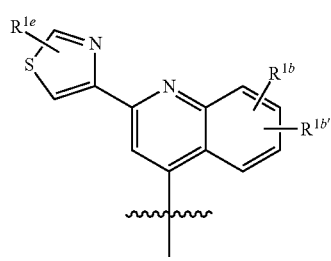

(d-4)

or (d-4-a) a radical of formula

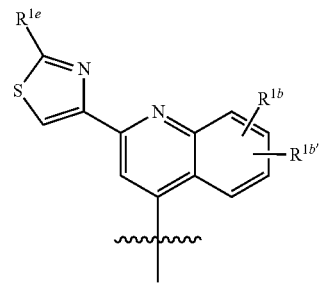

(d-4-a)

(d-5) a radical of formula

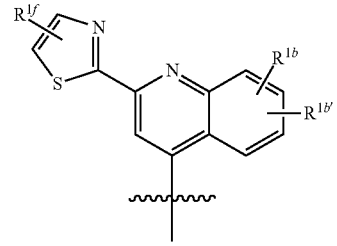

(d-5)

or (d-5-a) a radical of formula

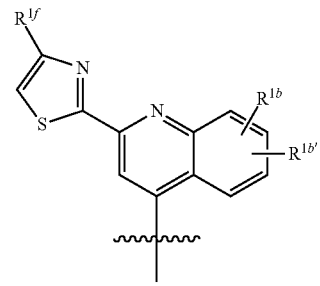

(d-5-a)

wherein in radicals (d-1)-(d-5), as well as in (d-4-a) and (d-5-a):
each R$^{4a}$, R$^{4b}$, R$^{4b'}$, R$^{4d}$, R$^{4d'}$, R$^{4e}$, R$^{4f}$ are independently any of the substituents selected from those mentioned as possible substituents on the monocyclic or bicyclic ring systems of R$^4$, as specified in claim 1.

7. A compound according to claim 6 wherein L is —O— and R$^4$ is a radical of formula

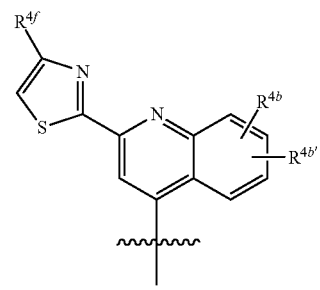

(d-5-a)

wherein $R^{4f}$ is hydrogen, $C_{1-6}$alkyl, amino, mono- or di$C_{1-6}$alkylamino, pyrrolidinyl, piperidinyl, piperazinyl, 4-$C_{1-6}$alkylpiperazinyl, 4-methylpiperazinyl, or morpholinyl.

8. A compound according to claim 1, wherein $R^3$ is
   (a) $R^3$ is hydrogen; or
   (b) $R^3$ is $C_{1-6}$alkyl; or
   (c) $R^3$ is amino, or mono- or di$C_{1-6}$alkylamino.

9. A compound according to claim 1, wherein n is 4 or 5.

10. A compound according to claim 1, wherein $R^2$ is hydrogen.

11. A compound according to claim 1, other than an N-oxide, or salt.

12. A combination comprising
    (a) a compound as defined in claim 1 or a pharmaceutically acceptable salt thereof; and
    (b) ritonavir, or a pharmaceutically acceptable salt thereof.

13. A pharmaceutical composition comprising a carrier, and as active ingredient an anti-virally effective amount of a compound of claim 1.

14. A method of inhibiting HCV replication in a warm-blooded animal said method comprising:
    administering an effective amount of a compound according to claim 1 or a pharmaceutically acceptable salt thereof; or
    administering in combination an effective amount of said compound or said pharmaceutically acceptable salt thereof and an effective amount of ritonavir or a pharmaceutically acceptable salt thereof.

15. A process for preparing a compound as claimed in claim 1, wherein said process comprises:
    (a) preparing a compound of formula (I) wherein the bond between $C_7$ and $C_8$ is a double bond, which is a compound of formula (I-i), by forming a double bond between $C_7$ and $C_8$, in particular via an olefin metathesis reaction, with concomitant cyclization to the macrocycle as outlined in the following reaction scheme:

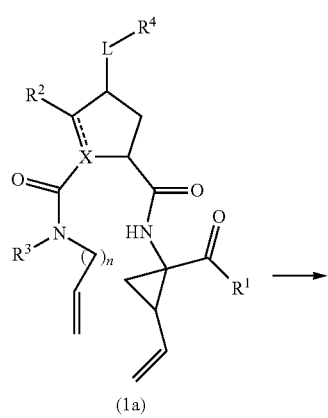

(1a)

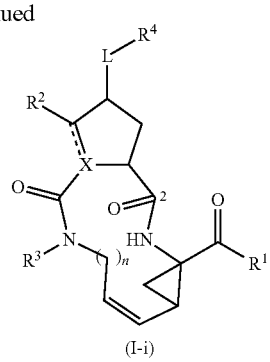

(I-i)

wherein in the above and following structural formulae the group

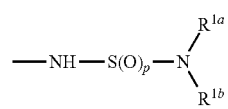

is represented by —$R^1$;

(b) converting a compound of formula (I-i) to a compound of formula (I) wherein the link between C7 and C8 in the macrocycle is a single bond, i.e, a compound of formula (I-j):

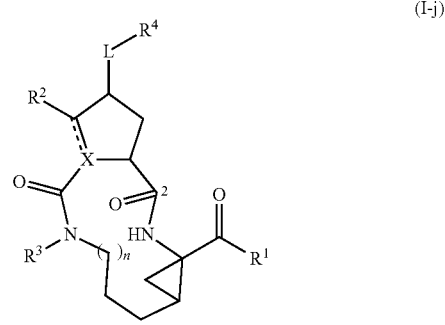

by a reduction of the $C_7$-$C_8$ double bond in the compounds of formula (I-j);

(c) forming an amide bond between a intermediate (2a) and an sulfonylamide (2b), as outlined in the following scheme wherein G represents a group:

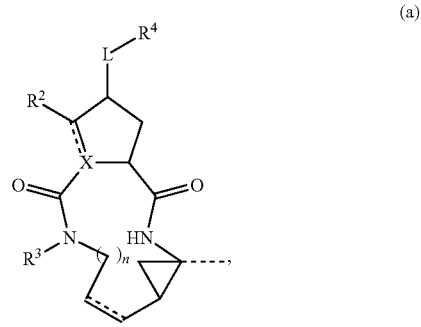

US 8,227,407 B2

115

-continued

G—COOH + H₂N—S(O)$_p$—N(R$^{1a}$)(R$^{1b}$) →
(2a)         (2b)

$$\underset{(I)}{G-\underset{H}{N}-S(O)_p-N(R^{1a})(R^{1b})}$$ 
(with C=O on the N—H carbon)

(d) preparing a compound of formula (I) wherein R³ is hydrogen, said compound being represented by (1-L), from a corresponding nitrogen-protected intermediate (3a), wherein PG represents a nitrogen protecting group:

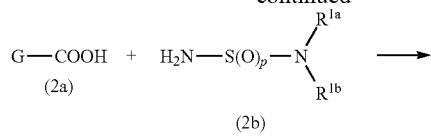

(3a)

↓

(I-L)

(e) reacting an intermediate (4a) with a intermediate (4b), (4c), (4d), (4e) or (4f) as outlined in the following reaction scheme:

116

(4a)

Y—R⁴          (4b)
HNR$^{5a}$R⁴   (4c)
HNR$^{5a}$—C$_{1-4}$Alk—R⁴  (4d)
R⁴—COOH       (4e)
R⁴—C$_{1-4}$Alk—OH  (4f)

→

(I)

wherein Y in (4a) represents hydroxy or a leaving group; which reaction in particular is an O-arylation reaction wherein Y represents a leaving group, or a Mitsunobu reaction, wherein Y represents hydroxy; and wherein (4a) and (4c) or (4d) are reacted in the presence of a carbonyl introducing agent to form L being a urethane group (L is —O—C(=O)—NR$^{5a}$—); and wherein (4a) and (4e) are reacted in an ester forming procedure; and wherein (4a) and (4f) are reacted in an ether forming procedure;

(f) converting compounds of formula (I) into each other by a functional group transformation reaction; or (g) preparing a salt form by reacting the free form of a compound of formula (I) with an acid or a base.

16. A pharmaceutical composition comprising a carrier, and a combination according to claim 12.

* * * * *